United States Patent [19]

Racaniello et al.

[11] Patent Number: 5,525,715

[45] Date of Patent: Jun. 11, 1996

[54] METHOD FOR PRODUCING RNA VIRUSES FROM CDNA

[75] Inventors: Vincent Racaniello, New York, N.Y.; Joanne M. Tatem, Lincoln Park, N.J.; Carolyn L. Weeks-Levy, Valhalla, N.Y.

[73] Assignee: The Trustees of Columbia University in the City of New York, New York, N.Y.

[21] Appl. No.: 852,260

[22] PCT Filed: Aug. 20, 1991

[86] PCT No.: PCT/US91/05890

§ 371 Date: Jun. 19, 1992

§ 102(e) Date: Jun. 19, 1992

[87] PCT Pub. No.: WO92/03538

PCT Pub. Date: Mar. 5, 1992

Related U.S. Application Data

[63] Continuation-in-part of Ser. No. 569,916, Aug. 20, 1990, abandoned, and Ser. No. 570,000, Aug. 20, 1990, abandoned.

[51] Int. Cl.$^6$ .................................................. C12N 15/43
[52] U.S. Cl. ..................... 536/23.72; 435/172.3; 435/235.1; 424/185.1; 424/216.1; 424/217.1
[58] Field of Search ............................ 424/88, 89, 93 A, 424/93 T, 185.1, 216.1, 217.1; 435/172.1, 172.3, 235.1, 236; 536/23.72

[56] References Cited

U.S. PATENT DOCUMENTS 4,719,177  1/1988  Baltimore et al. ..................... 435/91

OTHER PUBLICATIONS

Ellis, R. W. "New technologies for making vaccines", In: Vaccines, Plotkin & Mortimer Eds. W. B. Saunders Co. (1988) pp. 568–575.

Bosleys, J. W. et al., "Gonorrhea Vaccines", In: Vaccines & Immunotherapy S. J. Cryz Ed., Pergamon Press pp. 211–223 (1991).

Kumar, V. et al. "Amino acid variations at a single residue in an autoimmune peptide profoundly affect its properties: T cell activation, major histocompatability complex binding, and ability to block experimental allergic encephalomyelitis" Proc. Natl. Acad. Sci. 87: 1337–1341 (1990).

Bowie, J. V. et al. "Deciphering the message in protein sequences: tolerance to amino acid substitutions", Science 247: 1306–1310 (1990).

Kuhn, R. J. et al. "Expression of the poliovirus genome from infectious cDNA is dependent upon arrangements of eukaryotic & prokaryotic sequences in recombinant plasmids" Virology 157: 560–64 (1987).

Roos, R. P. et al. "Infectious cDNA clones of the DA strain of Theider's murine encephalomyelitis virus" J. Virol. 63(12): 5492–5496.

Toyoda, H. et al. 1984. J. Mol. Biol. 174:561–585.

Stanway, G. et al. 1983. Nuc. Acid. Res. 11(16): 5629–5643.

Davis, et tal. 1980. Microbiology pp. 1096–1108.

Verma, I. M. 1981. In: The Enzymes. pp. 87–103.

DeBorde, D. C. et al. 1986 Anal. Biochem 157: 275–282.

Auld, V. J. et al. 1990. Proc. Natl. Acad. Sci. 87: 323–327.

Kohara, M. et al. 1986. Virology 151: 21–30.

Saltarelli M. et al, "Nucleotide sequence and nonseriptional analysis of molecular clones of CAEV which generate infectious virus" Virology 179: 347–364 (1990).

*Primary Examiner*—Mary E. Mosher
*Assistant Examiner*—Laurie Scheiner
*Attorney, Agent, or Firm*—John P. White

[57] ABSTRACT

The present invention relates to methods for producing RNA virus cDNA, methods for producing viable, RNA virus and viable, RNA virus produced by those methods. The invention also related to a novel RNA virus cDNA, recombinant DNA molecules containing that cDNA and hosts transformed with those recombinant cDNA molecules. This invention further related to novel methods for screening for variants of a strain 3 poliovirus. This invention also related to methods for increasing the attenuation of a strain poliovirus. This invention provides a vaccine useful for immunizing a subject, for example a human, against infectious poliovirus, wherein the vaccine comprises an effective amount of an RNA virus, produced by transforming a suitable host cell with a recombinant nucleic acid sequence which encodes for the virus: culturing the host cell under conditions which permit the production of virus: and isolating the virus so produced, effective to immunize the subject, and a suitable carrier. Further provided to this invention is a method of immunizing a subject such as a human against infectious poliovirus, wherein the method comprises administering the subject a suitable dose of the vaccine described hereinabove.

2 Claims, 24 Drawing Sheets

FIG. 3
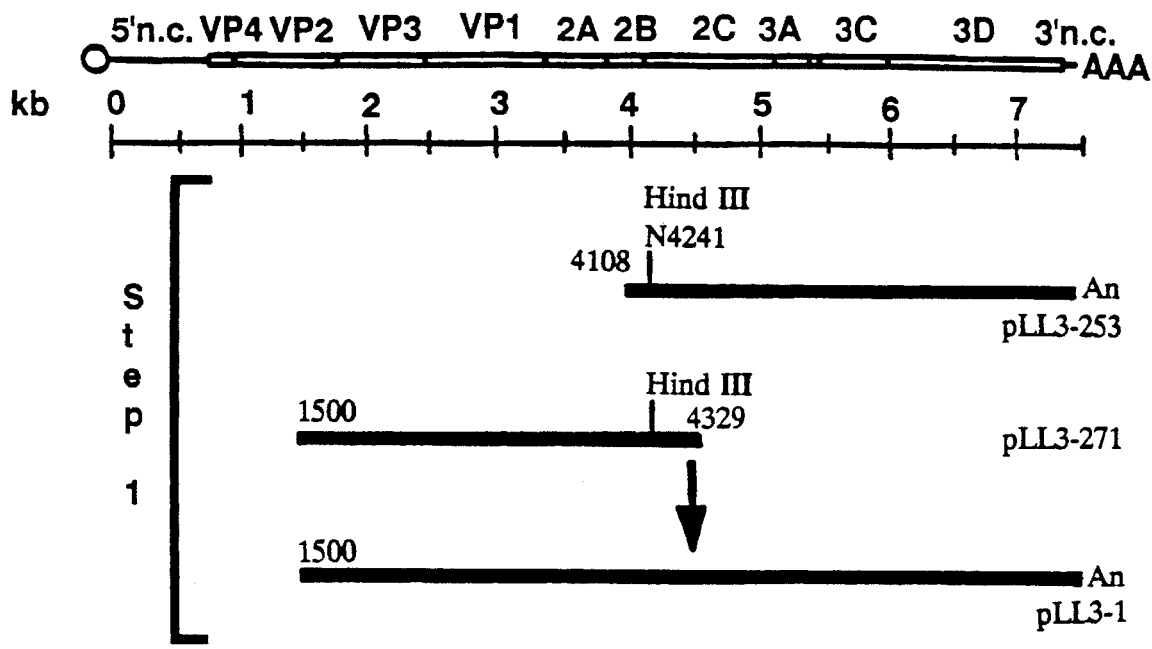
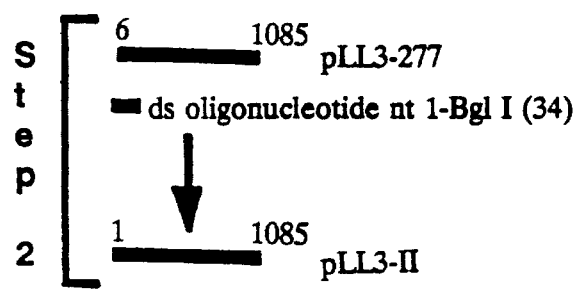
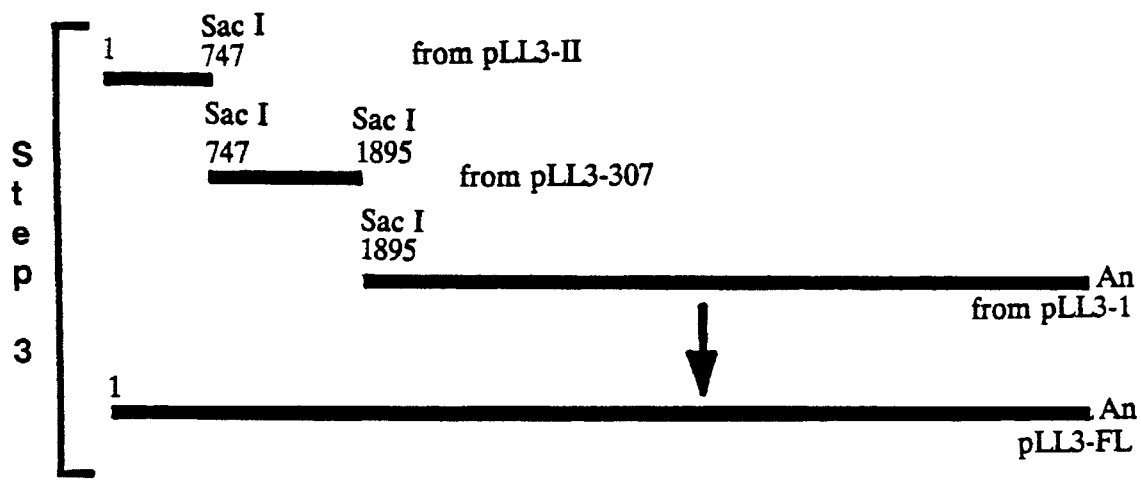

FIG. 6A

```
          10        20        30        40        50        60
     TTAAAACAGCTCTGGGGTTGTTCCCACCCCAGAGGCCCACGTGGCGGCTAGTACACTGGT 70        80        90       100       110       120
     ATCACGGTACCTTTGTACGCCTGTTTTATACTCCCTCCCCGCAACTTAGAAGCATACAA 130       140       150       160       170       180
     TTCAAGCTCAATAGGAGGGGGTGCAAGCCAGCGCCTCCGTGGGCAAGCACTACTGTTTCC 190       200       210       220       230       240
     CCGGTGAGGCCGCATAGACTGTTCCCACGGTTGAAAGTGTCCGATCCGTTATCCGCTCAT 250       260       270       280       290       300
     GTACTTCGAGAAGCCTAGTATCGCTCTGGAATCTTCGACGCGTTGCGCTCAGCACTCAAC 310       320       330       340       350       360
     CCCGGAGTGTAGCTTGGGCCGATGAGTCTGGACAGTCCCCACTGGCGACAGTGGTCCAGG 370       380       390       400       410       420
     CTGCGCTGGCGGCCCACCTGTGGCCCAAAGCCACGGGACGCTAGTTGTGAACAGGGTGTG 430       440       450       460       470       480
     AAGAGCCTATTGAGCTACATGAGAGTCCTCCGGCCCCTGAATGCGGCTAATTCTAACCAT 490       500       510       520       530       540
     GGAGCAGGCAGCTGCAACCCAGCAGCCAGCCTGTCGTAACGCGCAAGTCCGTGGCGGAAC 550       560       570       580       590       600
     CGACTACTTTGGGTGTCCGTGTTTCCTTTTATTCTTGAATGGCTGCTTATGGTGACAATC 610       620       630       640       650       660
     ATAGATTGTTATCATAAAGCGAGTTGGATTGGCCATCCAGTGTGAATCAGATTAATTACT 670       680       690       700       710       720
     CCCTTGTTTGTTGGATCCACTCCCGAAACGTTTTACTCCTTAACTTATTGAAATTGTTTG 730       740       750       760       770       780
     AAGACAGGATTTCAGTGTCACAATGGGAGCTCAAGTATCATCCCAAAAAGTAGGCGCTCA
                                 M   G   A   Q   V   S   S   Q   K   V   G   A   H 790       800       810       820       830       840
     CGAGAATTCTAACCGAGCCTACGGTGGTTCTACGATCAACTACACCACAATTAATTATTA
       E   N   S   N   R   A   Y   G   G   S   T   I   N   Y   T   T   I   N   Y   Y
```

FIG. 6B

```
         850       860       870       880       890       900
TAAAGATTCCGCAAGTAATGCGGCGTCCAAACAAGATTACTCACAGGATCCATCAAAATT
  K  D  S  A  S  N  A  A  S  K  Q  D  Y  S  Q  D  P  S  K  F 910       920       930       940       950       960
CACCGAGCCACTAAAGGACGTGCTCATAAAAACAGCTCCAGCACTCAATTCACCAAATGT
  T  E  P  L  K  D  V  L  I  K  T  A  P  A  L  N  S  P  N  V 970       980       990      1000      1010      1020
GGAAGCGTGTGGGTATAGTGATAGAGTGTTGCAACTCACTTTAGGCAATTCCACTATTAC
  E  A  C  G  Y  S  D  R  V  L  Q  L  T  L  G  N  S  T  I  T 1030      1040      1050      1060      1070      1080
TACACAGGAGGCAGCAAATTCAGTAGTGGCTTACGGACGTTGGCCTGAGTTTATTAGAGA
  T  Q  E  A  A  N  S  V  V  A  Y  G  R  W  P  E  F  I  R  D 1090      1100      1110      1120      1130      1140
TGACGAAGCAAACCCGGTGGACCAACCAACTGAACCAGATGTGGCTACATGCAGATTCTA
  D  E  A  N  P  V  D  Q  P  T  E  P  D  V  A  T  C  R  F  Y 1150      1160      1170      1180      1190      1200
CACACTAGACACTGTAATGTGGGGTAAGGAGTCGAAAGGCTGGTGGTGGAAGTTACCTGA
  T  L  D  T  V  M  W  G  K  E  S  K  G  W  W  W  K  L  P  D 1210      1220      1230      1240      1250      1260
CGCACTGAGAGACATGGGTCTGTTTGGACAAAACATGTATTACCACTACCTAGGAAGATC
  A  L  R  D  M  G  L  F  G  Q  N  M  Y  Y  H  Y  L  G  R  S 1270      1280      1290      1300      1310      1320
CGGGTACACTGTGCACGTGCAGTGTAATGCATCCAAATTTCACCAAGGTGCACTCGGGGT
  G  Y  T  V  H  V  Q  C  N  A  S  K  F  H  Q  G  A  L  G  V 1330      1340      1350      1360      1370      1380
GTTTGCGATTCCTGAGTATTGTCTGGCGGGTGACAGTGACAAGCAAAGGTACACTAGTTA
  F  A  I  P  E  Y  C  L  A  G  D  S  D  K  Q  R  Y  T  S  Y 1390      1400      1410      1420      1430      1440
TGCAAATGCGAATCCAGGTGAAAGAGGGGGAAAATTTTACTCCCAATTCAACAAGGATAA
  A  N  A  N  P  G  E  R  G  G  K  F  Y  S  Q  F  N  K  D  N 1450      1460      1470      1480      1490      1500
CGCAGTAACATCCCCAAAAAGAGAGTTCTGCCCAGTGGATTATCTCCTGGGATGTGGGGT
  A  V  T  S  P  K  R  E  F  C  P  V  D  Y  L  L  G  C  G  V 1510      1520      1530      1540      1550      1560
GTTACTGGGAAATGCCTTTGTATACCCACATCAAATCATTAATCTGAGGACCAACAACAG
  L  L  G  N  A  F  V  Y  P  H  Q  I  I  N  L  R  T  N  N  S
```

FIG. 6C

```
     1570      1580      1590      1600      1610      1620
CGCAACTATTGTCCTACCATATGTGAATGCTTTGGCCATTGATTCAATGGTTAAACACAA
 A  T  I  V  L  P  Y  V  N  A  L  A  I  D  S  M  V  K  H  N 1630      1640      1650      1660      1670      1680
CAACTGGGGCATTGCCATTCTGCCCTTATCACCGCTGGATTTTGCTCAAGATTCATCAGT
 N  W  G  I  A  I  L  P  L  S  P  L  D  F  A  Q  D  S  S  V 1690      1700      1710      1720      1730      1740
TGAAATTCCAATTACTGTGACAATTGCCCCAATGTGTAGCGAGTTCAACGGCCTTCGCAA
 E  I  P  I  T  V  T  I  A  P  M  C  S  E  F  N  G  L  R  N 1750      1760      1770      1780      1790      1800
CGTGACTGCACCTAAATTTCAAGGACTACCAGTGTTAACACTCCTGGTAGTAACCAGTA
 V  T  A  P  K  F  Q  G  L  P  V  L  N  T  P  G  S  N  Q  Y 1810      1820      1830      1840      1850      1860
CCTGACGTCAGACAACCACCAATCACCATGCGCAATCCCAGAATTTGATGTCACTCCGCC
 L  T  S  D  N  H  Q  S  P  C  A  I  P  E  F  D  V  T  P  P 1870      1880      1890      1900      1910      1920
TATTGATATCCCAGGTGAGGTTAAAAACATGATGGAGCTCGCCGAGATAGACACCATGAT
 I  D  I  P  G  E  V  K  N  M  M  E  L  A  E  I  D  T  M  I 1930      1940      1950      1960      1970      1980
TCCTCTCAATTTGGAGAGCACCAAGAGAAACACAATGGACATGTACAGAGTTACTCTGAG
 P  L  N  L  E  S  T  K  R  N  T  M  D  M  Y  R  V  T  L  S 1990      2000      2010      2020      2030      2040
CGACAGTGCCGATCTATCGCAACCAATTTTGTGCTTGTCACTATCCCCAGCATTTGATCC
 D  S  A  D  L  S  Q  P  I  L  C  L  S  L  S  P  A  F  D  P 2050      2060      2070      2080      2090      2100
GCGCTTGTCACACACCATGCTTGGGGAAGTACTGAACTATTATACTCATTGGGCCGGGTC
 R  L  S  H  T  M  L  G  E  V  L  N  Y  Y  T  H  W  A  G  S 2110      2120      2130      2140      2150      2160
CTTGAAATTTACCTTCCTGTTCTGTGGTTCAATGATGGCTACGGGGAAAATCCTAGTGGC
 L  K  F  T  F  L  F  C  G  S  M  M  A  T  G  K  I  L  V  A 2170      2180      2190      2200      2210      2220
CTATGCACCACCAGGTGCACAACCCCCCACCAGCCGTAAGGAGGCTATGTTGGGCACACA
 Y  A  P  P  G  A  Q  P  P  T  S  R  K  E  A  M  L  G  T  H
```

FIG. 6D

```
             2230       2240       2250       2260       2270       2280
      TGTCATTTGGGATCTTGGCCTGCAATCATCTTGTACTATGGTGGTGCCGTGGATTAGTAA
        V  I  W  D  L  G  L  Q  S  S  C  T  M  V  V  P  W  I  S  N 2290       2300       2310       2320       2330       2340
      TGTGACATACAGACAGACTACACAAGATAGTTTCACTGAGGGCGGATATATCAGCATGTT
        V  T  Y  R  Q  T  T  Q  D  S  F  T  E  G  G  Y  I  S  M  F 2350       2360       2370       2380       2390       2400
      CTACCAAACAAGAATTGTGGTGCCACTGTCCACCCCTAAGAGTATGAGCATGCTGGGGTT
        Y  Q  T  R  I  V  V  P  L  S  T  P  K  S  M  S  M  L  G  F 2410       2420       2430       2440       2450       2460
      TGTGTCAGCCTGTAATGATTTCAGTGTGCGATTGCTGCGAGACACCACTCACATTTCACA
        V  S  A  C  N  D  F  S  V  R  L  L  R  D  T  T  H  I  S  Q 2470       2480       2490       2500       2510       2520
      ATCTGCGCTTCCACAGGGTATTGAAGATTTGACTTCTGAAGTTGCACAGGGCGCCCTAAC
        S  A  L  P  Q  G  I  E  D  L  T  S  E  V  A  Q  G  A  L  T 2530       2540       2550       2560       2570       2580
      TTTGTCACTCCCGAAGCAACAGGATAGCTTACCTGATACTAAGGCCAGTGGCCCGGCGCA
        L  S  L  P  K  Q  Q  D  S  L  P  D  T  K  A  S  G  P  A  H 2590       2600       2610       2620       2630       2640
      TTCCAAGGAGGTACCTGCACTCACTGCAGTCGAGACTGGAGCCACCAATCCTCTGGCACC
        S  K  E  V  P  A  L  T  A  V  E  T  G  A  T  N  P  L  A  P 2650       2660       2670       2680       2690       2700
      ATCCGACACAGTTCAAACGCGCCACGTAGTCCAACGACGCAGCAGGTCAGAGTCCACAAT
        S  D  T  V  Q  T  R  H  V  V  Q  R  R  S  R  S  E  S  T  I 2710       2720       2730       2740       2750       2760
      AGAATCATTCTTCGCACGCGGGGCGTGCGTCGCTATTATTGAGGTGGACAATGAACAACC
        E  S  F  F  A  R  G  A  C  V  A  I  I  E  V  D  N  E  Q  P 2770       2780       2790       2800       2810       2820
      AACCACCCGGGCACAGAAACTATTTGCCATGTGGCGCATTACATACAAAGATACAGTGCA
        T  T  R  A  Q  K  L  F  A  M  W  R  I  T  Y  K  D  T  V  Q 2830       2840       2850       2860       2870       2880
      GTTGCGCCGTAAGTTGGAGTTTTTCACATACTCTCGTTTTGACATGGAATTCACCTTCGT
        L  R  R  K  L  E  F  F  T  Y  S  R  F  D  M  E  F  T  F  V
```

FIG. 6E

```
     2890      2900      2910      2920      2930      2940
GGTAACCGCCAACTTCACCAACGCTAATAATGGGCATGCACTCAACCAGGTGTACCAGAT
  V  T  A  N  F  T  N  A  N  N  G  H  A  L  N  Q  V  Y  Q  I 2950      2960      2970      2980      2990      3000
AATGTACATCCCCCCAGGGGCACCCACACCAAAGTCATGGACGACTACACTTGGCAAAC
  M  Y  I  P  P  G  A  P  T  P  K  S  W  D  D  Y  T  W  Q  T 3010      3020      3030      3040      3050      3060
ATCTTCCAACCCGTCCATATTTTACACCTATGGGGCTGCCCCGGCGCGAATCTCAGTGCC
  S  S  N  P  S  I  F  Y  T  Y  G  A  A  P  A  R  I  S  V  P 3070      3080      3090      3100      3110      3120
ATACGTGGGGTTAGCCAATGCTTACTCGCACTTTTACGACGGCTTCGCCAAGGTGCCATT
  Y  V  G  L  A  N  A  Y  S  H  F  Y  D  G  F  A  K  V  P  L 3130      3140      3150      3160      3170      3180
GAAGACAGATGCCAATGACCAGATTGGTGATTCCTTGTACAGCGCCATGACAGTTGATGA
  K  T  D  A  N  D  Q  I  G  D  S  L  Y  S  A  M  T  V  D  D 3190      3200      3210      3220      3230      3240
CTTTGGTGTATTGGCAGTTCGTGTTGTCAATGATCACAACCCCACTAAAGTAACCTCCAA
  F  G  V  L  A  V  R  V  V  N  D  H  N  P  T  K  V  T  S  K 3250      3260      3270      3280      3290      3300
AGTCCGCATTTACATGAAACCCAAACACGTACGTGTCTGGTGCCCTAGACCGCCGCGCGC
  V  R  I  Y  M  K  P  K  H  V  R  V  W  C  P  R  P  P  R  A 3310      3320      3330      3340      3350      3360
GGTACCTTATTATGGACCAGGGGTGGACTATAGGAACAACTTGGACCCCTTATCTGAGAA
  V  P  Y  Y  G  P  G  V  D  Y  R  N  N  L  D  P  L  S  E  K 3370      3380      3390      3400      3410      3420
AGGTTTGACCACATATGGCTTTGGGCATCAGAATAAAGCTGTGTACACTGCTGGTTACAA
  G  L  T  T  Y  G  F  G  H  Q  N  K  A  V  Y  T  A  G  Y  K 3430      3440      3450      3460      3470      3480
GATCTGCAACTACCATCTCGCCACTAAGGAGGATTTACAAAATGCTGTAAGCATCATGTG
  I  C  N  Y  H  L  A  T  K  E  D  L  Q  N  A  V  S  I  M  W 3490      3500      3510      3520      3530      3540
GAATAGAGACCTCTTGGTTGTTGAATCAAAAGCTCAAGGTACCGACTCAATAGCAAGGTG
  N  R  D  L  L  V  V  E  S  K  A  Q  G  T  D  S  I  A  R  C
```

FIG. 6F

```
        3550       3560       3570       3580       3590       3600
CAATTGCAATGCAGGGGTGTACTATTGTGAGTCCAGAAGGAAATACTACCCTGTGTCGTT
  N  C  N  A  G  V  Y  Y  C  E  S  R  R  K  Y  Y  P  V  S  F 3610       3620       3630       3640       3650       3660
TGTGGGACCCACCTTCCAATACATGGAGGCTAATGACTACTACCCAGCTAGATACCAATC
  V  G  P  T  F  Q  Y  M  E  A  N  D  Y  Y  P  A  R  Y  Q  S 3670       3680       3690       3700       3710       3720
CCACATGTTAATCGGGCACGGCTTTGCCTCACCAGGTGACTGTGGTGGTATCCTTAGGTG
  H  M  L  I  G  H  G  F  A  S  P  G  D  C  G  G  I  L  R  C 3730       3740       3750       3760       3770       3780
TCAACATGGCGTCATCGGAATCGTGACAGCTGGTGGAGAGGGATTAGTCGCATTCTCTGA
  Q  H  G  V  I  G  I  V  T  A  G  G  E  G  L  V  A  F  S  D 3790       3800       3810       3820       3830       3840
CATAAGGGACTTGTATGCTTACGAGGAAGAGGCCATGGAGCAGGGCATTTCAAACTATAT
  I  R  D  L  Y  A  Y  E  E  E  A  M  E  Q  G  I  S  N  Y  I 3850       3860       3870       3880       3890       3900
TGAGTCACTCGGTGCTGCGTTCGGTAGTGGGTTCACTCAGCAAATAGGGGATAAGATATC
  E  S  L  G  A  A  F  G  S  G  F  T  Q  Q  I  G  D  K  I  S 3910       3920       3930       3940       3950       3960
AGAACTAACCAGCATGGTGACCAGCACGATTACAGAGAAGCTACTTAAAAACCTAATCAA
  E  L  T  S  M  V  T  S  T  I  T  E  K  L  L  K  N  L  I  K 3970       3980       3990       4000       4010       4020
AATTATTTCATCTCTGGTGATTATCACTAGAAATTACGAAGATACCACCACAGTGCTCGC
  I  I  S  S  L  V  I  I  T  R  N  Y  E  D  T  T  T  V  L  A 4030       4040       4050       4060       4070       4080
CACTCTAGCTCTTCTTGGGTGTGATGTTTCACCGTGGCAATGGCTGAAGAAGAAAGCATG
  T  L  A  L  L  G  C  D  V  S  P  W  Q  W  L  K  K  K  A  C 4090       4100       4110       4120       4130       4140
TGACACTTTGGAGATTCCCTATGTTATTAGACAGGGTGATAGTTGGTTGAAAAAATTTAC
  D  T  L  E  I  P  Y  V  I  R  Q  G  D  S  W  L  K  K  F  T 4150       4160       4170       4180       4190       4200
TGAGGCGTGCAACGCAGCTAAGGGGTTGGAATGGGTGTCCAACAAAATCTCAAAATTTAT
  E  A  C  N  A  A  K  G  L  E  W  V  S  N  K  I  S  K  F  I
```

FIG. 6G

```
        4210        4220        4230        4240        4250        4260
TGACTGGTTGAGAGAAAGAATCATCCCACAAGCCAGGGACAAGCTTGAGTTTGTAACCAA
  D   W   L   R   E   R   I   I   P   Q   A   R   D   K   L   E   F   V   T   K 4270        4280        4290        4300        4310        4320
ATTGAAACAGTTGGAAATGCTAGAGAATCAGATATCCACAATACACCAATCTTGTCCAAG
  L   K   Q   L   E   M   L   E   N   Q   I   S   T   I   H   Q   S   C   P   S 4330        4340        4350        4360        4370        4380
TCAGGAACACCAGGAAATTTTGTTCAACAATGTACGCTGGTTGTCCATTCAATCCAAGAG
  Q   E   H   Q   E   I   L   F   N   N   V   R   W   L   S   I   Q   S   K   R 4390        4400        4410        4420        4430        4440
ATTCGCTCCATTGTACGCACTTGAGGCCAAGAGAATACAAAAGTTGGAACACACCATTAA
  F   A   P   L   Y   A   L   E   A   K   R   I   Q   K   L   E   H   T   I   N 4450        4460        4470        4480        4490        4500
TAATTACATACAGTTCAAGAGCAAACACCGTATTGAGCCAGTATGTTTGTTAGTGCATGG
  N   Y   I   Q   F   K   S   K   H   R   I   E   P   V   C   L   L   V   H   G 4510        4520        4530        4540        4550        4560
GAGCCCAGGTACAGGAAAATCAGTTGCGACTAACCTAATTGCTAGAGCCATAGCTGAGAA
  S   P   G   T   G   K   S   V   A   T   N   L   I   A   R   A   I   A   E   K 4570        4580        4590        4600        4610        4620
AGAGAACACCTCCACCTACTCGCTACCACCGGACCCGTCTCACTTTGATGGATACAAACA
  E   N   T   S   T   Y   S   L   P   P   D   P   S   H   F   D   G   Y   K   Q 4630        4640        4650        4660        4670        4680
ACAAGGTGTGGTTATCATGGACGACCTAAACCAAAACCCGGATGGGGCAGATATGAAGCT
  Q   G   V   V   I   M   D   D   L   N   Q   N   P   D   G   A   D   M   K   L 4690        4700        4710        4720        4730        4740
CTTTTGTCAAATGGTGTCCACTGTGGAGTTTATCCCACCTATGGCCTCGCTGGAAGAGAA
  F   C   Q   M   V   S   T   V   E   F   I   P   P   M   A   S   L   E   E   K 4750        4760        4770        4780        4790        4800
AGGCATTCTGTTCACATCCAACTATGTTTTAGCCTCCACCAACTCCAGTCGCATCACACC
  G   I   L   F   T   S   N   Y   V   L   A   S   T   N   S   S   R   I   T   P 4810        4820        4830        4840        4850        4860
ACCTACAGTAGCCCACAGTGACGCTCTGGCCAGGAGGTTCGCTTTCGATATGGATATTCA
  P   T   V   A   H   S   D   A   L   A   R   R   F   A   F   D   M   D   I   Q
```

FIG. 6H

```
        4870       4880       4890       4900       4910       4920
AGTGATGGGCGAGTACTCCAGAGATGGTAAACTCAACATGGCAATGGCTACTGAGACGTG
  V   M   G   E   Y   S   R   D   G   K   L   N   M   A   M   A   T   E   T   C 4930       4940       4950       4960       4970       4980
CAAGGACTGCCACCAACCAGCAAACTTCAAAAGATGCTGTCCTTTAGTGTGTGGTAAGGC
  K   D   C   H   Q   P   A   N   F   K   R   C   C   P   L   V   C   G   K   A 4990       5000       5010       5020       5030       5040
AATTCAGTTAATGGACAAATCTTCCAGAGTTAGGTACAGTGTTGACCAGATTACTACAAT
  I   Q   L   M   D   K   S   S   R   V   R   Y   S   V   D   Q   I   T   T   M 5050       5060       5070       5080       5090       5100
GATTATCAACGAGAGAAACAGAAGATCTAACATTGGCAATTGCATGGAGGCTTTGTTCCA
  I   I   N   E   R   N   R   R   S   N   I   G   N   C   M   E   A   L   F   Q 5110       5120       5130       5140       5150       5160
AGGACCACTCCAGTACAAAGACCTGAAAATTGACATCAAGACGAGGCCCCCCCCTGAATG
  G   P   L   Q   Y   K   D   L   K   I   D   I   K   T   R   P   P   P   E   C 5170       5180       5190       5200       5210       5220
CATCAATGATCTGCTTCAAGCAGTTGACTCCCAGGAAGTGAGGGATTATTGTGAAAAGAA
  I   N   D   L   L   Q   A   V   D   S   Q   E   V   R   D   Y   C   E   K   K 5230       5240       5250       5260       5270       5280
AGGATGGATCGTCAACATCACTAGCCAAGTTCAAACAGAGAGAAACATTAACCGAGCAAT
  G   W   I   V   N   I   T   S   Q   V   Q   T   E   R   N   I   N   R   A   M 5290       5300       5310       5320       5330       5340
GACCATTTTGCAGGCAGTGACAACTTTCGCCGCAGTGGCTGGTGTCGTGTACGTCATGTA
  T   I   L   Q   A   V   T   T   F   A   A   V   A   G   V   V   Y   V   M   Y 5350       5360       5370       5380       5390       5400
CAAGTTATTCGCTGGACACCAGGGAGCATACACTGGTCTGCCAAACAAAAGACCCAATGT
  K   L   F   A   G   H   Q   G   A   Y   T   G   L   P   N   K   R   P   N   V 5410       5420       5430       5440       5450       5460
GCCCACCATTAGAGCAGCAAAAGTGCAAGGGCCTGGGTTTGACTATGCAGTGGCTATGGC
  P   T   I   R   A   A   K   V   Q   G   P   G   F   D   Y   A   V   A   M   A 5470       5480       5490       5500       5510       5520
TAAAAGAAACATTGTTACAGCAACTACTAGCAAAGGGGAGTTCACAATGCTAGGAGTCCA
  K   R   N   I   V   T   A   T   T   S   K   G   E   F   T   M   L   G   V   H
```

FIG. 6I

```
       5530       5540       5550       5560       5570       5580
CGACAACGTGGCCATTTTACCAACTCATGCCTCACCTGGTGAGAGTATTGTAATTGATGG
  D  N  V  A  I  L  P  T  H  A  S  P  G  E  S  I  V  I  D  G 5590       5600       5610       5620       5630       5640
CAAAGAGGTTGAAATCCTAGACGCTAAAGCCCTCGAAGATCAGGCAGGCACTAATCTGGA
  K  E  V  E  I  L  D  A  K  A  L  E  D  Q  A  G  T  N  L  E 5650       5660       5670       5680       5690       5700
AATCACCATAATAACCCTCAAAAGAAATGAAAAGTTCAGAGATATCAGACAACACATACC
  I  T  I  I  T  L  K  R  N  E  K  F  R  D  I  R  Q  H  I  P 5710       5720       5730       5740       5750       5760
CACTCAAATCACCGAGACGAATGATGGAGTTCTGATTGTAACACTAGTAAGTACCCCAA
  T  Q  I  T  E  T  N  D  G  V  L  I  V  N  T  S  K  Y  P  N 5770       5780       5790       5800       5810       5820
CATGTATGTTCCTGTCGGTGCTGTGACTGAGCAGGGATACCTAAATCTCGGTGGGCGCCA
  M  Y  V  P  V  G  A  V  T  E  Q  G  Y  L  N  L  G  G  R  Q 5830       5840       5850       5860       5870       5880
GACTGCTCGTATTCTAATGTACAACTTTCCAACCAGAGCTGGTCAGTGTGGTGGAGTCAT
  T  A  R  I  L  M  Y  N  F  P  T  R  A  G  Q  C  G  G  V  I 5890       5900       5910       5920       5930       5940
CACATGCACTGGGAAAGTCATCGGGATGCACGTTGGTGGGAATGGTTCACATGGGTTTGC
  T  C  T  G  K  V  I  G  M  H  V  G  G  N  G  S  H  G  F  A 5950       5960       5970       5980       5990       6000
AGCGGCCCTGAAGCGGTCATACTTCACTCAGAGCCAAGGTGAAATCCAGTGGATGAGACC
  A  A  L  K  R  S  Y  F  T  Q  S  Q  G  E  I  Q  W  M  R  P 6010       6020       6030       6040       6050       6060
ATCAAAGGAGGCAGGGTATCCAATTATAAACGCCCCAACCAAGACCAAGCTCGAGCCCAG
  S  K  E  A  G  Y  P  I  I  N  A  P  T  K  T  K  L  E  P  S 6070       6080       6090       6100       6110       6120
TGCTTTCCACTATGTGTTTGAAGGAGTAAAGGAACCAGCAGTCCTCACAAAGAATGATCC
  A  F  H  Y  V  F  E  G  V  K  E  P  A  V  L  T  K  N  D  P 6130       6140       6150       6160       6170       6180
CAGACTCAAAACAGACTTTGAAGAAGCAATCTTCTCTAAGTATGTAGGGAACAAGATCAC
  R  L  K  T  D  F  E  E  A  I  F  S  K  Y  V  G  N  K  I  T
```

FIG. 6J

```
        6190       6200       6210       6220       6230       6240
TGAGGTGGATGAGTACATGAAAGAGGCAGTGGACCATTATGCTGGACAACTTATGTCGCT
 E  V  D  E  Y  M  K  E  A  V  D  H  Y  A  G  Q  L  M  S  L 6250       6260       6270       6280       6290       6300
GGATATCAGCACAGAGCAAATGTGTCTAGAAGACGCCATGTATGGTACTGATGGTCTGGA
 D  I  S  T  E  Q  M  C  L  E  D  A  M  Y  G  T  D  G  L  E 6310       6320       6330       6340       6350       6360
GGCGCTAGATCTGTCTACCAGTGCCGGGTACCCCTACGTGGCAATGGGGAAGAAGAAGAG
 A  L  D  L  S  T  S  A  G  Y  P  Y  V  A  M  G  K  K  K  R 6370       6380       6390       6400       6410       6420
AGATATCCTAAACAAGCAAACCAGAGACACCAAAGAAATGCAAAGACTTTTGGACGCTTA
 D  I  L  N  K  Q  T  R  D  T  K  E  M  Q  R  L  L  D  A  Y 6430       6440       6450       6460       6470       6480
CGGAATCAACCTACCATTAGTGACATATGTCAAGGACGAGCTGAGGTCCAAAACAAAAGT
 G  I  N  L  P  L  V  T  Y  V  K  D  E  L  R  S  K  T  K  V 6490       6500       6510       6520       6530       6540
GGAACAGGGAAAATCCAGACTGATTGAAGCTTCCAGTCTAAATGACTCAGTGGCCATGAG
 E  Q  G  K  S  R  L  I  E  A  S  S  L  N  D  S  V  A  M  R 6550       6560       6570       6580       6590       6600
AATGGCATTTGGAAACCTTTATGCAGCATTCCACAGGAATCCAGGGGTCGTCACTGGTAG
 M  A  F  G  N  L  Y  A  A  F  H  R  N  P  G  V  V  T  G  S 6610       6620       6630       6640       6650       6660
TGCAGTTGGATGCGATCCAGACCTATTCTGGAGCAAGATCCCAGTGTTGATGGAAGAAAA
 A  V  G  C  D  P  D  L  F  W  S  K  I  P  V  L  M  E  E  K 6670       6680       6690       6700       6710       6720
GCTATTTGCCTTTGATTACACAGGATACGACGCATCACTTAGCCCAGCTTGGTTTGAGGC
 L  F  A  F  D  Y  T  G  Y  D  A  S  L  S  P  A  W  F  E  A 6730       6740       6750       6760       6770       6780
ACTCAAGATGGTGTTAGAGAAAATTGGTTTTGGAGATAGAGTGGATTACATAGACTACCT
 L  K  M  V  L  E  K  I  G  F  G  D  R  V  D  Y  I  D  Y  L 6790       6800       6810       6820       6830       6840
TAACCATTCACACCACTTGTACAAAAACAAGATATATTGTGTTAAGGGCGGCATGCCATC
 N  H  S  H  H  L  Y  K  N  K  I  Y  C  V  K  G  G  M  P  S
```

FIG. 6K

```
      6850       6860       6870       6880       6890       6900
TGGCTGCTCCGGCACTTCAATTTTTAATTCAATGATTAACAATTTGATCATTAGGACGCT
  G  C  S  G  T  S  I  F  N  S  M  I  N  N  L  I  I  R  T  L 6910       6920       6930       6940       6950       6960
TTTACTGAAAACCTACAAGGGCATAGATTTGGACCACTTAAAAATGATTGCCTATGGTGA
  L  L  K  T  Y  K  G  I  D  L  D  H  L  K  M  I  A  Y  G  D 6970       6980       6990       7000       7010       7020
CGATGTAATAGCTTCCTATCCCCATGAGGTTGACGCTAGTCTCCTAGCCCAATCAGGAAA
  D  V  I  A  S  Y  P  H  E  V  D  A  S  L  L  A  Q  S  G  K 7030       7040       7050       7060       7070       7080
AGACTATGGACTAACCATGACTCCGGCAGATAAATCTGCCACTTTTGAGACAGTCACATG
  D  Y  G  L  T  M  T  P  A  D  K  S  A  T  F  E  T  V  T  W 7090       7100       7110       7120       7130       7140
GGAGAATGTAACTTTCTTGAAAAGATTCTTCAGAGCAGATGAGAAATACCCCTTCCTCAT
  E  N  V  T  F  L  K  R  F  F  R  A  D  E  K  Y  P  F  L  I 7150       7160       7170       7180       7190       7200
ACATCCAGTAATGCCAATGAAGGAAATTCATGAATCAATCAGATGGACAAAAGATCCTCG
  H  P  V  M  P  M  K  E  I  H  E  S  I  R  W  T  K  D  P  R 7210       7220       7230       7240       7250       7260
GAATACGCAGGACCATGTACGCTCCTTGTGTCTATTGGCTTGGCACAACGGGGAAGAAGA
  N  T  Q  D  H  V  R  S  L  C  L  L  A  W  H  N  G  E  E  E 7270       7280       7290       7300       7310       7320
ATACAACAAATTTTTAGCTAAAATTAGGAGTGTGCCAATCGGAAGAGCTTTGTTGCTCCC
  Y  N  K  F  L  A  K  I  R  S  V  P  I  G  R  A  L  L  P 7330       7340       7350       7360       7370       7380
AGAGTACTCAACATTGTACCGCCGTTGGCTTGACTCATTTTAGTAACCCTACCTCAGTCG
  E  Y  S  T  L  Y  R  R  W  L  D  S  F  .  .

7390       7400       7410       7420       7430       7440
AATTGGATTGGGTCATACTGTTGTAGGGGTAAATTTTTCTTTAATTCGGAGG
```

5,525,715

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 7432 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 743..7361

( x i ) SEQUENCE DESCRIPTION: SEQ ID NO:1:

```
TTAAAACAGC TCTGGGGTTG TTCCCACCCC AGAGGCCCAC GTGGCGGCTA GTACACTGGT      60
ATCACGGTAC CTTTGTACGC CTGTTTTATA CTCCCTCCCC CGCAACTTAG AAGCATACAA     120
TTCAAGCTCA ATAGGAGGGG GTGCAAGCCA GCGCCTCCGT GGGCAAGCAC TACTGTTTCC     180
CCGGTGAGGC CGCATAGACT GTTCCCACGG TTGAAAGTGT CCGATCCGTT ATCCGCTCAT     240
GTACTTCGAG AAGCCTAGTA TCGCTCTGGA ATCTTCGACG CGTTGCGCTC AGCACTCAAC     300
CCCGGAGTGT AGCTTGGGCC GATGAGTCTG GACAGTCCCC ACTGGCGACA GTGGTCCAGG     360
CTGCGCTGGC GGCCCACCTG TGGCCCAAAG CCACGGGACG CTAGTTGTGA ACAGGGTGTG     420
AAGAGCCTAT TGAGCTACAT GAGAGTCCTC CGGCCCCTGA ATGCGGCTAA TTCTAACCAT     480
GGAGCAGGCA GCTGCAACCC AGCAGCCAGC CTGTCGTAAC GCGCAAGTCC GTGGCGGAAC     540
CGACTACTTT GGGTGTCCGT GTTTCCTTTT ATTCTTGAAT GGCTGCTTAT GGTGACAATC     600
ATAGATTGTT ATCATAAAGC GAGTTGGATT GGCCATCCAG TGTGAATCAG ATTAATTACT     660
CCCTTGTTTG TTGGATCCAC TCCCGAAACG TTTTACTCCT TAACTTATTG AAATTGTTTG     720
AAGACAGGAT TTCAGTGTCA CA ATG GGA GCT CAA GTA TCA TCC CAA AAA GTA     772
                          Met Gly Ala Gln Val Ser Ser Gln Lys Val
                           1               5                  10

GGC GCT CAC GAG AAT TCT AAC CGA GCC TAC GGT GGT TCT ACG ATC AAC      820
Gly Ala His Glu Asn Ser Asn Arg Ala Tyr Gly Gly Ser Thr Ile Asn
                 15                  20                  25

TAC ACC ACA ATT AAT TAT TAT AAA GAT TCC GCA AGT AAT GCG GCG TCC      868
Tyr Thr Thr Ile Asn Tyr Tyr Lys Asp Ser Ala Ser Asn Ala Ala Ser
             30                  35                  40

AAA CAA GAT TAC TCA CAG GAT CCA TCA AAA TTC ACC GAG CCA CTA AAG      916
Lys Gln Asp Tyr Ser Gln Asp Pro Ser Lys Phe Thr Glu Pro Leu Lys
             45                  50                  55

GAC GTG CTC ATA AAA ACA GCT CCA GCA CTC AAT TCA CCA AAT GTG GAA      964
Asp Val Leu Ile Lys Thr Ala Pro Ala Leu Asn Ser Pro Asn Val Glu
         60                  65                  70

GCG TGT GGG TAT AGT GAT AGA GTG TTG CAA CTC ACT TTA GGC AAT TCC     1012
Ala Cys Gly Tyr Ser Asp Arg Val Leu Gln Leu Thr Leu Gly Asn Ser
 75                  80                  85                  90

ACT ATT ACT ACA CAG GAG GCA GCA AAT TCA GTA GTG GCT TAC GGA CGT     1060
Thr Ile Thr Thr Gln Glu Ala Ala Asn Ser Val Val Ala Tyr Gly Arg
                 95                 100                 105
```

| | | | | | | | | | | | | | | | | |
|---|---|---|---|---|---|---|---|---|---|---|---|---|---|---|---|---|
| TGG | CCT | GAG | TTT | ATT | AGA | GAT | GAC | GAA | GCA | AAC | CCG | GTG | GAC | CAA | CCA | 1108 |
| Trp | Pro | Glu | Phe 110 | Ile | Arg | Asp | Asp | Glu 115 | Ala | Asn | Pro | Val | Asp 120 | Gln | Pro | |
| ACT | GAA | CCA | GAT | GTG | GCT | ACA | TGC | AGA | TTC | TAC | ACA | CTA | GAC | ACT | GTA | 1156 |
| Thr | Glu | Pro 125 | Asp | Val | Ala | Thr | Cys 130 | Arg | Phe | Tyr | Thr | Leu 135 | Asp | Thr | Val | |
| ATG | TGG | GGT | AAG | GAG | TCG | AAA | GGC | TGG | TGG | TGG | AAG | TTA | CCT | GAC | GCA | 1204 |
| Met | Trp 140 | Gly | Lys | Glu | Ser | Lys 145 | Gly | Trp | Trp | Trp | Lys 150 | Leu | Pro | Asp | Ala | |
| CTG | AGA | GAC | ATG | GGT | CTG | TTT | GGA | CAA | AAC | ATG | TAT | TAC | CAC | TAC | CTA | 1252 |
| Leu 155 | Arg | Asp | Met | Gly 160 | Leu | Phe | Gly | Gln | Asn 165 | Met | Tyr | Tyr | His | Tyr 170 | Leu | |
| GGA | AGA | TCC | GGG | TAC | ACT | GTG | CAC | GTG | CAG | TGT | AAT | GCA | TCC | AAA | TTT | 1300 |
| Gly | Arg | Ser | Gly | Tyr 175 | Thr | Val | His | Val | Gln 180 | Cys | Asn | Ala | Ser | Lys 185 | Phe | |
| CAC | CAA | GGT | GCA | CTC | GGG | GTG | TTT | GCG | ATT | CCT | GAG | TAT | TGT | CTG | GCG | 1348 |
| His | Gln | Gly | Ala 190 | Leu | Gly | Val | Phe | Ala 195 | Ile | Pro | Glu | Tyr | Cys 200 | Leu | Ala | |
| GGT | GAC | AGT | GAC | AAG | CAA | AGG | TAC | ACT | AGT | TAT | GCA | AAT | GCG | AAT | CCA | 1396 |
| Gly | Asp | Ser 205 | Asp | Lys | Gln | Arg | Tyr 210 | Thr | Ser | Tyr | Ala | Asn 215 | Ala | Asn | Pro | |
| GGT | GAA | AGA | GGG | GGA | AAA | TTT | TAC | TCC | CAA | TTC | AAC | AAG | GAT | AAC | GCA | 1444 |
| Gly | Glu | Arg 220 | Gly | Gly | Lys | Phe | Tyr 225 | Ser | Gln | Phe | Asn | Lys 230 | Asp | Asn | Ala | |
| GTA | ACA | TCC | CCA | AAA | AGA | GAG | TTC | TGC | CCA | GTG | GAT | TAT | CTC | CTG | GGA | 1492 |
| Val | Thr 235 | Ser | Pro | Lys | Arg 240 | Glu | Phe | Cys | Pro | Val 245 | Asp | Tyr | Leu | Leu 250 | Gly | |
| TGT | GGG | GTG | TTA | CTG | GGA | AAT | GCC | TTT | GTA | TAC | CCA | CAT | CAA | ATC | ATT | 1540 |
| Cys | Gly | Val | Leu 255 | Leu | Gly | Asn | Ala | Phe 260 | Val | Tyr | Pro | His | Gln 265 | Ile | Ile | |
| AAT | CTG | AGG | ACC | AAC | AAC | AGC | GCA | ACT | ATT | GTC | CTA | CCA | TAT | GTG | AAT | 1588 |
| Asn | Leu | Arg | Thr 270 | Asn | Asn | Ser | Ala | Thr 275 | Ile | Val | Leu | Pro | Tyr 280 | Val | Asn | |
| GCT | TTG | GCC | ATT | GAT | TCA | ATG | GTT | AAA | CAC | AAC | AAC | TGG | GGC | ATT | GCC | 1636 |
| Ala | Leu | Ala 285 | Ile | Asp | Ser | Met | Val 290 | Lys | His | Asn | Asn | Trp 295 | Gly | Ile | Ala | |
| ATT | CTG | CCC | TTA | TCA | CCG | CTG | GAT | TTT | GCT | CAA | GAT | TCA | TCA | GTT | GAA | 1684 |
| Ile | Leu | Pro 300 | Leu | Ser | Pro | Leu | Asp 305 | Phe | Ala | Gln | Asp | Ser 310 | Ser | Val | Glu | |
| ATT | CCA | ATT | ACT | GTG | ACA | ATT | GCC | CCA | ATG | TGT | AGC | GAG | TTC | AAC | GGC | 1732 |
| Ile | Pro 315 | Ile | Thr | Val | Thr 320 | Ile | Ala | Pro | Met | Cys 325 | Ser | Glu | Phe | Asn | Gly 330 | |
| CTT | CGC | AAC | GTG | ACT | GCA | CCT | AAA | TTT | CAA | GGA | CTA | CCA | GTG | TTG | AAC | 1780 |
| Leu | Arg | Asn | Val | Thr 335 | Ala | Pro | Lys | Phe | Gln 340 | Gly | Leu | Pro | Val | Leu 345 | Asn | |
| ACT | CCT | GGT | AGT | AAC | CAG | TAC | CTG | ACG | TCA | GAC | AAC | CAC | CAA | TCA | CCA | 1828 |
| Thr | Pro | Gly | Ser 350 | Asn | Gln | Tyr | Leu | Thr 355 | Ser | Asp | Asn | His | Gln 360 | Ser | Pro | |
| TGC | GCA | ATC | CCA | GAA | TTT | GAT | GTC | ACT | CCG | CCT | ATT | GAT | ATC | CCA | GGT | 1876 |
| Cys | Ala | Ile 365 | Pro | Glu | Phe | Asp | Val 370 | Thr | Pro | Pro | Ile | Asp 375 | Ile | Pro | Gly | |
| GAG | GTT | AAA | AAC | ATG | ATG | GAG | CTC | GCC | GAG | ATA | GAC | ACC | ATG | ATT | CCT | 1924 |
| Glu | Val | Lys 380 | Asn | Met | Met | Glu 385 | Leu | Ala | Glu | Ile | Asp 390 | Thr | Met | Ile | Pro | |
| CTC | AAT | TTG | GAG | AGC | ACC | AAG | AGA | AAC | ACA | ATG | GAC | ATG | TAC | AGA | GTT | 1972 |
| Leu | Asn | Leu | Glu | Ser 400 | Thr | Lys | Arg | Asn | Thr 405 | Met | Asp | Met | Tyr | Arg 410 | Val | |
| ACT | CTG | AGC | GAC | AGT | GCC | GAT | CTA | TCG | CAA | CCA | ATT | TTG | TGC | TTG | TCA | 2020 |
| Thr | Leu | Ser | Asp | Ser 415 | Ala | Asp | Leu | Ser | Gln 420 | Pro | Ile | Leu | Cys | Leu 425 | Ser | |

| | | | | | | | | | | | | | | | | |
|---|---|---|---|---|---|---|---|---|---|---|---|---|---|---|---|---|
| CTA | TCC | CCA | GCA | TTT | GAT | CCG | CGC | TTG | TCA | CAC | ACC | ATG | CTT | GGG | GAA | 2068 |
| Leu | Ser | Pro | Ala | Phe | Asp | Pro | Arg | Leu | Ser | His | Thr | Met | Leu | Gly | Glu | |
| | | | 430 | | | | 435 | | | | | | 440 | | | |
| GTA | CTG | AAC | TAT | TAT | ACT | CAT | TGG | GCC | GGG | TCC | TTG | AAA | TTT | ACC | TTC | 2116 |
| Val | Leu | Asn | Tyr | Tyr | Thr | His | Trp | Ala | Gly | Ser | Leu | Lys | Phe | Thr | Phe | |
| | | 445 | | | | | 450 | | | | | 455 | | | | |
| CTG | TTC | TGT | GGT | TCA | ATG | ATG | GCT | ACG | GGG | AAA | ATC | CTA | GTG | GCC | TAT | 2164 |
| Leu | Phe | Cys | Gly | Ser | Met | Met | Ala | Thr | Gly | Lys | Ile | Leu | Val | Ala | Tyr | |
| | 460 | | | | | 465 | | | | | 470 | | | | | |
| GCA | CCA | CCA | GGT | GCA | CAA | CCC | CCC | ACC | AGC | CGT | AAG | GAG | GCT | ATG | TTG | 2212 |
| Ala | Pro | Pro | Gly | Ala | Gln | Pro | Pro | Thr | Ser | Arg | Lys | Glu | Ala | Met | Leu | |
| 475 | | | | 480 | | | | | 485 | | | | | | 490 | |
| GGC | ACA | CAT | GTC | ATT | TGG | GAT | CTT | GGC | CTG | CAA | TCA | TCT | TGT | ACT | ATG | 2260 |
| Gly | Thr | His | Val | Ile | Trp | Asp | Leu | Gly | Leu | Gln | Ser | Ser | Cys | Thr | Met | |
| | | | | 495 | | | | | 500 | | | | | 505 | | |
| GTG | GTG | CCG | TGG | ATT | AGT | AAT | GTG | ACA | TAC | AGA | CAG | ACT | ACA | CAA | GAT | 2308 |
| Val | Val | Pro | Trp | Ile | Ser | Asn | Val | Thr | Tyr | Arg | Gln | Thr | Thr | Gln | Asp | |
| | | | 510 | | | | | 515 | | | | | 520 | | | |
| AGT | TTC | ACT | GAG | GGC | GGA | TAT | ATC | AGC | ATG | TTC | TAC | CAA | ACA | AGA | ATT | 2356 |
| Ser | Phe | Thr | Glu | Gly | Gly | Tyr | Ile | Ser | Met | Phe | Tyr | Gln | Thr | Arg | Ile | |
| | | 525 | | | | | 530 | | | | | 535 | | | | |
| GTG | GTG | CCA | CTG | TCC | ACC | CCT | AAG | AGT | ATG | AGC | ATG | CTG | GGG | TTT | GTG | 2404 |
| Val | Val | Pro | Leu | Ser | Thr | Pro | Lys | Ser | Met | Ser | Met | Leu | Gly | Phe | Val | |
| | 540 | | | | | 545 | | | | | 550 | | | | | |
| TCA | GCC | TGT | AAT | GAT | TTC | AGT | GTG | CGA | TTG | CTG | CGA | GAC | ACC | ACT | CAC | 2452 |
| Ser | Ala | Cys | Asn | Asp | Phe | Ser | Val | Arg | Leu | Leu | Arg | Asp | Thr | Thr | His | |
| 555 | | | | | 560 | | | | | 565 | | | | | 570 | |
| ATT | TCA | CAA | TCT | GCG | CTT | CCA | CAG | GGT | ATT | GAA | GAT | TTG | ACT | TCT | GAA | 2500 |
| Ile | Ser | Gln | Ser | Ala | Leu | Pro | Gln | Gly | Ile | Glu | Asp | Leu | Thr | Ser | Glu | |
| | | | | 575 | | | | | 580 | | | | | 585 | | |
| GTT | GCA | CAG | GGC | GCC | CTA | ACT | TTG | TCA | CTC | CCG | AAG | CAA | CAG | GAT | AGC | 2548 |
| Val | Ala | Gln | Gly | Ala | Leu | Thr | Leu | Ser | Leu | Pro | Lys | Gln | Gln | Asp | Ser | |
| | | | 590 | | | | | 595 | | | | | 600 | | | |
| TTA | CCT | GAT | ACT | AAG | GCC | AGT | GGC | CCG | GCG | CAT | TCC | AAG | GAG | GTA | CCT | 2596 |
| Leu | Pro | Asp | Thr | Lys | Ala | Ser | Gly | Pro | Ala | His | Ser | Lys | Glu | Val | Pro | |
| | | 605 | | | | | 610 | | | | | 615 | | | | |
| GCA | CTC | ACT | GCA | GTC | GAG | ACT | GGA | GCC | ACC | AAT | CCT | CTG | GCA | CCA | TCC | 2644 |
| Ala | Leu | Thr | Ala | Val | Glu | Thr | Gly | Ala | Thr | Asn | Pro | Leu | Ala | Pro | Ser | |
| | 620 | | | | | 625 | | | | | 630 | | | | | |
| GAC | ACA | GTT | CAA | ACG | CGC | CAC | GTA | GTC | CAA | CGA | CGC | AGC | AGG | TCA | GAG | 2692 |
| Asp | Thr | Val | Gln | Thr | Arg | His | Val | Val | Gln | Arg | Arg | Ser | Arg | Ser | Glu | |
| 635 | | | | | 640 | | | | | 645 | | | | | 650 | |
| TCC | ACA | ATA | GAA | TCA | TTC | TTC | GCA | CGC | GGG | GCG | TGC | GTC | GCT | ATT | ATT | 2740 |
| Ser | Thr | Ile | Glu | Ser | Phe | Phe | Ala | Arg | Gly | Ala | Cys | Val | Ala | Ile | Ile | |
| | | | | 655 | | | | | 660 | | | | | 665 | | |
| GAG | GTG | GAC | AAT | GAA | CAA | CCA | ACC | ACC | CGG | GCA | CAG | AAA | CTA | TTT | GCC | 2788 |
| Glu | Val | Asp | Asn | Glu | Gln | Pro | Thr | Thr | Arg | Ala | Gln | Lys | Leu | Phe | Ala | |
| | | | 670 | | | | | 675 | | | | | 680 | | | |
| ATG | TGG | CGC | ATT | ACA | TAC | AAA | GAT | ACA | GTG | CAG | TTG | CGC | CGT | AAG | TTG | 2836 |
| Met | Trp | Arg | Ile | Thr | Tyr | Lys | Asp | Thr | Val | Gln | Leu | Arg | Arg | Lys | Leu | |
| | | 685 | | | | | 690 | | | | | 695 | | | | |
| GAG | TTT | TTC | ACA | TAC | TCT | CGT | TTT | GAC | ATG | GAA | TTC | ACC | TTC | GTG | GTA | 2884 |
| Glu | Phe | Phe | Thr | Tyr | Ser | Arg | Phe | Asp | Met | Glu | Phe | Thr | Phe | Val | Val | |
| | 700 | | | | | 705 | | | | | 710 | | | | | |
| ACC | GCC | AAC | TTC | ACC | AAC | GCT | AAT | AAT | GGG | CAT | GCA | CTC | AAC | CAG | GTG | 2932 |
| Thr | Ala | Asn | Phe | Thr | Asn | Ala | Asn | Asn | Gly | His | Ala | Leu | Asn | Gln | Val | |
| 715 | | | | | 720 | | | | | 725 | | | | | 730 | |
| TAC | CAG | ATA | ATG | TAC | ATC | CCC | CCA | GGG | GCA | CCC | ACA | CCA | AAG | TCA | TGG | 2980 |
| Tyr | Gln | Ile | Met | Tyr | Ile | Pro | Pro | Gly | Ala | Pro | Thr | Pro | Lys | Ser | Trp | |
| | | | | 735 | | | | | 740 | | | | | 745 | | |

| | | | | | | | | | | | | | | | | |
|---|---|---|---|---|---|---|---|---|---|---|---|---|---|---|---|---|
| GAC | GAC | TAC | ACT | TGG | CAA | ACA | TCT | TCC | AAC | CCG | TCC | ATA | TTT | TAC | ACC | 3028 |
| Asp | Asp | Tyr | Thr 750 | Trp | Gln | Thr | Ser | Ser 755 | Asn | Pro | Ser | Ile | Phe 760 | Tyr | Thr | |
| TAT | GGG | GCT | GCC | CCG | GCG | CGA | ATC | TCA | GTG | CCA | TAC | GTG | GGG | TTA | GCC | 3076 |
| Tyr | Gly | Ala 765 | Ala | Pro | Ala | Arg | Ile 770 | Ser | Val | Pro | Tyr | Val 775 | Gly | Leu | Ala | |
| AAT | GCT | TAC | TCG | CAC | TTT | TAC | GAC | GGC | TTC | GCC | AAG | GTG | CCA | TTG | AAG | 3124 |
| Asn | Ala 780 | Tyr | Ser | His | Phe | Tyr 785 | Asp | Gly | Phe | Ala | Lys 790 | Val | Pro | Leu | Lys | |
| ACA | GAT | GCC | AAT | GAC | CAG | ATT | GGT | GAT | TCC | TTG | TAC | AGC | GCC | ATG | ACA | 3172 |
| Thr 795 | Asp | Ala | Asn | Asp | Gln 800 | Ile | Gly | Asp | Ser | Leu 805 | Tyr | Ser | Ala | Met | Thr 810 | |
| GTT | GAT | GAC | TTT | GGT | GTA | TTG | GCA | GTT | CGT | GTT | GTC | AAT | GAT | CAC | AAC | 3220 |
| Val | Asp | Asp | Phe | Gly 815 | Val | Leu | Ala | Val | Arg 820 | Val | Val | Asn | Asp | His 825 | Asn | |
| CCC | ACT | AAA | GTA | ACC | TCC | AAA | GTC | CGC | ATT | TAC | ATG | AAA | CCC | AAA | CAC | 3268 |
| Pro | Thr | Lys | Val 830 | Thr | Ser | Lys | Val | Arg 835 | Ile | Tyr | Met | Lys | Pro 840 | Lys | His | |
| GTA | CGT | GTC | TGG | TGC | CCT | AGA | CCG | CCG | CGC | GCG | GTA | CCT | TAT | TAT | GGA | 3316 |
| Val | Arg | Val 845 | Trp | Cys | Pro | Arg | Pro 850 | Pro | Arg | Ala | Val | Pro 855 | Tyr | Tyr | Gly | |
| CCA | GGG | GTG | GAC | TAT | AGG | AAC | AAC | TTG | GAC | CCC | TTA | TCT | GAG | AAA | GGT | 3364 |
| Pro | Gly | Val 860 | Asp | Tyr | Arg | Asn | Asn 865 | Leu | Asp | Pro | Leu | Ser 870 | Glu | Lys | Gly | |
| TTG | ACC | ACA | TAT | GGC | TTT | GGG | CAT | CAG | AAT | AAA | GCT | GTG | TAC | ACT | GCT | 3412 |
| Leu | Thr 875 | Thr | Tyr | Gly | Phe 880 | Gly | His | Gln | Asn | Lys 885 | Ala | Val | Tyr | Thr | Ala 890 | |
| GGT | TAC | AAG | ATC | TGC | AAC | TAC | CAT | CTC | GCC | ACT | AAG | GAG | GAT | TTA | CAA | 3460 |
| Gly | Tyr | Lys | Ile | Cys 895 | Asn | Tyr | His | Leu | Ala 900 | Thr | Lys | Glu | Asp | Leu 905 | Gln | |
| AAT | GCT | GTA | AGC | ATC | ATG | TGG | AAT | AGA | GAC | CTC | TTG | GTT | GTT | GAA | TCA | 3508 |
| Asn | Ala | Val | Ser 910 | Ile | Met | Trp | Asn | Arg 915 | Asp | Leu | Leu | Val | Val 920 | Glu | Ser | |
| AAA | GCT | CAA | GGT | ACC | GAC | TCA | ATA | GCA | AGG | TGC | AAT | TGC | AAT | GCA | GGG | 3556 |
| Lys | Ala | Gln | Gly 925 | Thr | Asp | Ser | Ile | Ala 930 | Arg | Cys | Asn | Cys | Asn 935 | Ala | Gly | |
| GTG | TAC | TAT | TGT | GAG | TCC | AGA | AGG | AAA | TAC | TAC | CCT | GTG | TCG | TTT | GTG | 3604 |
| Val | Tyr | Tyr 940 | Cys | Glu | Ser | Arg | Arg 945 | Lys | Tyr | Tyr | Pro | Val 950 | Ser | Phe | Val | |
| GGA | CCC | ACC | TTC | CAA | TAC | ATG | GAG | GCT | AAT | GAC | TAC | TAC | CCA | GCT | AGA | 3652 |
| Gly | Pro | Thr 955 | Phe | Gln | Tyr | Met | Glu 960 | Ala | Asn | Asp | Tyr | Tyr 965 | Pro | Ala | Arg 970 | |
| TAC | CAA | TCC | CAC | ATG | TTA | ATC | GGG | CAC | GGC | TTT | GCC | TCA | CCA | GGT | GAC | 3700 |
| Tyr | Gln | Ser | His | Met 975 | Leu | Ile | Gly | His | Gly 980 | Phe | Ala | Ser | Pro | Gly 985 | Asp | |
| TGT | GGT | GGT | ATC | CTT | AGG | TGT | CAA | CAT | GGC | GTC | ATC | GGA | ATC | GTG | ACA | 3748 |
| Cys | Gly | Gly | Ile 990 | Leu | Arg | Cys | Gln | His 995 | Gly | Val | Ile | Gly | Ile 1000 | Val | Thr | |
| GCT | GGT | GGA | GAG | GGA | TTA | GTC | GCA | TTC | TCT | GAC | ATA | AGG | GAC | TTG | TAT | 3796 |
| Ala | Gly | Gly | Glu 1005 | Gly | Leu | Val | Ala | Phe 1010 | Ser | Asp | Ile | Arg | Asp 1015 | Leu | Tyr | |
| GCT | TAC | GAG | GAA | GAG | GCC | ATG | GAG | CAG | GGC | ATT | TCA | AAC | TAT | ATT | GAG | 3844 |
| Ala | Tyr | Glu 1020 | Glu | Glu | Ala | Met | Glu 1025 | Gln | Gly | Ile | Ser | Asn 1030 | Tyr | Ile | Glu | |
| TCA | CTC | GGT | GCT | GCG | TTC | GGT | AGT | GGG | TTC | ACT | CAG | CAA | ATA | GGG | GAT | 3892 |
| Ser | Leu | Gly 1035 | Ala | Ala | Phe | Gly | Ser 1040 | Gly | Phe | Thr | Gln | Gln 1045 | Ile | Gly | Asp 1050 | |
| AAG | ATA | TCA | GAA | CTA | ACC | AGC | ATG | GTG | ACC | AGC | ACG | ATT | ACA | GAG | AAG | 3940 |
| Lys | Ile | Ser | Glu | Leu 1055 | Thr | Ser | Met | Val | Thr 1060 | Ser | Thr | Ile | Thr 1065 | Glu | Lys | |

```
CTA CTT AAA AAC CTA ATC AAA ATT ATT TCA TCT CTG GTG ATT ATC ACT     3988
Leu Leu Lys Asn Leu Ile Lys Ile Ile Ser Ser Leu Val Ile Ile Thr
            1070            1075                1080

AGA AAT TAC GAA GAT ACC ACC ACA GTG CTC GCC ACT CTA GCT CTT CTT     4036
Arg Asn Tyr Glu Asp Thr Thr Thr Val Leu Ala Thr Leu Ala Leu Leu
            1085            1090                1095

GGG TGT GAT GTT TCA CCG TGG CAA TGG CTG AAG AAG AAA GCA TGT GAC     4084
Gly Cys Asp Val Ser Pro Trp Gln Trp Leu Lys Lys Lys Ala Cys Asp
        1100            1105                1110

ACT TTG GAG ATT CCC TAT GTT ATT AGA CAG GGT GAT AGT TGG TTG AAA     4132
Thr Leu Glu Ile Pro Tyr Val Ile Arg Gln Gly Asp Ser Trp Leu Lys
1115                1120            1125                1130

AAA TTT ACT GAG GCG TGC AAC GCA GCT AAG GGG TTG GAA TGG GTG TCC     4180
Lys Phe Thr Glu Ala Cys Asn Ala Ala Lys Gly Leu Glu Trp Val Ser
                1135            1140                1145

AAC AAA ATC TCA AAA TTT ATT GAC TGG TTG AGA GAA AGA ATC ATC CCA     4228
Asn Lys Ile Ser Lys Phe Ile Asp Trp Leu Arg Glu Arg Ile Ile Pro
            1150            1155                1160

CAA GCC AGG GAC AAG CTT GAG TTT GTA ACC AAA TTG AAA CAG TTG GAA     4276
Gln Ala Arg Asp Lys Leu Glu Phe Val Thr Lys Leu Lys Gln Leu Glu
            1165            1170                1175

ATG CTA GAG AAT CAG ATA TCC ACA ATA CAC CAA TCT TGT CCA AGT CAG     4324
Met Leu Glu Asn Gln Ile Ser Thr Ile His Gln Ser Cys Pro Ser Gln
        1180            1185                1190

GAA CAC CAG GAA ATT TTG TTC AAC AAT GTA CGC TGG TTG TCC ATT CAA     4372
Glu His Gln Glu Ile Leu Phe Asn Asn Val Arg Trp Leu Ser Ile Gln
1195                1200            1205                1210

TCC AAG AGA TTC GCT CCA TTG TAC GCA CTT GAG GCC AAG AGA ATA CAA     4420
Ser Lys Arg Phe Ala Pro Leu Tyr Ala Leu Glu Ala Lys Arg Ile Gln
                1215            1220                1225

AAG TTG GAA CAC ACC ATT AAT AAT TAC ATA CAG TTC AAG AGC AAA CAC     4468
Lys Leu Glu His Thr Ile Asn Asn Tyr Ile Gln Phe Lys Ser Lys His
            1230            1235                1240

CGT ATT GAG CCA GTA TGT TTG TTA GTG CAT GGG AGC CCA GGT ACA GGA     4516
Arg Ile Glu Pro Val Cys Leu Leu Val His Gly Ser Pro Gly Thr Gly
            1245            1250                1255

AAA TCA GTT GCG ACT AAC CTA ATT GCT AGA GCC ATA GCT GAG AAA GAG     4564
Lys Ser Val Ala Thr Asn Leu Ile Ala Arg Ala Ile Ala Glu Lys Glu
        1260            1265                1270

AAC ACC TCC ACC TAC TCG CTA CCA CCG GAC CCG TCT CAC TTT GAT GGA     4612
Asn Thr Ser Thr Tyr Ser Leu Pro Pro Asp Pro Ser His Phe Asp Gly
1275                1280            1285                1290

TAC AAA CAA CAA GGT GTG GTT ATC ATG GAC GAC CTA AAC CAA AAC CCG     4660
Tyr Lys Gln Gln Gly Val Val Ile Met Asp Asp Leu Asn Gln Asn Pro
                1295            1300                1305

GAT GGG GCA GAT ATG AAG CTC TTT TGT CAA ATG GTG TCC ACT GTG GAG     4708
Asp Gly Ala Asp Met Lys Leu Phe Cys Gln Met Val Ser Thr Val Glu
            1310            1315                1320

TTT ATC CCA CCT ATG GCC TCG CTG GAA GAG AAA GGC ATT CTG TTC ACA     4756
Phe Ile Pro Pro Met Ala Ser Leu Glu Glu Lys Gly Ile Leu Phe Thr
            1325            1330                1335

TCC AAC TAT GTT TTA GCC TCC ACC AAC TCC AGT CGC ATC ACA CCA CCT     4804
Ser Asn Tyr Val Leu Ala Ser Thr Asn Ser Ser Arg Ile Thr Pro Pro
        1340            1345                1350

ACA GTA GCC CAC AGT GAC GCT CTG GCC AGG AGG TTC GCT TTC GAT ATG     4852
Thr Val Ala His Ser Asp Ala Leu Ala Arg Arg Phe Ala Phe Asp Met
1355                1360            1365                1370

GAT ATT CAA GTG ATG GGC GAG TAC TCC AGA GAT GGT AAA CTC AAC ATG     4900
Asp Ile Gln Val Met Gly Glu Tyr Ser Arg Asp Gly Lys Leu Asn Met
            1375            1380                1385
```

| | | | | | | | | | | | | | | | | |
|---|---|---|---|---|---|---|---|---|---|---|---|---|---|---|---|---|
| GCA | ATG | GCT | ACT | GAG | ACG | TGC | AAG | GAC | TGC | CAC | CAA | CCA | GCA | AAC | TTC | 4948 |
| Ala | Met | Ala | Thr | Glu | Thr | Cys | Lys | Asp | Cys | His | Gln | Pro | Ala | Asn | Phe | |
| | | | 1390 | | | | 1395 | | | | | 1400 | | | | |
| AAA | AGA | TGC | TGT | CCT | TTA | GTG | TGT | GGT | AAG | GCA | ATT | CAG | TTA | ATG | GAC | 4996 |
| Lys | Arg | Cys | Cys | Pro | Leu | Val | Cys | Gly | Lys | Ala | Ile | Gln | Leu | Met | Asp | |
| | | 1405 | | | | | 1410 | | | | | 1415 | | | | |
| AAA | TCT | TCC | AGA | GTT | AGG | TAC | AGT | GTT | GAC | CAG | ATT | ACT | ACA | ATG | ATT | 5044 |
| Lys | Ser | Ser | Arg | Val | Arg | Tyr | Ser | Val | Asp | Gln | Ile | Thr | Thr | Met | Ile | |
| | 1420 | | | | | 1425 | | | | | 1430 | | | | | |
| ATC | AAC | GAG | AGA | AAC | AGA | AGA | TCT | AAC | ATT | GGC | AAT | TGC | ATG | GAG | GCT | 5092 |
| Ile | Asn | Glu | Arg | Asn | Arg | Arg | Ser | Asn | Ile | Gly | Asn | Cys | Met | Glu | Ala | |
| 1435 | | | | 1440 | | | | 1445 | | | | 1450 | | | | |
| TTG | TTC | CAA | GGA | CCA | CTC | CAG | TAC | AAA | GAC | CTG | AAA | ATT | GAC | ATC | AAG | 5140 |
| Leu | Phe | Gln | Gly | Pro | Leu | Gln | Tyr | Lys | Asp | Leu | Lys | Ile | Asp | Ile | Lys | |
| | | | | 1455 | | | | 1460 | | | | | 1465 | | | |
| ACG | AGG | CCC | CCC | CCT | GAA | TGC | ATC | AAT | GAT | CTG | CTT | CAA | GCA | GTT | GAC | 5188 |
| Thr | Arg | Pro | Pro | Pro | Glu | Cys | Ile | Asn | Asp | Leu | Leu | Gln | Ala | Val | Asp | |
| | | | 1470 | | | | 1475 | | | | | 1480 | | | | |
| TCC | CAG | GAA | GTG | AGG | GAT | TAT | TGT | GAA | AAG | AAA | GGA | TGG | ATC | GTC | AAC | 5236 |
| Ser | Gln | Glu | Val | Arg | Asp | Tyr | Cys | Glu | Lys | Lys | Gly | Trp | Ile | Val | Asn | |
| | 1485 | | | | | 1490 | | | | | 1495 | | | | | |
| ATC | ACT | AGC | CAA | GTT | CAA | ACA | GAG | AGA | AAC | ATT | AAC | CGA | GCA | ATG | ACC | 5284 |
| Ile | Thr | Ser | Gln | Val | Gln | Thr | Glu | Arg | Asn | Ile | Asn | Arg | Ala | Met | Thr | |
| 1500 | | | | | 1505 | | | | | 1510 | | | | | | |
| ATT | TTG | CAG | GCA | GTG | ACA | ACT | TTC | GCC | GCA | GTG | GCT | GGT | GTC | GTG | TAC | 5332 |
| Ile | Leu | Gln | Ala | Val | Thr | Thr | Phe | Ala | Ala | Val | Ala | Gly | Val | Val | Tyr | |
| 1515 | | | | 1520 | | | | | 1525 | | | | | 1530 | | |
| GTC | ATG | TAC | AAG | TTA | TTC | GCT | GGA | CAC | CAG | GGA | GCA | TAC | ACT | GGT | CTG | 5380 |
| Val | Met | Tyr | Lys | Leu | Phe | Ala | Gly | His | Gln | Gly | Ala | Tyr | Thr | Gly | Leu | |
| | | | | 1535 | | | | 1540 | | | | | 1545 | | | |
| CCA | AAC | AAA | AGA | CCC | AAT | GTG | CCC | ACC | ATT | AGA | GCA | GCA | AAA | GTG | CAA | 5428 |
| Pro | Asn | Lys | Arg | Pro | Asn | Val | Pro | Thr | Ile | Arg | Ala | Ala | Lys | Val | Gln | |
| | | 1550 | | | | | 1555 | | | | | 1560 | | | | |
| GGG | CCT | GGG | TTT | GAC | TAT | GCA | GTG | GCT | ATG | GCT | AAA | AGA | AAC | ATT | GTT | 5476 |
| Gly | Pro | Gly | Phe | Asp | Tyr | Ala | Val | Ala | Met | Ala | Lys | Arg | Asn | Ile | Val | |
| | | | 1565 | | | | 1570 | | | | | 1575 | | | | |
| ACA | GCA | ACT | ACT | AGC | AAA | GGG | GAG | TTC | ACA | ATG | CTA | GGA | GTC | CAC | GAC | 5524 |
| Thr | Ala | Thr | Thr | Ser | Lys | Gly | Glu | Phe | Thr | Met | Leu | Gly | Val | His | Asp | |
| | 1580 | | | | | 1585 | | | | | 1590 | | | | | |
| AAC | GTG | GCC | ATT | TTA | CCA | ACT | CAT | GCC | TCA | CCT | GGT | GAG | AGT | ATT | GTA | 5572 |
| Asn | Val | Ala | Ile | Leu | Pro | Thr | His | Ala | Ser | Pro | Gly | Glu | Ser | Ile | Val | |
| 1595 | | | | | 1600 | | | | | 1605 | | | | | 1610 | |
| ATT | GAT | GGC | AAA | GAG | GTT | GAA | ATC | CTA | GAC | GCT | AAA | GCC | CTC | GAA | GAT | 5620 |
| Ile | Asp | Gly | Lys | Glu | Val | Glu | Ile | Leu | Asp | Ala | Lys | Ala | Leu | Glu | Asp | |
| | | | | 1615 | | | | 1620 | | | | | 1625 | | | |
| CAG | GCA | GGC | ACT | AAT | CTG | GAA | ATC | ACC | ATA | ATA | ACC | CTC | AAA | AGA | AAT | 5668 |
| Gln | Ala | Gly | Thr | Asn | Leu | Glu | Ile | Thr | Ile | Ile | Thr | Leu | Lys | Arg | Asn | |
| | | | 1630 | | | | 1635 | | | | | 1640 | | | | |
| GAA | AAG | TTC | AGA | GAT | ATC | AGA | CAA | CAC | ATA | CCC | ACT | CAA | ATC | ACC | GAG | 5716 |
| Glu | Lys | Phe | Arg | Asp | Ile | Arg | Gln | His | Ile | Pro | Thr | Gln | Ile | Thr | Glu | |
| | | | 1645 | | | | 1650 | | | | | 1655 | | | | |
| ACG | AAT | GAT | GGA | GTT | CTG | ATT | GTG | AAC | ACT | AGT | AAG | TAC | CCC | AAC | ATG | 5764 |
| Thr | Asn | Asp | Gly | Val | Leu | Ile | Val | Asn | Thr | Ser | Lys | Tyr | Pro | Asn | Met | |
| | | 1660 | | | | | 1665 | | | | | 1670 | | | | |
| TAT | GTT | CCT | GTC | GGT | GCT | GTG | ACT | GAG | CAG | GGA | TAC | CTA | AAT | CTC | GGT | 5812 |
| Tyr | Val | Pro | Val | Gly | Ala | Val | Thr | Glu | Gln | Gly | Tyr | Leu | Asn | Leu | Gly | |
| 1675 | | | | | 1680 | | | | | 1685 | | | | | 1690 | |
| GGG | CGC | CAG | ACT | GCT | CGT | ATT | CTA | ATG | TAC | AAC | TTT | CCA | ACC | AGA | GCT | 5860 |
| Gly | Arg | Gln | Thr | Ala | Arg | Ile | Leu | Met | Tyr | Asn | Phe | Pro | Thr | Arg | Ala | |
| | | | | 1695 | | | | 1700 | | | | | 1705 | | | |

```
GGT CAG TGT GGT GGA GTC ATC ACA TGC ACT GGG AAA GTC ATC GGG ATG        5908
Gly Gln Cys Gly Gly Val Ile Thr Cys Thr Gly Lys Val Ile Gly Met
            1710                1715                1720

CAC GTT GGT GGG AAT GGT TCA CAT GGG TTT GCA GCG GCC CTG AAG CGG        5956
His Val Gly Gly Asn Gly Ser His Gly Phe Ala Ala Ala Leu Lys Arg
        1725                1730                1735

TCA TAC TTC ACT CAG AGC CAA GGT GAA ATC CAG TGG ATG AGA CCA TCA        6004
Ser Tyr Phe Thr Gln Ser Gln Gly Glu Ile Gln Trp Met Arg Pro Ser
    1740                1745                1750

AAG GAG GCA GGG TAT CCA ATT ATA AAC GCC CCA ACC AAG ACC AAG CTC        6052
Lys Glu Ala Gly Tyr Pro Ile Ile Asn Ala Pro Thr Lys Thr Lys Leu
1755                1760                1765                1770

GAG CCC AGT GCT TTC CAC TAT GTG TTT GAA GGA GTA AAG GAA CCA GCA        6100
Glu Pro Ser Ala Phe His Tyr Val Phe Glu Gly Val Lys Glu Pro Ala
                1775                1780                1785

GTC CTC ACA AAG AAT GAT CCC AGA CTC AAA ACA GAC TTT GAA GAA GCA        6148
Val Leu Thr Lys Asn Asp Pro Arg Leu Lys Thr Asp Phe Glu Glu Ala
            1790                1795                1800

ATC TTC TCT AAG TAT GTA GGG AAC AAG ATC ACT GAG GTG GAT GAG TAC        6196
Ile Phe Ser Lys Tyr Val Gly Asn Lys Ile Thr Glu Val Asp Glu Tyr
        1805                1810                1815

ATG AAA GAG GCA GTG GAC CAT TAT GCT GGA CAA CTT ATG TCG CTG GAT        6244
Met Lys Glu Ala Val Asp His Tyr Ala Gly Gln Leu Met Ser Leu Asp
    1820                1825                1830

ATC AGC ACA GAG CAA ATG TGT CTA GAA GAC GCC ATG TAT GGT ACT GAT        6292
Ile Ser Thr Glu Gln Met Cys Leu Glu Asp Ala Met Tyr Gly Thr Asp
1835                1840                1845                1850

GGT CTG GAG GCG CTA GAT CTG TCT ACC AGT GCC GGG TAC CCC TAC GTG        6340
Gly Leu Glu Ala Leu Asp Leu Ser Thr Ser Ala Gly Tyr Pro Tyr Val
                1855                1860                1865

GCA ATG GGG AAG AAG AAG AGA GAT ATC CTA AAC AAG CAA ACC AGA GAC        6388
Ala Met Gly Lys Lys Lys Arg Asp Ile Leu Asn Lys Gln Thr Arg Asp
            1870                1875                1880

ACC AAA GAA ATG CAA AGA CTT TTG GAC GCT TAC GGA ATC AAC CTA CCA        6436
Thr Lys Glu Met Gln Arg Leu Leu Asp Ala Tyr Gly Ile Asn Leu Pro
        1885                1890                1895

TTA GTG ACA TAT GTC AAG GAC GAG CTG AGG TCC AAA ACA AAA GTG GAA        6484
Leu Val Thr Tyr Val Lys Asp Glu Leu Arg Ser Lys Thr Lys Val Glu
    1900                1905                1910

CAG GGA AAA TCC AGA CTG ATT GAA GCT TCC AGT CTA AAT GAC TCA GTG        6532
Gln Gly Lys Ser Arg Leu Ile Glu Ala Ser Ser Leu Asn Asp Ser Val
1915                1920                1925                1930

GCC ATG AGA ATG GCA TTT GGA AAC CTT TAT GCA GCA TTC CAC AGG AAT        6580
Ala Met Arg Met Ala Phe Gly Asn Leu Tyr Ala Ala Phe His Arg Asn
                1935                1940                1945

CCA GGG GTC GTC ACT GGT AGT GCA GTT GGA TGC GAT CCA GAC CTA TTC        6628
Pro Gly Val Val Thr Gly Ser Ala Val Gly Cys Asp Pro Asp Leu Phe
            1950                1955                1960

TGG AGC AAG ATC CCA GTG TTG ATG GAA GAA AAG CTA TTT GCC TTT GAT        6676
Trp Ser Lys Ile Pro Val Leu Met Glu Glu Lys Leu Phe Ala Phe Asp
        1965                1970                1975

TAC ACA GGA TAC GAC GCA TCA CTT AGC CCA GCT TGG TTT GAG GCA CTC        6724
Tyr Thr Gly Tyr Asp Ala Ser Leu Ser Pro Ala Trp Phe Glu Ala Leu
    1980                1985                1990

AAG ATG GTG TTA GAG AAA ATT GGT TTT GGA GAT AGA GTG GAT TAC ATA        6772
Lys Met Val Leu Glu Lys Ile Gly Phe Gly Asp Arg Val Asp Tyr Ile
1995                2000                2005                2010

GAC TAC CTT AAC CAT TCA CAC CAC TTG TAC AAA AAC AAG ATA TAT TGT        6820
Asp Tyr Leu Asn His Ser His His Leu Tyr Lys Asn Lys Ile Tyr Cys
                2015                2020                2025
```

| | | | | | | | | | | | | | | | | |
|---|---|---|---|---|---|---|---|---|---|---|---|---|---|---|---|---|
| GTT | AAG | GGC | GGC | ATG | CCA | TCT | GGC | TGC | TCC | GGC | ACT | TCA | ATT | TTT | AAT | 6868 |
| Val | Lys | Gly | Gly | Met | Pro | Ser | Gly | Cys | Ser | Gly | Thr | Ser | Ile | Phe | Asn | |
| | | | 2030 | | | | 2035 | | | | | 2040 | | | | |
| TCA | ATG | ATT | AAC | AAT | TTG | ATC | ATT | AGG | ACG | CTT | TTA | CTG | AAA | ACC | TAC | 6916 |
| Ser | Met | Ile | Asn | Asn | Leu | Ile | Ile | Arg | Thr | Leu | Leu | Leu | Lys | Thr | Tyr | |
| | | 2045 | | | | 2050 | | | | | 2055 | | | | | |
| AAG | GGC | ATA | GAT | TTG | GAC | CAC | TTA | AAA | ATG | ATT | GCC | TAT | GGT | GAC | GAT | 6964 |
| Lys | Gly | Ile | Asp | Leu | Asp | His | Leu | Lys | Met | Ile | Ala | Tyr | Gly | Asp | Asp | |
| | 2060 | | | | | 2065 | | | | 2070 | | | | | | |
| GTA | ATA | GCT | TCC | TAT | CCC | CAT | GAG | GTT | GAC | GCT | AGT | CTC | CTA | GCC | CAA | 7012 |
| Val | Ile | Ala | Ser | Tyr | Pro | His | Glu | Val | Asp | Ala | Ser | Leu | Leu | Ala | Gln | |
| 2075 | | | | | 2080 | | | | | 2085 | | | | | 2090 | |
| TCA | GGA | AAA | GAC | TAT | GGA | CTA | ACC | ATG | ACT | CCG | GCA | GAT | AAA | TCT | GCC | 7060 |
| Ser | Gly | Lys | Asp | Tyr | Gly | Leu | Thr | Met | Thr | Pro | Ala | Asp | Lys | Ser | Ala | |
| | | | | 2095 | | | | 2100 | | | | | 2105 | | | |
| ACT | TTT | GAG | ACA | GTC | ACA | TGG | GAG | AAT | GTA | ACT | TTC | TTG | AAA | AGA | TTC | 7108 |
| Thr | Phe | Glu | Thr | Val | Thr | Trp | Glu | Asn | Val | Thr | Phe | Leu | Lys | Arg | Phe | |
| | | | 2110 | | | | 2115 | | | | | 2120 | | | | |
| TTC | AGA | GCA | GAT | GAG | AAA | TAC | CCC | TTC | CTC | ATA | CAT | CCA | GTA | ATG | CCA | 7156 |
| Phe | Arg | Ala | Asp | Glu | Lys | Tyr | Pro | Phe | Leu | Ile | His | Pro | Val | Met | Pro | |
| | | 2125 | | | | 2130 | | | | | 2135 | | | | | |
| ATG | AAG | GAA | ATT | CAT | GAA | TCA | ATC | AGA | TGG | ACA | AAA | GAT | CCT | CGG | AAT | 7204 |
| Met | Lys | Glu | Ile | His | Glu | Ser | Ile | Arg | Trp | Thr | Lys | Asp | Pro | Arg | Asn | |
| | 2140 | | | | | 2145 | | | | 2150 | | | | | | |
| ACG | CAG | GAC | CAT | GTA | CGC | TCC | TTG | TGT | CTA | TTG | GCT | TGG | CAC | AAC | GGG | 7252 |
| Thr | Gln | Asp | His | Val | Arg | Ser | Leu | Cys | Leu | Leu | Ala | Trp | His | Asn | Gly | |
| 2155 | | | | | 2160 | | | | | 2165 | | | | | 2170 | |
| GAA | GAA | GAA | TAC | AAC | AAA | TTT | TTA | GCT | AAA | ATT | AGG | AGT | GTG | CCA | ATC | 7300 |
| Glu | Glu | Glu | Tyr | Asn | Lys | Phe | Leu | Ala | Lys | Ile | Arg | Ser | Val | Pro | Ile | |
| | | | | 2175 | | | | 2180 | | | | | 2185 | | | |
| GGA | AGA | GCT | TTG | TTG | CTC | CCA | GAG | TAC | TCA | ACA | TTG | TAC | CGC | CGT | TGG | 7348 |
| Gly | Arg | Ala | Leu | Leu | Leu | Pro | Glu | Tyr | Ser | Thr | Leu | Tyr | Arg | Arg | Trp | |
| | | | 2190 | | | | 2195 | | | | | 2200 | | | | |
| CTT | GAC | TCA | TTT | T AGTAACCCTA CCTCAGTCGA ATTGGATTGG GTCATACTGT | | | | | | | | | | | | 7401 |
| Leu | Asp | Ser | Phe | | | | | | | | | | | | | |
| | | | 2205 | | | | | | | | | | | | | |

TGTAGGGGTA AATTTTTCTT TAATTCGGAG G                     7432

( 2 ) INFORMATION FOR SEQ ID NO:2:

( i ) SEQUENCE CHARACTERISTICS:
        ( A ) LENGTH: 2206 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Gly | Ala | Gln | Val | Ser | Ser | Gln | Lys | Val | Gly | Ala | His | Glu | Asn | Ser |
| 1 | | | | 5 | | | | | 10 | | | | | 15 | |
| Asn | Arg | Ala | Tyr | Gly | Gly | Ser | Thr | Ile | Asn | Tyr | Thr | Thr | Ile | Asn | Tyr |
| | | | 20 | | | | | 25 | | | | | 30 | | |
| Tyr | Lys | Asp | Ser | Ala | Ser | Asn | Ala | Ala | Ser | Lys | Gln | Asp | Tyr | Ser | Gln |
| | | 35 | | | | | 40 | | | | | 45 | | | |
| Asp | Pro | Ser | Lys | Phe | Thr | Glu | Pro | Leu | Lys | Asp | Val | Leu | Ile | Lys | Thr |
| | 50 | | | | | 55 | | | | | 60 | | | | |
| Ala | Pro | Ala | Leu | Asn | Ser | Pro | Asn | Val | Glu | Ala | Cys | Gly | Tyr | Ser | Asp |
| 65 | | | | | 70 | | | | | 75 | | | | | 80 |
| Arg | Val | Leu | Gln | Leu | Thr | Leu | Gly | Asn | Ser | Thr | Ile | Thr | Thr | Gln | Glu |
| | | | | 85 | | | | | 90 | | | | | 95 | |

| | | | | | | | | | | | | | | |
|---|---|---|---|---|---|---|---|---|---|---|---|---|---|---|
| Ala | Ala | Asn | Ser<br>100 | Val | Val | Ala | Tyr<br>105 | Gly | Arg | Trp | Pro<br>110 | Glu | Phe | Ile | Arg |
| Asp | Asp | Glu<br>115 | Ala | Asn | Pro | Val<br>120 | Asp | Gln | Pro | Thr<br>125 | Glu | Pro | Asp | Val | Ala |
| Thr | Cys<br>130 | Arg | Phe | Tyr | Thr<br>135 | Leu | Asp | Thr | Val | Met<br>140 | Trp | Gly | Lys | Glu | Ser |
| Lys<br>145 | Gly | Trp | Trp | Trp | Lys<br>150 | Leu | Pro | Asp | Ala | Leu<br>155 | Arg | Asp | Met | Gly | Leu<br>160 |
| Phe | Gly | Gln | Asn | Met<br>165 | Tyr | Tyr | His | Tyr | Leu<br>170 | Gly | Arg | Ser | Gly | Tyr<br>175 | Thr |
| Val | His | Val | Gln<br>180 | Cys | Asn | Ala | Ser | Lys<br>185 | Phe | His | Gln | Gly | Ala<br>190 | Leu | Gly |
| Val | Phe | Ala<br>195 | Ile | Pro | Glu | Tyr | Cys<br>200 | Leu | Ala | Gly | Asp | Ser<br>205 | Asp | Lys | Gln |
| Arg | Tyr<br>210 | Thr | Ser | Tyr | Ala | Asn<br>215 | Ala | Asn | Pro | Gly | Glu<br>220 | Arg | Gly | Gly | Lys |
| Phe<br>225 | Tyr | Ser | Gln | Phe | Asn<br>230 | Lys | Asp | Asn | Ala | Val<br>235 | Thr | Ser | Pro | Lys | Arg<br>240 |
| Glu | Phe | Cys | Pro | Val<br>245 | Asp | Tyr | Leu | Leu | Gly<br>250 | Cys | Gly | Val | Leu | Leu<br>255 | Gly |
| Asn | Ala | Phe | Val<br>260 | Tyr | Pro | His | Gln | Ile<br>265 | Ile | Asn | Leu | Arg | Thr<br>270 | Asn | Asn |
| Ser | Ala | Thr<br>275 | Ile | Val | Leu | Pro | Tyr<br>280 | Val | Asn | Ala | Leu | Ala<br>285 | Ile | Asp | Ser |
| Met | Val<br>290 | Lys | His | Asn | Asn | Trp<br>295 | Gly | Ile | Ala | Ile | Leu<br>300 | Pro | Leu | Ser | Pro |
| Leu<br>305 | Asp | Phe | Ala | Gln | Asp<br>310 | Ser | Ser | Val | Glu | Ile<br>315 | Pro | Ile | Thr | Val | Thr<br>320 |
| Ile | Ala | Pro | Met | Cys<br>325 | Ser | Glu | Phe | Asn | Gly<br>330 | Leu | Arg | Asn | Val | Thr<br>335 | Ala |
| Pro | Lys | Phe | Gln | Gly<br>340 | Leu | Pro | Val | Leu | Asn<br>345 | Thr | Pro | Gly | Ser<br>350 | Asn | Gln |
| Tyr | Leu | Thr<br>355 | Ser | Asp | Asn | His | Gln<br>360 | Ser | Pro | Cys | Ala | Ile<br>365 | Pro | Glu | Phe |
| Asp | Val<br>370 | Thr | Pro | Pro | Ile<br>375 | Asp | Ile | Pro | Gly | Glu<br>380 | Val | Lys | Asn | Met | Met |
| Glu<br>385 | Leu | Ala | Glu | Ile | Asp<br>390 | Thr | Met | Ile | Pro | Leu<br>395 | Asn | Leu | Glu | Ser | Thr<br>400 |
| Lys | Arg | Asn | Thr | Met<br>405 | Asp | Met | Tyr | Arg | Val<br>410 | Thr | Leu | Ser | Asp | Ser<br>415 | Ala |
| Asp | Leu | Ser | Gln<br>420 | Pro | Ile | Leu | Cys | Leu<br>425 | Ser | Leu | Ser | Pro | Ala<br>430 | Phe | Asp |
| Pro | Arg | Leu<br>435 | Ser | His | Thr | Met | Leu<br>440 | Gly | Glu | Val | Leu | Asn<br>445 | Tyr | Tyr | Thr |
| His | Trp<br>450 | Ala | Gly | Ser | Leu | Lys<br>455 | Phe | Thr | Phe | Leu | Phe<br>460 | Cys | Gly | Ser | Met |
| Met<br>465 | Ala | Thr | Gly | Lys | Ile<br>470 | Leu | Val | Ala | Tyr | Ala<br>475 | Pro | Pro | Gly | Ala | Gln<br>480 |
| Pro | Pro | Thr | Ser | Arg<br>485 | Lys | Glu | Ala | Met | Leu<br>490 | Gly | Thr | His | Val | Ile<br>495 | Trp |
| Asp | Leu | Gly | Leu<br>500 | Gln | Ser | Ser | Cys | Thr<br>505 | Met | Val | Val | Pro | Trp<br>510 | Ile | Ser |
| Asn | Val | Thr<br>515 | Tyr | Arg | Gln | Thr | Thr<br>520 | Gln | Asp | Ser | Phe | Thr<br>525 | Glu | Gly | Gly |

| Tyr | Ile | Ser | Met | Phe | Tyr | Gln | Thr | Arg | Ile | Val | Val | Pro | Leu | Ser | Thr |
|---|---|---|---|---|---|---|---|---|---|---|---|---|---|---|---|
| | 530 | | | | 535 | | | | | 540 | | | | | |

Pro Lys Ser Met Ser Met Leu Gly Phe Val Ser Ala Cys Asn Asp Phe
545             550                 555                 560

Ser Val Arg Leu Leu Arg Asp Thr Thr His Ile Ser Gln Ser Ala Leu
                565                 570                 575

Pro Gln Gly Ile Glu Asp Leu Thr Ser Glu Val Ala Gln Gly Ala Leu
            580                 585                 590

Thr Leu Ser Leu Pro Lys Gln Gln Asp Ser Leu Pro Asp Thr Lys Ala
                595                 600                 605

Ser Gly Pro Ala His Ser Lys Glu Val Pro Ala Leu Thr Ala Val Glu
    610                 615                 620

Thr Gly Ala Thr Asn Pro Leu Ala Pro Ser Asp Thr Val Gln Thr Arg
625                 630                 635                 640

His Val Val Gln Arg Arg Ser Arg Ser Glu Ser Thr Ile Glu Ser Phe
                645                 650                 655

Phe Ala Arg Gly Ala Cys Val Ala Ile Ile Glu Val Asp Asn Glu Gln
            660                 665                 670

Pro Thr Thr Arg Ala Gln Lys Leu Phe Ala Met Trp Arg Ile Thr Tyr
        675                 680                 685

Lys Asp Thr Val Gln Leu Arg Arg Lys Leu Glu Phe Phe Thr Tyr Ser
    690                 695                 700

Arg Phe Asp Met Glu Phe Thr Phe Val Val Thr Ala Asn Phe Thr Asn
705                 710                 715                 720

Ala Asn Asn Gly His Ala Leu Asn Gln Val Tyr Gln Ile Met Tyr Ile
                725                 730                 735

Pro Pro Gly Ala Pro Thr Pro Lys Ser Trp Asp Asp Tyr Thr Trp Gln
            740                 745                 750

Thr Ser Ser Asn Pro Ser Ile Phe Tyr Thr Tyr Gly Ala Ala Pro Ala
        755                 760                 765

Arg Ile Ser Val Pro Tyr Val Gly Leu Ala Asn Ala Tyr Ser His Phe
    770                 775                 780

Tyr Asp Gly Phe Ala Lys Val Pro Leu Lys Thr Asp Ala Asn Asp Gln
785                 790                 795                 800

Ile Gly Asp Ser Leu Tyr Ser Ala Met Thr Val Asp Asp Phe Gly Val
                805                 810                 815

Leu Ala Val Arg Val Val Asn Asp His Asn Pro Thr Lys Val Thr Ser
            820                 825                 830

Lys Val Arg Ile Tyr Met Lys Pro Lys His Val Arg Val Trp Cys Pro
        835                 840                 845

Arg Pro Pro Arg Ala Val Pro Tyr Tyr Gly Pro Gly Val Asp Tyr Arg
    850                 855                 860

Asn Asn Leu Asp Pro Leu Ser Glu Lys Gly Leu Thr Thr Tyr Gly Phe
865                 870                 875                 880

Gly His Gln Asn Lys Ala Val Tyr Thr Ala Gly Tyr Lys Ile Cys Asn
                885                 890                 895

Tyr His Leu Ala Thr Lys Glu Asp Leu Gln Asn Ala Val Ser Ile Met
            900                 905                 910

Trp Asn Arg Asp Leu Leu Val Val Glu Ser Lys Ala Gln Gly Thr Asp
        915                 920                 925

Ser Ile Ala Arg Cys Asn Cys Asn Ala Gly Val Tyr Tyr Cys Glu Ser
    930                 935                 940

Arg Arg Lys Tyr Tyr Pro Val Ser Phe Val Gly Pro Thr Phe Gln Tyr

```
945                     950                     955                     960
Met Glu Ala Asn Asp Tyr Tyr Pro Ala Arg Tyr Gln Ser His Met Leu
                965                     970                     975
Ile Gly His Gly Phe Ala Ser Pro Gly Asp Cys Gly Gly Ile Leu Arg
                980                     985                     990
Cys Gln His Gly Val Ile Gly Ile Val Thr Ala Gly Gly Glu Gly Leu
                995                     1000                    1005
Val Ala Phe Ser Asp Ile Arg Asp Leu Tyr Ala Tyr Glu Glu Glu Ala
        1010                    1015                    1020
Met Glu Gln Gly Ile Ser Asn Tyr Ile Glu Ser Leu Gly Ala Ala Phe
1025                    1030                    1035                    1040
Gly Ser Gly Phe Thr Gln Gln Ile Gly Asp Lys Ile Ser Glu Leu Thr
                1045                    1050                    1055
Ser Met Val Thr Ser Thr Ile Thr Glu Lys Leu Leu Lys Asn Leu Ile
                1060                    1065                    1070
Lys Ile Ile Ser Ser Leu Val Ile Ile Thr Arg Asn Tyr Glu Asp Thr
        1075                    1080                    1085
Thr Thr Val Leu Ala Thr Leu Ala Leu Leu Gly Cys Asp Val Ser Pro
        1090                    1095                    1100
Trp Gln Trp Leu Lys Lys Lys Ala Cys Asp Thr Leu Glu Ile Pro Tyr
1105                    1110                    1115                    1120
Val Ile Arg Gln Gly Asp Ser Trp Leu Lys Lys Phe Thr Glu Ala Cys
                1125                    1130                    1135
Asn Ala Ala Lys Gly Leu Glu Trp Val Ser Asn Lys Ile Ser Lys Phe
                1140                    1145                    1150
Ile Asp Trp Leu Arg Glu Arg Ile Ile Pro Gln Ala Arg Asp Lys Leu
        1155                    1160                    1165
Glu Phe Val Thr Lys Leu Lys Gln Leu Glu Met Leu Glu Asn Gln Ile
        1170                    1175                    1180
Ser Thr Ile His Gln Ser Cys Pro Ser Gln Glu His Gln Glu Ile Leu
1185                    1190                    1195                    1200
Phe Asn Asn Val Arg Trp Leu Ser Ile Gln Ser Lys Arg Phe Ala Pro
                1205                    1210                    1215
Leu Tyr Ala Leu Glu Ala Lys Arg Ile Gln Lys Leu Glu His Thr Ile
                1220                    1225                    1230
Asn Asn Tyr Ile Gln Phe Lys Ser Lys His Arg Ile Glu Pro Val Cys
        1235                    1240                    1245
Leu Leu Val His Gly Ser Pro Gly Thr Gly Lys Ser Val Ala Thr Asn
        1250                    1255                    1260
Leu Ile Ala Arg Ala Ile Ala Glu Lys Glu Asn Thr Ser Thr Tyr Ser
1265                    1270                    1275                    1280
Leu Pro Pro Asp Pro Ser His Phe Asp Gly Tyr Lys Gln Gln Gly Val
                1285                    1290                    1295
Val Ile Met Asp Asp Leu Asn Gln Asn Pro Asp Gly Ala Asp Met Lys
                1300                    1305                    1310
Leu Phe Cys Gln Met Val Ser Thr Val Glu Phe Ile Pro Pro Met Ala
        1315                    1320                    1325
Ser Leu Glu Glu Lys Gly Ile Leu Phe Thr Ser Asn Tyr Val Leu Ala
        1330                    1335                    1340
Ser Thr Asn Ser Ser Arg Ile Thr Pro Pro Thr Val Ala His Ser Asp
1345                    1350                    1355                    1360
Ala Leu Ala Arg Arg Phe Ala Phe Asp Met Asp Ile Gln Val Met Gly
                1365                    1370                    1375
```

```
Glu Tyr Ser Arg Asp Gly Lys Leu Asn Met Ala Met Ala Thr Glu Thr
            1380                1385                1390
Cys Lys Asp Cys His Gln Pro Ala Asn Phe Lys Arg Cys Cys Pro Leu
        1395                1400                1405
Val Cys Gly Lys Ala Ile Gln Leu Met Asp Lys Ser Ser Arg Val Arg
    1410                1415                1420
Tyr Ser Val Asp Gln Ile Thr Thr Met Ile Asn Glu Arg Asn Arg
1425            1430                1435                    1440
Arg Ser Asn Ile Gly Asn Cys Met Glu Ala Leu Phe Gln Gly Pro Leu
                1445                1450                1455
Gln Tyr Lys Asp Leu Lys Ile Asp Ile Lys Thr Arg Pro Pro Pro Glu
            1460                1465                1470
Cys Ile Asn Asp Leu Leu Gln Ala Val Asp Ser Gln Glu Val Arg Asp
        1475                1480                1485
Tyr Cys Glu Lys Lys Gly Trp Ile Val Asn Ile Thr Ser Gln Val Gln
    1490                1495                1500
Thr Glu Arg Asn Ile Asn Arg Ala Met Thr Ile Leu Gln Ala Val Thr
1505            1510                1515                    1520
Thr Phe Ala Ala Val Ala Gly Val Val Tyr Val Met Tyr Lys Leu Phe
                1525                1530                1535
Ala Gly His Gln Gly Ala Tyr Thr Gly Leu Pro Asn Lys Arg Pro Asn
            1540                1545                1550
Val Pro Thr Ile Arg Ala Ala Lys Val Gln Gly Pro Gly Phe Asp Tyr
        1555                1560                1565
Ala Val Ala Met Ala Lys Arg Asn Ile Val Thr Ala Thr Thr Ser Lys
    1570                1575                1580
Gly Glu Phe Thr Met Leu Gly Val His Asp Asn Val Ala Ile Leu Pro
1585            1590                1595                    1600
Thr His Ala Ser Pro Gly Glu Ser Ile Val Ile Asp Gly Lys Glu Val
                1605                1610                1615
Glu Ile Leu Asp Ala Lys Ala Leu Glu Asp Gln Ala Gly Thr Asn Leu
            1620                1625                1630
Glu Ile Thr Ile Ile Thr Leu Lys Arg Asn Glu Lys Phe Arg Asp Ile
        1635                1640                1645
Arg Gln His Ile Pro Thr Gln Ile Thr Glu Thr Asn Asp Gly Val Leu
    1650                1655                1660
Ile Val Asn Thr Ser Lys Tyr Pro Asn Met Tyr Val Pro Val Gly Ala
1665            1670                1675                    1680
Val Thr Glu Gln Gly Tyr Leu Asn Leu Gly Gly Arg Gln Thr Ala Arg
                1685                1690                1695
Ile Leu Met Tyr Asn Phe Pro Thr Arg Ala Gly Gln Cys Gly Gly Val
            1700                1705                1710
Ile Thr Cys Thr Gly Lys Val Ile Gly Met His Val Gly Gly Asn Gly
        1715                1720                1725
Ser His Gly Phe Ala Ala Ala Leu Lys Arg Ser Tyr Phe Thr Gln Ser
    1730                1735                1740
Gln Gly Glu Ile Gln Trp Met Arg Pro Ser Lys Glu Ala Gly Tyr Pro
1745            1750                1755                    1760
Ile Ile Asn Ala Pro Thr Lys Thr Lys Leu Glu Pro Ser Ala Phe His
                1765                1770                1775
Tyr Val Phe Glu Gly Val Lys Glu Pro Ala Val Leu Thr Lys Asn Asp
            1780                1785                1790
Pro Arg Leu Lys Thr Asp Phe Glu Glu Ala Ile Phe Ser Lys Tyr Val
        1795                1800                1805
```

Gly Asn Lys Ile Thr Glu Val Asp Glu Tyr Met Lys Glu Ala Val Asp
    1810                1815                1820

His Tyr Ala Gly Gln Leu Met Ser Leu Asp Ile Ser Thr Glu Gln Met
1825            1830                1835                1840

Cys Leu Glu Asp Ala Met Tyr Gly Thr Asp Gly Leu Glu Ala Leu Asp
                1845                1850                1855

Leu Ser Thr Ser Ala Gly Tyr Pro Tyr Val Ala Met Gly Lys Lys Lys
            1860                1865                1870

Arg Asp Ile Leu Asn Lys Gln Thr Arg Asp Thr Lys Glu Met Gln Arg
        1875                1880                1885

Leu Leu Asp Ala Tyr Gly Ile Asn Leu Pro Leu Val Thr Tyr Val Lys
        1890                1895                1900

Asp Glu Leu Arg Ser Lys Thr Lys Val Glu Gln Gly Lys Ser Arg Leu
1905                1910                1915                1920

Ile Glu Ala Ser Ser Leu Asn Asp Ser Val Ala Met Arg Met Ala Phe
                1925                1930                1935

Gly Asn Leu Tyr Ala Ala Phe His Arg Asn Pro Gly Val Val Thr Gly
            1940                1945                1950

Ser Ala Val Gly Cys Asp Pro Asp Leu Phe Trp Ser Lys Ile Pro Val
            1955                1960                1965

Leu Met Glu Glu Lys Leu Phe Ala Phe Asp Tyr Thr Gly Tyr Asp Ala
    1970                1975                1980

Ser Leu Ser Pro Ala Trp Phe Glu Ala Leu Lys Met Val Leu Glu Lys
1985            1990                1995                2000

Ile Gly Phe Gly Asp Arg Val Asp Tyr Ile Asp Tyr Leu Asn His Ser
            2005                2010                2015

His His Leu Tyr Lys Asn Lys Ile Tyr Cys Val Lys Gly Gly Met Pro
        2020                2025                2030

Ser Gly Cys Ser Gly Thr Ser Ile Phe Asn Ser Met Ile Asn Asn Leu
    2035                2040                2045

Ile Ile Arg Thr Leu Leu Leu Lys Thr Tyr Lys Gly Ile Asp Leu Asp
2050                2055                2060

His Leu Lys Met Ile Ala Tyr Gly Asp Asp Val Ile Ala Ser Tyr Pro
2065                2070                2075                2080

His Glu Val Asp Ala Ser Leu Leu Ala Gln Ser Gly Lys Asp Tyr Gly
                2085                2090                2095

Leu Thr Met Thr Pro Ala Asp Lys Ser Ala Thr Phe Glu Thr Val Thr
            2100                2105                2110

Trp Glu Asn Val Thr Phe Leu Lys Arg Phe Phe Arg Ala Asp Glu Lys
        2115                2120                2125

Tyr Pro Phe Leu Ile His Pro Val Met Pro Met Lys Glu Ile His Glu
    2130                2135                2140

Ser Ile Arg Trp Thr Lys Asp Pro Arg Asn Thr Gln Asp His Val Arg
2145                2150                2155                2160

Ser Leu Cys Leu Leu Ala Trp His Asn Gly Glu Glu Glu Tyr Asn Lys
                2165                2170                2175

Phe Leu Ala Lys Ile Arg Ser Val Pro Ile Gly Arg Ala Leu Leu Leu
            2180                2185                2190

Pro Glu Tyr Ser Thr Leu Tyr Arg Arg Trp Leu Asp Ser Phe
            2195                2200                2205

( 2 ) INFORMATION FOR SEQ ID NO:3:

( i ) SEQUENCE CHARACTERISTICS:

(A) LENGTH: 30 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:3:

CGCCTCAGTA AATTTTTTCA ACCAACTATC 30

(2) INFORMATION FOR SEQ ID NO:4:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:4:

GGCGTATCTG ACAAGGG 17

(2) INFORMATION FOR SEQ ID NO:5:

(i) SEQUENCE CHARACTERISTICS:
(A) LENGTH: 45 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:5:

CTGCAGTAAT ACGACTCACT ATAGGTTAAA ACAGCTCTGG GGTTG 45

(2) INFORMATION FOR SEQ ID NO:6:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:6:

GAATCATGGT GTCTATCTC 19

(2) INFORMATION FOR SEQ ID NO:7:

(i) SEQUENCE CHARACTERISTICS:
(A) LENGTH: 17 base pairs
(B) TYPE: nucleic acid
(C) STRANDEDNESS: single
(D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:7:

CTCGTTTGTG GCATAAC 17

(2) INFORMATION FOR SEQ ID NO:8:

(i) SEQUENCE CHARACTERISTICS:
 (A) LENGTH: 17 base pairs
 (B) TYPE: nucleic acid
 (C) STRANDEDNESS: single
 (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:8:

CCCATGGGGA TGCACCG 17

(2) INFORMATION FOR SEQ ID NO:9:

(i) SEQUENCE CHARACTERISTICS:
 (A) LENGTH: 46 base pairs
 (B) TYPE: nucleic acid
 (C) STRANDEDNESS: single
 (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:9:

CTGCAGTAAT ACGACTCACT ATAGGTTAAA ACAGCTCTGG GGTTTG 46

METHOD FOR PRODUCING RNA VIRUSES FROM CDNA

This application is the U.S. national stage application of the international application, PCT/US91/05890, filed Aug. 20, 1991, which is a continuation-in-part of U.S. Ser. No. 07/569,916, filed Aug. 20, 1990, now abandoned, and a continuation-in-part of U.S. Ser. No. 07/570,000, filed August 20, 1990, now abandoned.

BACKGROUND OF THE INVENTION

Throughout this application various references are referred to within parentheses or with arabic numerals within parenthesis. Full bibliographic citations for these publications referred to by arabic numerals may be found at the end of the specification immediately preceding the claims. The disclosures of these publications in their entireties are hereby incorporated by reference into this application to more fully describe the state of the art to which this invention pertains.

Human enteroviruses belonging to the family Picornaviridae are characterized by a single-stranded positive RNA genome. Members of this viral family include poliovirus, echoviruses, coxsackieviruses and rhinoviruses. Among these viruses, poliovirus has been the most extensively studied.

Poliovirus is known to be the causative agent of poliomyelitis, a paralytic disease of the central nervous system. This virus is known to exist in three stable serotypes—1, 2 and 3. For over 25 years, this disease has been controlled by the use of both the Sabin oral live-attenuated vaccine and the Salk inactivated virus vaccine. The Sabin vaccine consists of attenuated virus of each serotype, none of which are capable of causing disease. The strains used to produce the vaccine were created by a combination of extensive in vivo and in vitro passage of each of the three wild-type strains through monkey tissue. Upon oral administration, the live virus contained in the Sabin vaccine replicates in the gut, thereby inducing both systemic and local immunity. The killed virus (Salk) vaccine, which is administered intramuscularly, is limited to inducing systemic immunity.

Although the Sabin vaccine is considered to be a safe and effective protection against poliomyelitis, a small number of recipients have developed vaccine-associated the disease.

In an effort to understand the molecular basis of attenuation and reversion, the nucleotide sequences of cDNAs corresponding to each of the 3 attenuated strains and their wild-type progenitors, were compared [A. Nomoto et al., "Complete Nucleotide Sequence of the Attenuated Sabin 1 Strain Genome", *Proc. Natl. Acad. Sci. USA*, 79, pp 5793–97 (1982); G. Stanway et al., "Nucleic Acid Sequence of the Region of the Genome Encoding Capsid Protein VP1 of Neurovirulent and Attenuated Type 3 Polioviruses", *Eur. J. Biochem.*, 135, pp. 529–33 (1983); G. Stanway et al., "Comparison of the Complete Nucleotide Sequences of the Genomes of the Neurovirulent Poliovirus P3/Leon/37 and its Attenuated Sabin Vaccine Derivative P3/Leon 12ab", *Proc. Natl. Acad. Sci. USA*, 79, pp. 1539–43 (1984); and H. Toyoda et al., "Complete Nucleotide Sequences of All Three Poliovirus Serotype Genomes", *J. Mol. Biol.*, 174 pp 561–585 (1984)]. The observed differences in nucleotide sequence between each wild-type progenitor and its resultant attenuated strain were then further analyzed to determine their relationship to the phenomenon of attenuation.

In serotype 3, for example, the attenuated strain differed from the wild-type strain by only 10 point mutations [G. Stanway et al., (1984), supra]. Of these differences, only the changes at nucleotide positions 472 and 2034 were thought to be strongly associated with attenuation [D. M. A. Evans et al., "Increased Neurovirulence Associated With A Single Nucleotide Change In A Noncoding Region of the Sabin Type 3 Poliovirus Genome", *Nature*, 314, pp. 548–50 (1985); G. D. Westrop et al., "Genetic Basis of Attenuation of the Sabin Type 3 Oral Poliovirus Vaccine", *J. Virol.*, 63, pp. 1338–44 (1989)].

Prior to the identification of the nucleotides which are linked to attenuation, it was demonstrated that cDNA synthesized from a viral RNA template ("RNA virus cDNA") could be utilized to produce viable poliovirus following transfection of mammalian cells [V. R. Racaniello et al., "Cloned Poliovirus Complementary DNA Is Infectious In Mammalian Cells", *Science*, 214, pp. 916–19 (1981)]. Such observations created the possibility of producing improved polio vaccines via genetic engineering techniques. This could be achieved by altering the cDNA around the crucial nucleotides so as to minimize reversion to the wild-type nucleotide, while maintaining structural and functional integrity of the virus.

Despite the discovery that RNA virus cDNA can be used to produce viable virus, it has never been demonstrated that these cDNA are accurate copies of the viral RNA present in wild-type or vaccine virus. Moreover, the use of cDNA sequences to determine which nucleotides are linked to attenuation, may have caused one or more critical sites to have been overlooked. This is because the process used to produce cDNA, namely reverse transcription, is known to be errorprone [I. M. Verma, "Reverse Transcriptase", In *The Enzyme*, Vol. 14, P. D, Boyer, ed., Academic Press, New York, pp. 87–104 (1981)].

Accordingly, a need still exists for the production of RNA virus cDNAs which are truly complementary to the vaccine virus RNA. Moreover, the use of inaccurate RNA virus cDNAs may result in reduced attenuation, if these cDNAs are ultimately to be used to produce vaccines, such as polio vaccines.

The genome of poliovirus is a single-stranded RNA molecule of plus-sense that is approximately 7500 nucleotides in length. The error frequency associated with replication of single-stranded RNA, as for poliovirus, is especially high compared to that of double-stranded DNA (3). Due to this inherent property, every preparation of poliovirus including the original Sabin (SO) strains must be considered genotypically heterogeneous.

Culture conditions (ie. temperature, cell substrate) as well as the homogeneity of the input virus are likely to influence which genotype predominates during amplication of a poliovirus sample. It is therefore not surprising that authorities who regulate the manufacture of OPVs (ie. FDA and WHO) dictate strict guidelines regarding the production of manufacturing seeds as well as the passage level of the seed represented in vaccine (22, 26). These regulations were put into action as an effort to minimize selection and amplification of less attenuated variant strains.

It has been well documented that the attenuated phenotype of the Sabin 3 strain is less genetically stable than the type 1 and 2 vaccine strains (4, 7, 11). In the past, a new manufacturing seed (RSO) was derived from the original Sabin 3 virus by selecting a plaque produced in Vervet monkey kidney cell monolayers from extracted infectious RNA (19). The isolate was chosen based on increased stability of its sensitivity to grow at 40.3° C. (rct marker) during serial passage as well as increased attenuation in monkeys. The sensitivity of growth at temperatures above 37° (rct marker) is still employed as an in vitro biological test to analyze the quality of vaccine strains (13).

A report by Kohara et al. (9) suggested that an infectious cDNA clone might be used to preserve the constancy and quality of the Sabin 1 seed. It is plausible that a similar approach could also benefit the attenuated type 3 strain. Until recently, the literature contained two cDNA sequences for Sabin 3 which differed at nucleotide positions (17, 21). The divergence between these sequences may be due to the fact that passage derivatives and clonal isolates of Sabin 3 rather than actual vaccine virus were used for making the cDNA clones.

SUMMARY OF THE INVENTION

This invention also provides a vaccine useful for immunizing a subject, for example a human, against infectious poliovirus, wherein the vaccine comprises an effective amount of an RNA virus, produced by transforming a suitable host cell with a recombinant nucleic acid sequence which encodes for the virus; and isolating the virus so produced, effective to immunize the subject.

Further provided by this invention is a method of immunizing a subject such as a human against infectious poliovirus, wherein the method comprises administering to the subject a suitable dose of the vaccine described hereinabove.

BRIEF DESCRIPTION OF THE DRAWINGS

FIG. 3 depicts the strategy for assembling partial cDNAs into a single, full-length P3/Sabin cDNA according to this invention.

In order to reconstruct pLED3 with the correct number of A's, the SacI/HindIII fragment from pLL3-271 used above was cloned into bacteriophage M13 for oligonucleotide-directed deletion mutagenesis. An oligonucleotide spanning nucleotides 4121–4150 was synthesized for this purpose. The oligonucleotide has the sequence: 5'-CGCCTCAG-TAAATTTTTTCAACCAACTATC- 3' (SEQ ID NO:3)

Mutagenesis was performed using a "T7-GEN In Vitro Mutagenesis Kit" (United States Biochemical, Cleveland, Ohio) and following the manufacturer's directions. The mutagenized insert was called CB2 and was demonstrated to possess six A's at positions 4133–4138 as well as C at 2493 by sequence analysis. The corrected full-length construct was made by ligating the SacI/HindIII fragment of CB2 to the SacI/HindIII partial digestion fragment of pVR318 which had been used in the original pLED3 construction. The product of this ligation was called pLED3.2. The entire cDNA sequence of pLED3.2 has been verified to match the sequence reported in FIGS. 6A–6K.

Figure 4A:
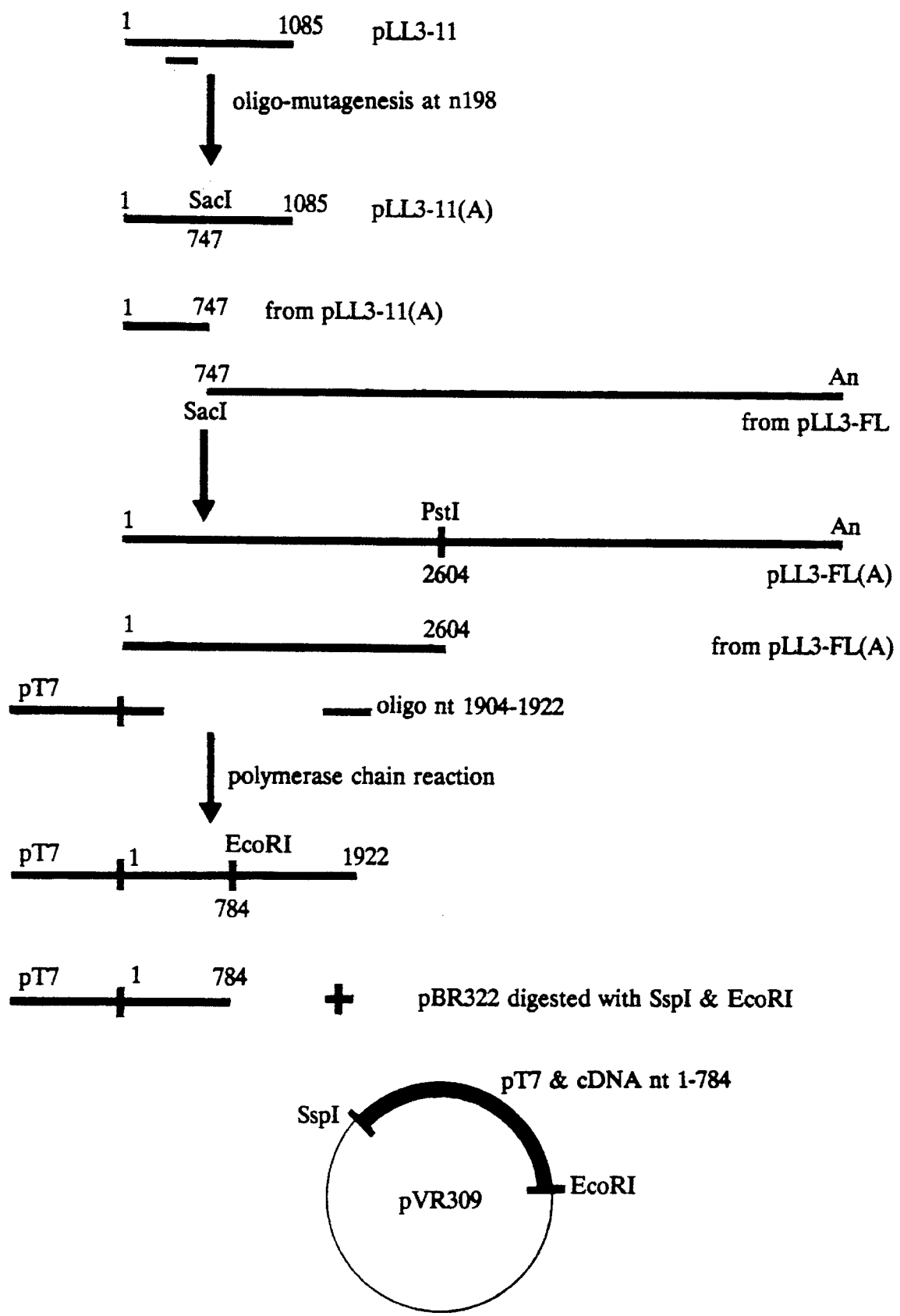
FIGS. 4A and 4B depict the strategy for mutagenizing P3/Sabin cDNA and constructing a true, full-length P3/Sabin cDNA according to this invention. Depiction of the strategy continues in FIG. 5.
Figure 4B:
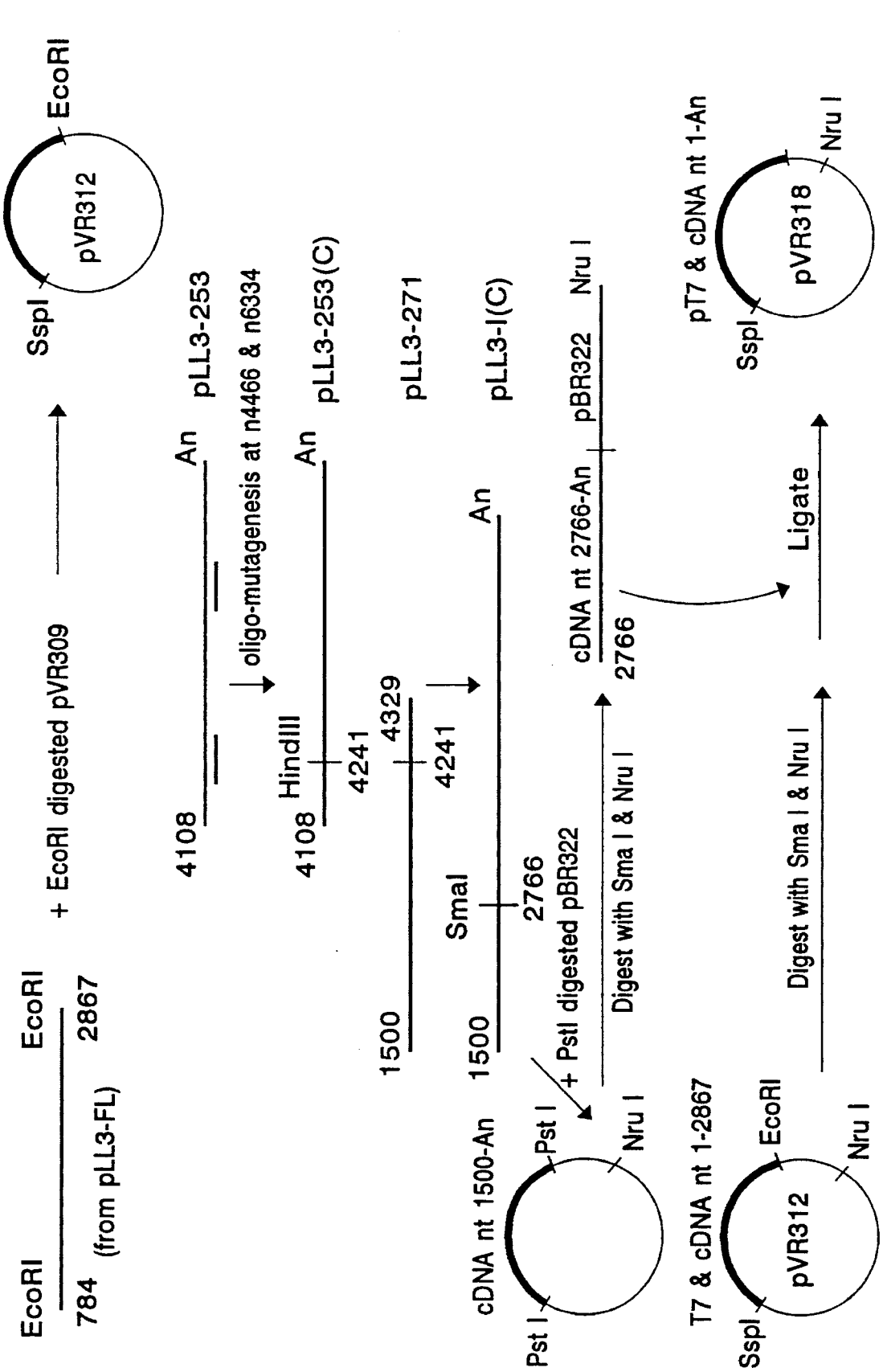
Figure 4C:
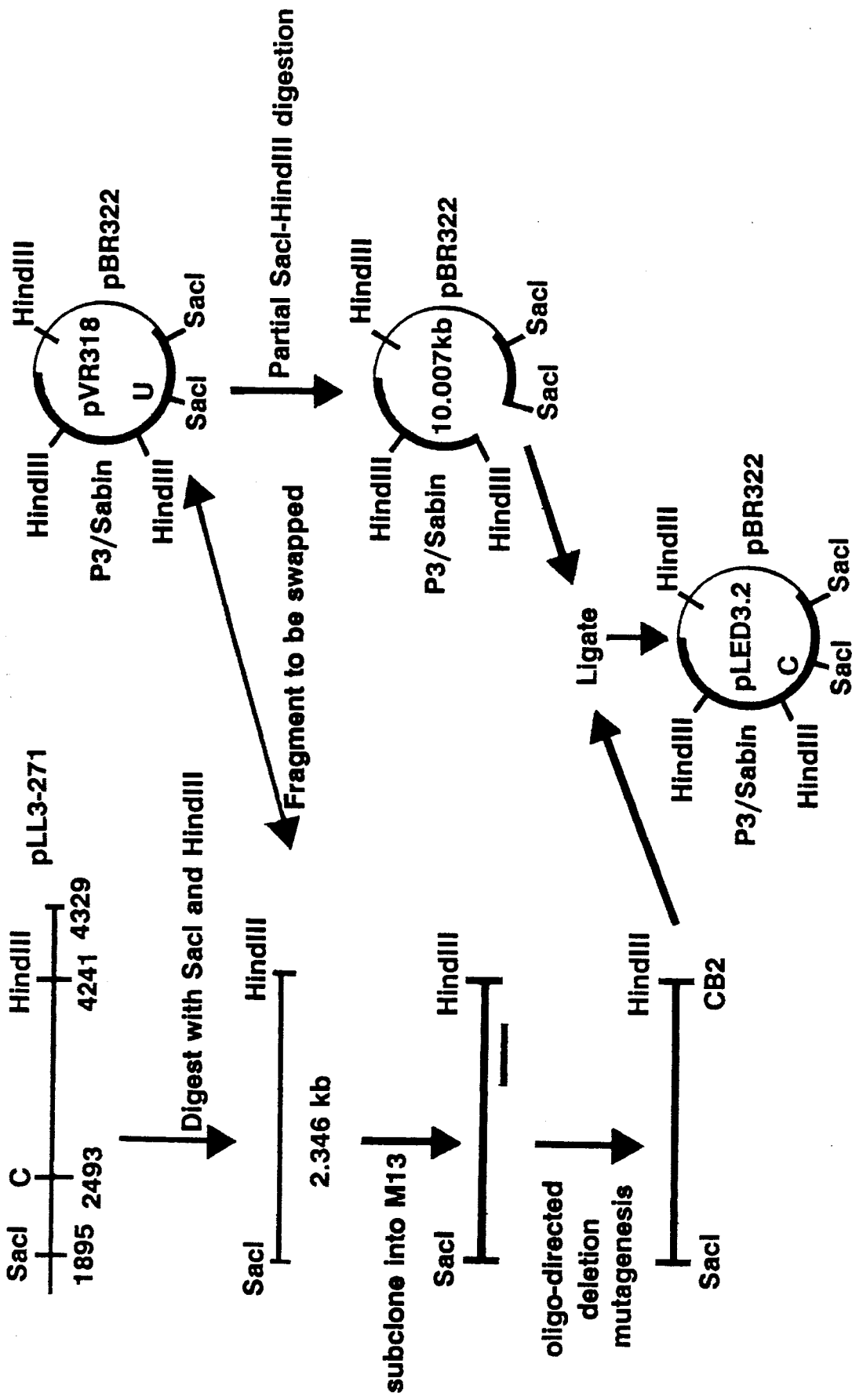
FIG. 4C depicts the following. The sequence of pLED3 depiced in FIGS. 6A–6K (SEQ ID NO:1–2) was deduced from the complete analysis of pVR318 which was then altered at position 2493 by exchanging a SacI/HindIII fragment from the same subclone (pLL3-271) used to construct pVR318. However, confirmatory sequencing of the entire cDNA sequence in plasmid pLED3 revealed an additional "A" (adenosine) in a region where a run of six A's is normally found in the vital genome (position 4133–4138). The erroneous "A" was also found in subclone pLL3-271. The pLL3-271 and pBr318 were manipulated to make pLED3.2 which contains the correct number of A's at this site.
Figure 5:
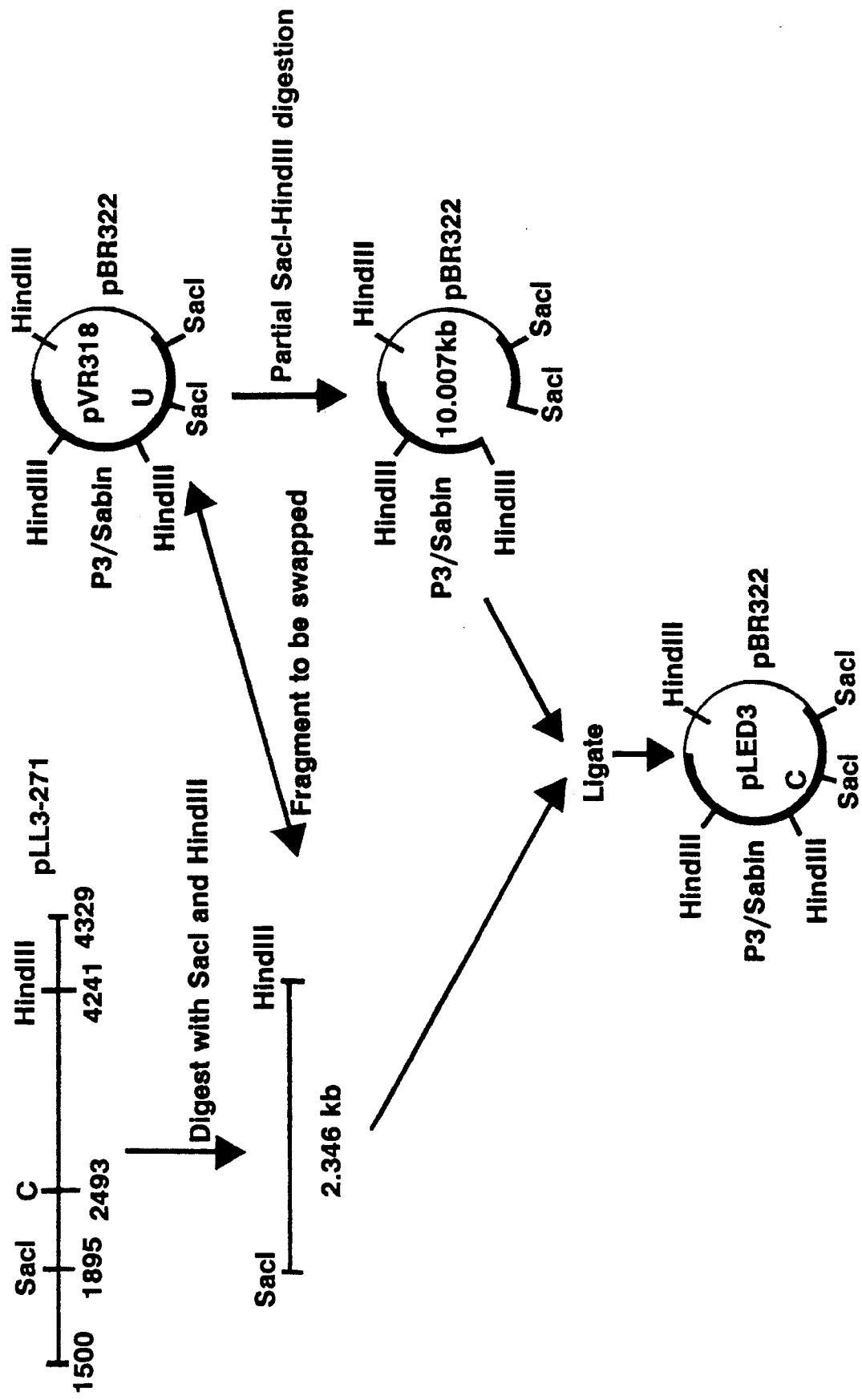

FIG. 5 continues depiction of the strategy depicted in FIGS. 4A and 4B.

FIGS. 6A through 6K (SEQ ID NO:1–2) depict the nucleotide sequence of a true type 3 poliovirus vaccine strain cDNA according to this invention.

Figure 7A:
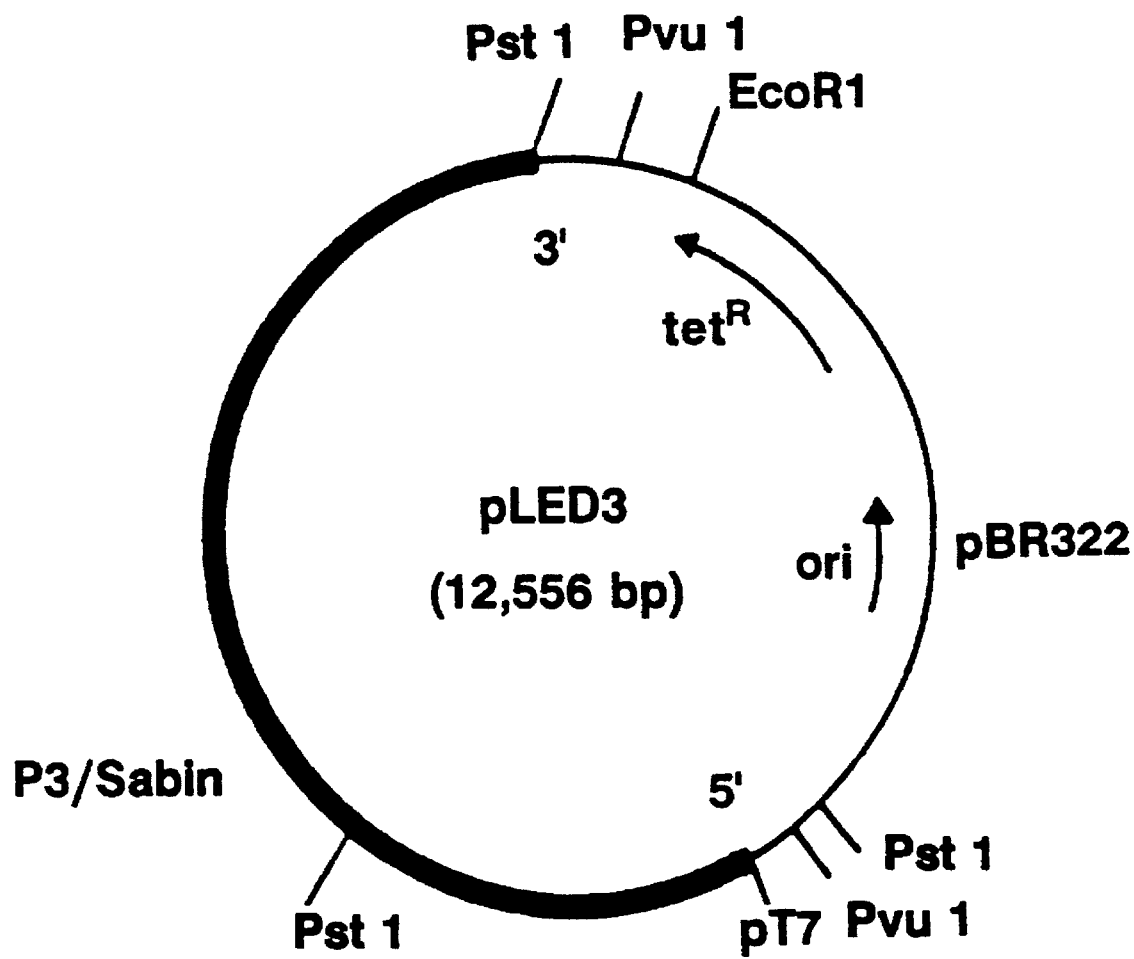
Figure 7B:
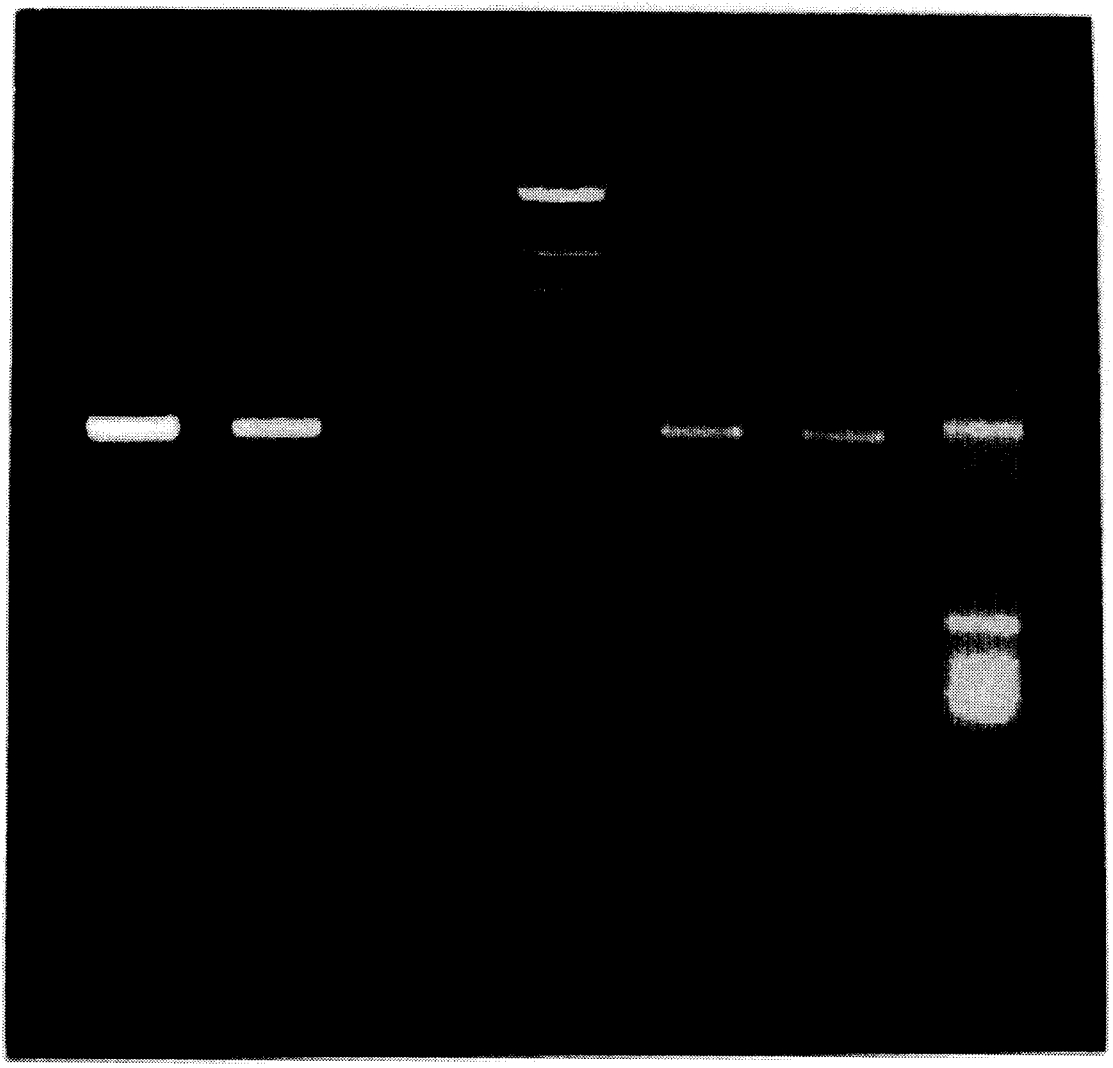

FIGS. 7A and 7B. FIG. 7A depicts the structure of the plasmid containing full-length LED3 cDNA and the T7 RNA polymerase promoter. The large shaded area represents the poliovirus cDNA. The small open area indicates the T7 promoter (pT7) and the start site for in vitro positive polarity transcripts of the cDNA. The plasmid is cut with PvuI (sites shown) before run-off transcripts are synthesized. FIG. 7B depicts RNAs transcribed from cDNA clones by purified T7 RNA polymerase. Portions of the transcription reaction mixture were analyzed by electrophoresis in a 0.6% agarose gel as described in Materials and Methods, Example 13. Lanes 1–3 represent 0.75 µg, 0.50 µg and 0.25 µg of 7.5 kb ssRNA marker, respectively. HindIII-digested phage lambda DNA is shown in lane 4. Lanes 5 & 6 demonstrate transcription reactions containing PvuI-digested pLED3 and pVR318 templates, respectively. RNA extracted from pelleted virions is shown in lane 7.

Figure 8:
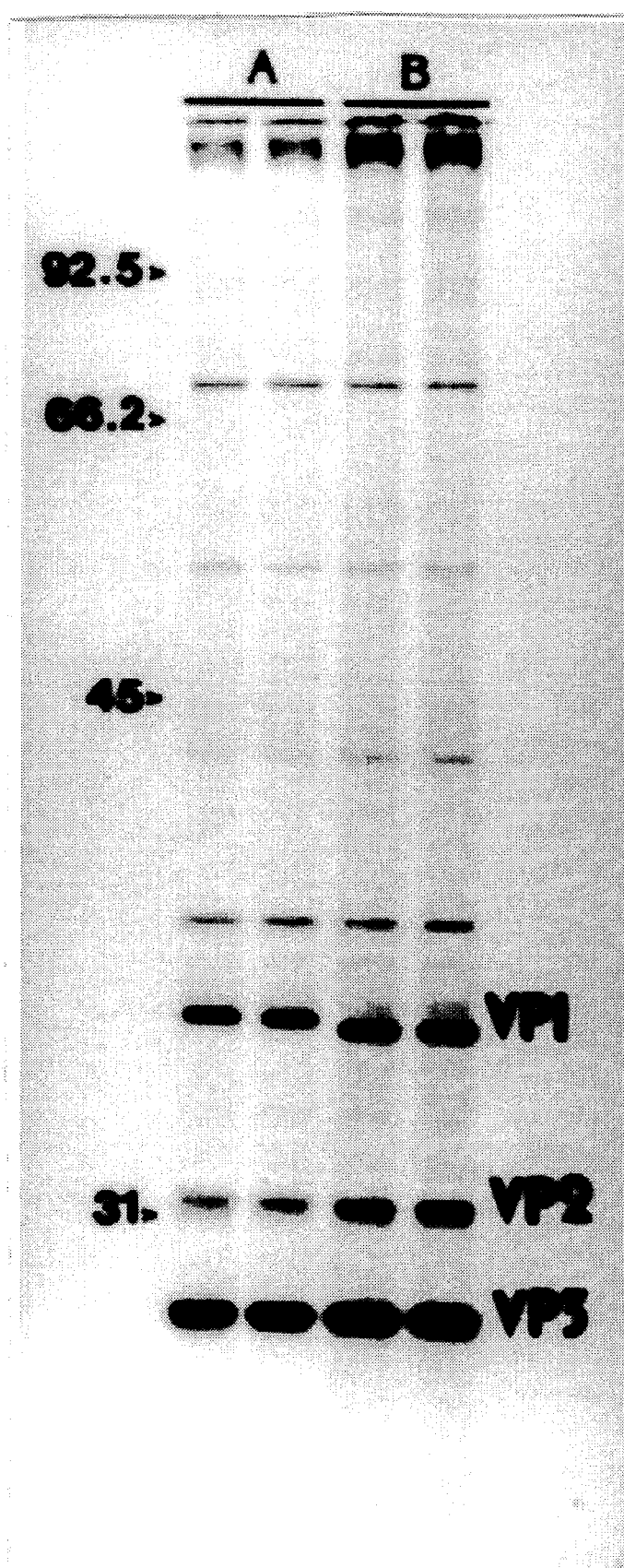

FIG. 8, depicts SDS-polyacrylamide gel electrophoresis of LED3 and VR318 cDNA-derived viruses. A [$^{35}$S]methionine-labeled sample was prepared and loaded in each lane and resolved by eletrophoresis as described hereafter. The gel was dried and the protein bands visualized by autoradiography. LED3 virus in lanes "A"; VR318 virus in lanes "B". The positions of prestained molecular mass markers (kilodaltons) are indicated on the left. Positions of viral capsid proteins are identified on the right.

Figure 9A:
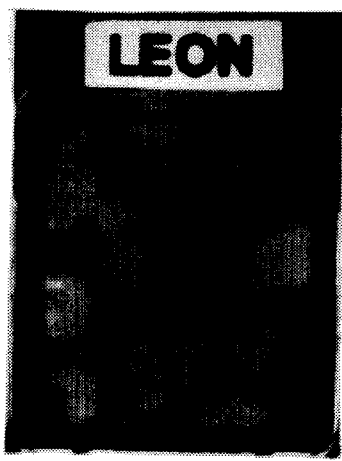
Figure 9B:
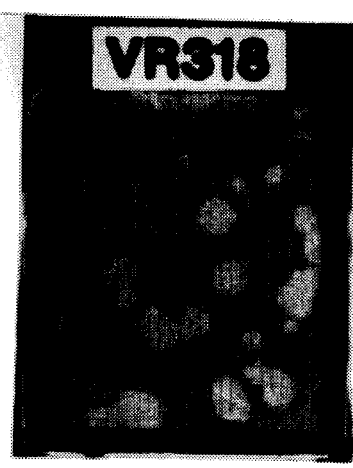
Figure 9C:
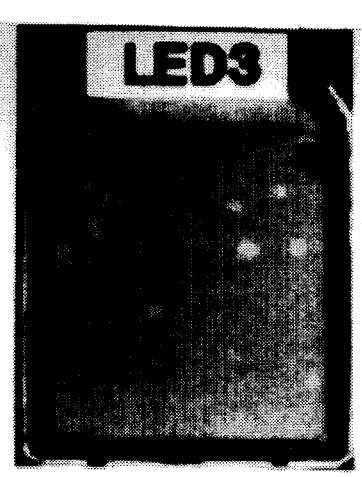

FIGS. 9A–9C depicts plaque phenotype of Leon (wild-type), VR318 and LED3 viruses on Vero cells. After incubation at 33.5° C. for 3 days under 1.0% nutrient agar, cells were stained with neutral red to visualize plaques.

Figure 10:
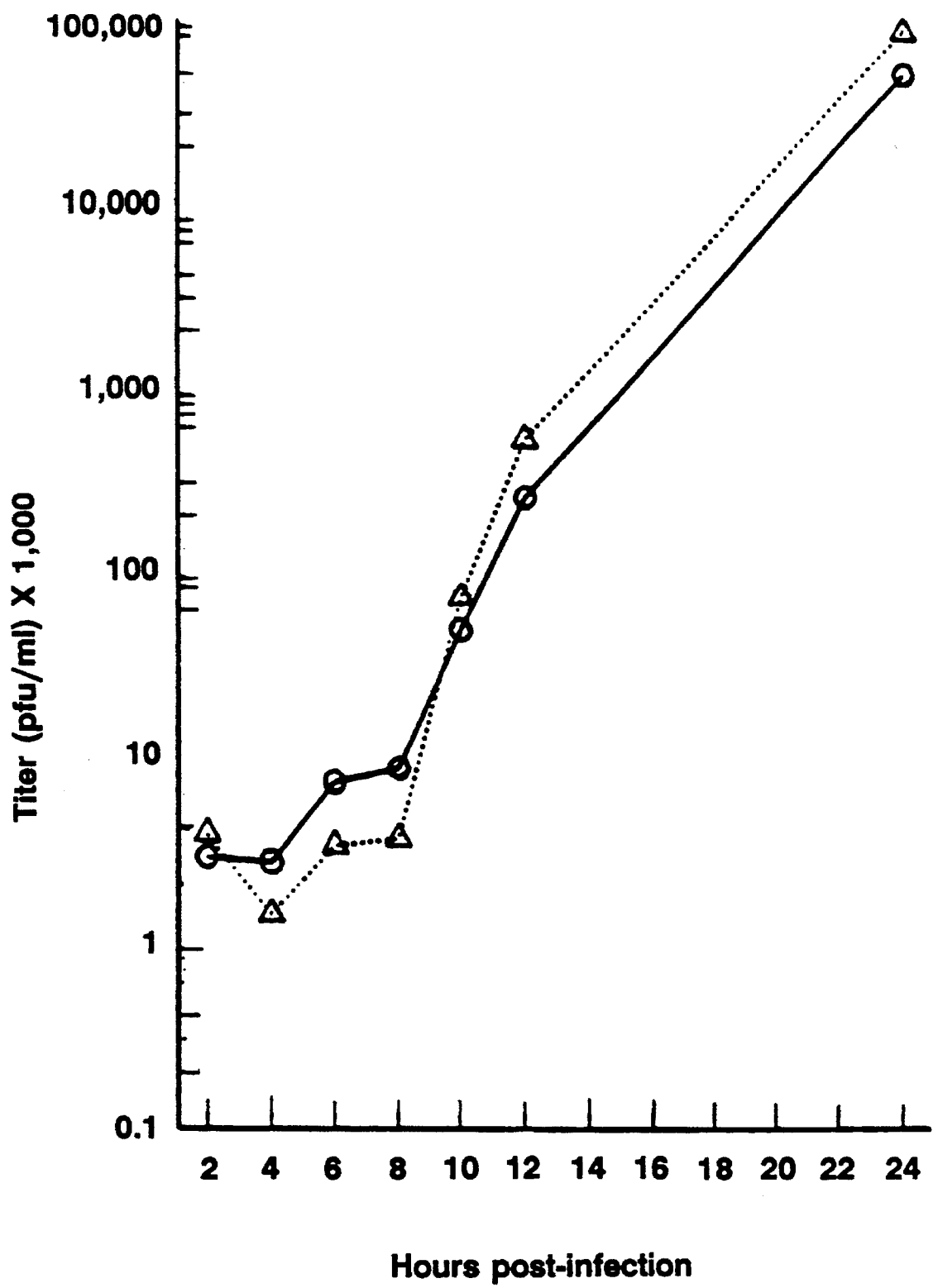

FIG. 10, depicts kinetics of virus growth at 33.5° C. Vero cell monolayers were infected at an MOI of 4, and the extracellular medium was harvested at the indicated times post-infection. Plaque assays were used to determine the titer of infectious particles per ml as described in Materials and Methods, Example 13.

O—O, LED3; ∆- - - - - -∆, VR318.

Figure 11:
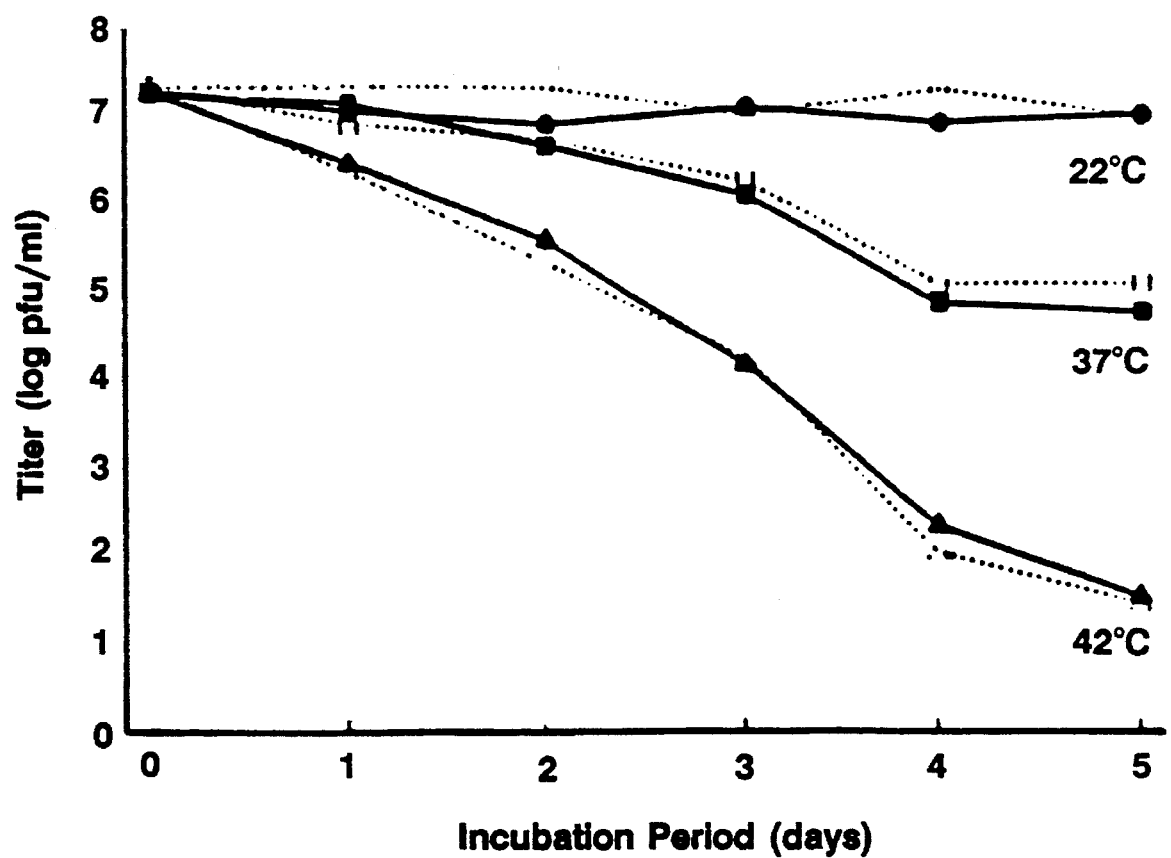

FIG. 11, depicts thermal stability of LED3 and VR318 virus at various temperatures. Virus samples containing approx. $10^{7.3}$ pfu/ml were incubated at 22° C. (circle), 37° C. (square) and 42° C. (triangle). Samples were periodically removed and titer of infectious virus determined by plaque assays. Open markers, LED3; filled markers VR318.

DETAILED DESCRIPTION OF THE INVENTION

This invention provides a method for producing a true RNA virus cDNA comprising the steps of (a) isolating genomic RNA from an RNA source virus; (b) employing RNA sequencing means to determine the nucleotide sequence of a portion of the isolated genomic RNA; (c) employing cDNA synthesis means to produce a double-stranded cDNA from the isolated genomic RNA; (d) employing DNA sequencing means to determine the nucleotide sequence of a portion of the cDNA, wherein the portion of the cDNA corresponds to the portion of the RNA sequenced in step (b); (e) comparing the sequenced cDNA with the sequenced RNA to determine substantive differences in nucleotide sequence; and (f) altering the substantive differences in the cDNA to produce a true RNA virus cDNA.

This invention also provides a method for producing an RNA virus cDNA comprising the steps of a) isolating genomic RNA from an RNA source virus, b) employing RNA seqencing means to determine the nucleotide sequence of a portion of said isolated genomic RNA, c) employing cDNA synthesis means to produce a double-stranded cDNA from said isolated genomic RNA, d) employing DNA sequencing means to determine the nucleotide sequence of a portion of said cDNA, wherein said portion of said cDNA corresponds to said portion of said RNA sequenced in step b), e) comparing said sequenced cDNA with said sequenced RNA to determine substantive differences in nucleotide sequence, and altering said substantive differences in said cDNA to produce an RNA virus cDNA.

This invention also provides the methods described hereinabove, wherein the RNA source virus is a Picornavirus, such as a vaccine strain 3 poliovirus.

In one embodiment of the invention, the portion of RNA sequenced in step (b) comprises nucleotide 2493 of a vaccine strain 3 poliovirus. In a further aspect of this embodiment, the RNA consists of about 100 to 200 nucleotides. Alternatively, the nucleotide sequence of the entire isolated viral RNA is determined in step (b).

This invention further provides a true RNA virus cDNA or an RNA virus cDNA produced by the methods described hereinabove. For example, a true RNA virus cDNA or an RNA virus cDNA may be produced which is derived from a vaccine strain 3 poliovirus, the cDNA being selected from that contained in a novel plasmid designated pLED3.2 or pLED3, respectively or cDNAs which code on expression for the polypeptides coded on for expression by pLED3.2 or pLED3, respectively and the recombinant DNA molecule produced thereby.

The recombinant DNA molecule can be operatively linked to a promoter of RNA transcription. Suitable promoters include, but are not limited to the T7 promoter.

A host transformed with a recombinant DNA molecule described hereinabove is also provided by this invention, wherein the host is selected from the group consisting of bacteria, such as *E. coli,* yeast and other fungi, insect cells and animal cells. Suitable animal cells include, but are not limited to Vero cells, HeLa cells, COS cells, CV-1 cells and primary monkey kidney cells.

Further provided by this invention is a method for producing a viable RNA virus comprising the steps of: (a) culturing a host described hereinabove under conditions which permit the production of viable RNA virus; and (b) harvesting the viable RNA virus from the host cell culture.

This invention provides a method of producing a viable RNA virus comprising the steps of: (a) employing in vitro transcription means to produce RNA from a recombinant DNA molecule described hereinabove (b) isolating the RNA; (c) transfecting a host with the isolated RNA, wherein the host is an animal cell; (d) culturing the host under conditions which permit the production of viable RNA virus; and (e) harvesting the viable RNA virus from the host cell culture. For example, vaccine strain 3 poliovirus may be used and the host may be a primary monkey kidney cell.

This invention further provides a method of producing a viable RNA virus comprising the steps of: (a) transfecting a host with RNA virus cDNA, wherein the cDNA is selected from that contained in the plasmid pLED3 or pLED3.2 or cDNAs which code on expression for the polypeptides coded on for expression by pLED3 or pLED3.2, wherein said host is an animal cell; (b) culturing said host under conditions which permit the production of viable RNA virus from said host cell culture.

This invention further provides an RNA virus, produced by transforming a suitable host cell with a recombinant nucleic acid sequence which encodes for the virus; culturing the host cell under conditions which permit the production of virus; and isolating the virus so produced.

In one embodiment of this invention, the RNA virus may be a vaccine strain 3 poliovirus and the recombinant nucleic acid sequence is a recombinant infectious full length nucleic acid sequence which encodes for the virus; culturing the host cell under conditions which permit the production of virus; and isolating the virus so produced.

In one embodiment of this invention, the RNA virus may be a vaccine strain 3 poliovirus and the recombinant nucleic acid sequence is a recombinant infectious full length nucleic acid sequence which encodes for the vaccine strain 3 poliovirus.

A method of screening for variants of a strain 3 poliovirus is also provided which comprises the steps of: (a) isolating genomic RNA from the poliovirus; (b) employing RNA sequencing means to determine the nucleotide at position 2493.

This invention also provides a method for increasing the attenuation of a strain 3 poliovirus encoded by an RNA virus cDNA, wherein the cDNA comprises the nucleotide sequence ATT at positions 2492 to 2492, the method comprising the step of mutagenizing the cDNA at nucleotide 2493 to change the T to C. In one embodiment of the invention, the method can further comprise the step of mutagenizing the cDNA at nucleotide 2494 to change the T to a nucleotide selected from the group consisting of A, C and G.

This invention provides a vaccine useful for immunizing a subject, for example a human, against infectious poliovirus, wherein the vaccine comprises an effective amount of an RNA virus, produced by transforming a suitable host cell with a recombinant nucleic acid sequence which encodes for the virus; culturing the host cell under conditions which permit the production of virus; and isolating the virus so produced, effective to immunize the subject, and a suitable carrier. The RNA virus may be a vaccine strain 3 poliovirus and the recombinant nucleic acid sequence is a recombinant infectious full length nucleic acid sequence which encodes for the vaccine strain 3 poliovirus.

The recombinant nucleic acid sequence which encodes for the RNA virus may be a DNA sequence, or an RNA sequence or in the preferred embodiment of this invention, the recombinant nucleic acid sequence is a cDNA sequence. Suitable cDNAs are the plasmids designated pLED3.2 or pLED3, each of which contains a promoter linked cDNA nucleic acid sequence which encodes for the vaccine strain 3 poliovirus. The plasmid pLED3 was deposited with the American Type Culture Collection (ATCC), located at 12301 Parklawn Drive, Rockville Md., 20852, under the provisions of the Budapest Treaty on the International Recognition of the Deposit of Microorganisms for the Purposes of Patent Procedure. The plasmid pLED3 was assigned Accession No. 40789. The plasmid pLED3.2 also was deposited with the ATCC under the provisions of the Budapest Treaty and was assigned Accession No.

Suitable host cells include, but are not limited to bacteria, such as *E. coli*, yeast and other fungi, insect cells and animal cells.

Suitable animal cells include, but are not limited to Vero cells, HeLa cells, COS cells, CV-1 cells and primary monkey kidney cells.

The suitable carrier may be a physiologically balanced culture medium, such as aline containing stabilizing agents, for example, dextrose and lactose, or other nontoxic substances. These vaccines may also be formulated with a suitable adjuvant such as alum. For methods of vaccine preparation, see J. I. Duffy, Vaccine Preparation Techniques, Noyes Data Corporation (1980), and G. W. Warr, "Preparation of Antigens and Principles of Immunization", in J. J. Marchalonis and G. W. Warr. eds., Antibody As A Tool—The Applications of Immunochemistry, pp. 21–58, John Wiley & Sons (1982).

The RNA virus may also be desiccated, e.g., by freeze drying for storage or for subsequent formulation into liquid vaccines.

Further provided by this invention is a method of immunizing a subject such as a human against infectious poliovirus, wherein the method comprises administering to the subject a suitable dose of the vaccine described hereinabove. Suitable methods of administering vaccines are well known to those of ordinary skill in the art. However, by way of example, such methods may include but are not limited to intramuscular, intravenous, subcutaneous, intratracheal or intranasal administration.

Additionally, the effective immunizing amount is an amount which is necessary to invoke the production of antibodies by the subject thereby conferring protection on the subject against infectious poliovirus or poliomyelitis.

Throughout this application, references to specific nucleotides in cDNA molecules are to nucleotides present on the coding strand of the cDNA, i.e., the strand which has a sequence equivalent to the position RNA strand of an RNA virus. References to specific nucleotide position numbers in strain 3 poliovirus follow the nucleotide numbering system of G. Stanway et al., "Comparison of the Complete Nucleotide Sequences of the Genomes of the Neurovirulent Poliovirus P3/Leon/37 and its Attenuated Sabin Vaccine Derivative P3/Leon 12a1b", *Proc. Natl. Acad. Sci. U.S.A.*, 81, pp 1539–43 (1984). The following standard abbreviations are used throughout the specification and in the claims to indicate specific nucleotides:

| C - cytosine | A - adenosine |
|---|---|
| T - thymidine | G - guanosine |
| U - uracil | |

The term "source virus" refers to the RNA virus from which RNA is isolated and used as a template for cDNA production. And the term "increased attenuation" is used throughout to indicate a lower rate of reversion to the neurovirulent phenotype than those of conventional vaccine virus strains.

The term "true RNA virus cDNA", as used herein, refers to a cDNA which directs the production of a viable RNA virus that is phenotypically similar to the source virus.

Accordingly, the present invention encompasses cDNA molecules which, by virtue of the redundancy of the genetic code, are characterized by a nucleotide sequence that differs from that of the source virus RNA, but which encode polypeptides having the same amino acid sequences as those encoded by the source virus RNA. The invention also encompasses cDNAs which encode amino acid sequences which differ from those of the source virus polypeptides, but which do not produce phenotypic changes. Hereinafter, these altered, but phenotypically equivalent amino acid sequences are referred to as "equivalent amino acid sequences." And this invention encompasses cDNA molecules characterized by changes in noncoding regions that do not alter the phenotype of the RNA virus produced therefrom when compared to the source virus. Differences between the nucleotide sequence of an RNA virus cDNA and the source virus RNA which result in phenotypical differences in the virus produced therefrom are hereinafter referred to as "substantive differences".

This invention provides a method for producing an RNA virus cDNA comprising the steps of (a) isolating genomic RNA from an RNA source virus, (b) employing RNA sequencing means to determine the nucleotide sequence of a portion of the isolated genomic RNA, (c) employing cDNA synthesis means to produce a double-stranded cDNA from the isolated genomic RNA, (d) employing DNA sequencing means to determine the nucleotide sequence of a portion of the cDNA, wherein the portion of the cDNA corresponds to the portion of the RNA sequenced in step (b), (e) comparing the sequenced cDNA with the sequenced RNA to determine substantive differences in nucleotide sequence, and (f) altering the substantive differences in the cDNA to produce an RNA virus cDNA. In one embodiment of this invention, the RNA virus is a true RNA virus and in another embodiment of this invention the RNA virus is a "phenotypically equivalent" virus. In one embodiment of this invention, the RNA source virus is a Picornavirus, for example a vaccine strain 3 poliovirus.

This invention also provides a method as described hereinabove wherein the portion of RNA sequenced in step (b) comprises nucleotide 2493 of a vaccine strain 3 poliovirus, or preferably, wherein the RNA consists of about 100 to 200 nucleotides.

In another embodiment of this invention, the method described hereinabove wherein the nucleotide sequence of the entire isolated viral RNA is determined in step (b).

The method of this invention may also be used to produce an RNA virus cDNA by altering nucleotides in various regions of the poliovirus genome, for example, to correct mutations introduced into the region coding for the amino terminus of VP1 of the type 1 Mahoney poliovirus [K. Kirkegaard, "Mutations in VP1 of Poliovirus Specifically Affect Both Encapsulation and Release of Viral RNA", *J. Virology*, 64, pp. 195–206 (1990)].

Further provided by this invention is an RNA virus cDNA produced by any of the methods described hereinabove which may include, but is not limited to an RNA virus cDNA derived from a vaccine strain 3 poliovirus, the cDNA being selected from the group consisting of pLED3 or pLED3.2 and cDNAs which code an expression for the polypeptides coded on for expression by pLED3 or pLED3.2.

This invention also provides a recombinant DNA molecule comprising an RNA virus cDNA as described hereinabove, which may include, but is not limited to the recombinant DNA molecule wherein the RNA virus cDNA is operatively linked to a promoter of RNA transcription such as the T7 promoter.

A host transformed with a recombinant DNA molecule described hereinabove is also provided wherein the host is selected from the group consisting of bacteria, yeast and other fungi, insect cells and animal cells. In a preferred embodiment of this invention, the host is an animal cell and is selected from the group consisting of Veto cells, HeLa cells, COS cells, CV-1 cells and primary monkey kidney cells. In another embodiment of this invention, the host is *E. coli*.

This invention further provides a method for producing a viable RNA virus comprising the steps of: culturing a host described hereinabove under conditions which permit the production of viable RNA virus and harvesting the viable RNA virus from the host cell culture. This invention also provides a method of producing a viable RNA virus comprising the steps of employing in vitro transcription means to produce RNA from a recombinant DNA molecule described hereinabove, isolating the RNA, transfecting a host with the isolated RNA, wherein the host is an animal cell, culturing the host under conditions which permit the production of viable RNA virus and harvesting the viable RNA virus from the host cell culture. In the preferred embodiment of this invention, the RNA virus is a vaccine strain 3 poliovirus and the host is a primary monkey kidney cell.

A method of screening for variants of a strain 3 poliovirus is provided by this invention which comprises the steps of isolating genomic RNA from the poliovirus, and employing RNA sequencing means to determine the nucleotide at position 2493.

This invention also provides a method for increasing the attenuation of a strain 3 poliovirus encoded by an RNA virus cDNA, wherein the cDNA comprises the nucleotide sequence ATT at positions 2492 to 2494, and the method comprising the step of mutagenizing the cDNA at nucleotide 2493 to change the T to C. This method may further comprise the step of mutagenizing the cDNA at nucleotide 2494 to change the T to a nucleotide selected from the group consisting of A, C and G.

The determination of phenotypic differences may be carried out by several methods which are well known in the art. Preferably, a true RNA virus cDNA of an attenuated strain 3 poliovirus encodes a virus which has the same degree of attenuation as the source virus. Several well characterized markers can be used to determine phenotypic changes in a strain of poliovirus. These are the "d" markers, which regulate the ability of the virus to grow under acid conditions [M Vogt et al., "Mutants of Poliomyelitis Viruses with Reduced Efficiency of Plating in Acid Medium and Reduced Neuropathogenicity", *Virology*, 4, pp 141–55 (1957)]; and the "rct$_{40}$" marker, which regulates the ability of the virus to grow at elevated temperatures [A. Lwoff, "Factors Influencing the Evolution of Viral Diseases at the Cellular Level and in the Organism", *Bact. Rev.*, 23 pp. 109–24 (1959)].

The most preferred method of determining phenotypic changes between an attenuated strain 3 source poliovirus and the virus produced from its true RNA virus cDNA is a comparison of neurovirulence. Several protocols for assessing neurovirulence are known in the art [Code of Federal Regulations, Title 21, Chapter 1, pp. 91–93 (Apr. 1, 1987 edition)].

Production of a True RNA Virus cDNA

According to one embodiment, the present invention relates to a method for producing true RNA virus cDNA. The production of a true RNA virus cDNA according to this invention may employ any RNA source virus—positive single-stranded, negative single-stranded, or double-stranded. Preferably, the source virus is a positive single-stranded virus. More preferably, the virus is a human enterovirus belonging to the family Picornaviridae. Most preferred is an attenuated type 3 vaccine strain poliovirus (also referred to herein as "P3/Sabin").

A. Proliferation and Isolation of Virus

The initial step in the production of true RNA virus cDNA involves the proliferation and purification of the source virus and the isolation of RNA therefrom. Techniques for proliferating and isolating virus are well known in the art [R. J. Kuchler, "Biochemical Methods in Cell Culture and Virology", Dowden Hutchinson and Ross, Inc., Stroudsburg, Pa. (1977)]. It will be understood that the method of viral growth, including choice of host cell, selection of growth medium, and conditions of growth, will differ depending upon the particular source virus. In a preferred embodiment, attenuated strain 3 poliovirus is proliferated in primary monkey kidney cells according to known methods [A. Sabin et al., "Studies On Variants Of Poliomyelitis Virus", *J. Exp., Med.*, 99, pp. 551–76 (1954)]. The following procedures are applicable for any strain of poliovirus. However, the use of an alternate RNA source virus in these procedures may require certain virus-specific modifications which are known to those of skill in the art.

Viral proliferation of the RNA virus is allowed to proceed to a point where a sufficient quantity of virus can be harvested for RNA isolation. The culture media containing the source virus is then collected and cellular debris is removed, preferably by centrifugation at a speed which will not pellet the virus. This is typically about 2,500 rpm for about 20 minutes. The supernatant may then be further purified by ultrafiltration employing a filter having a pore size that is larger than the viral particles. Preferably, a filter of approximately 0.22 µM is used.

Following filtration, the viral particles are collected by polyethylene glycol precipitation followed by centrifugation or, more preferably, by high speed centrifugation at about 70,000 rpm. The viral particles are then resuspended in a small volume of buffer, preferably TNE (10 mM Tris-HCl, 100 mM NaCl, 1 mM EDTA, pH 7.4). A non-ionic detergent may optionally be added to the viral particle suspension to dissolve any contaminants. Although the high speed viral pellet is sufficiently pure to use as a source of viral RNA the viral suspension may optionally be further purified by sucrose density gradient centrifugation.

If density gradient centrifugation is employed, fractions are collected from the gradient and analyzed for the presence of source virus. Any conventional assay which detects source virus-specific proteins may be employed. Such assays include, for example, Western blots, ELISA, radio-immunoassay, or polyacrylamide gel electrophoresis and comparison to a source virus standard. The latter technique is most preferred because it is the most economical.

B. Isolation and Sequencing of Viral RNA

Once the virus is purified as described above, viral RNA may then be isolated. This is achieved by first dissociating the viral capsid proteins by treatment with detergent, preferably sodium dodecyl sulfate ("SDS") at a final concentration of 0.5%. The dissociated proteins are then extracted by treatment of the sample with organic solvents. Extraction is preferably achieved with a phenol:chloroform:isoamyl alcohol mixture. The RNA present in the aqueous phase may then be isolated by any method well known in the art [T. Maniatis, "The Molecular Guide To Cloning", Cold Spring Harbor Press (1983)]. Preferably, the viral RNA is precipitated with 0.5 volumes of 7.5M ammonium acetate and 2.5 volumes of ethanol at −20° C. Quantitation and integrity of the viral RNA may be determined by agarose gel electrophoresis. It should be noted, as is well known in the molecular biology art, that great care must be taken in the preparation and handling of RNA samples due to the prevalence of RNases. Methods for inactivating RNases that may be present in reagents and in vessels used in RNA preparation are well known [T. Maniatis, supra].

Once the source virus RNA has been isolated, it is subjected to dideoxy nucleotide sequencing [F. Sanger et al., "DNA Sequencing With Chain-Terminating Inhibitors", *Proc. Natl. Acad. Sci. USA,* 74:5463–67 (1977)] employing modifications for RNA [D. C. Deborde et al., "Resolution Of A Common RNA Sequencing Ambiguity By Terminal Deoxynucleotidyl Transferase", *Anal. Biochem.,* 157, pp. 275–82 (1986)]. According to a preferred embodiment of this invention, the entire RNA genome of the virus is sequenced and compared to the cDNA sequence by methods which are hereinafter described. In this embodiment of the invention the source virus is most preferably an attenuated type 3 vaccine strain poliovirus.

C. Synthesis and Screening of an RNA Virus cDNA Library

Following RNA sequencing, the source virus RNA is used as a template for the synthesis of a full-length, double-stranded cDNA. Any well-known method or commercially available cDNA synthesis kit is employed to synthesize cDNA. Preferably, cDNA is synthesized by the method of V. R. Racaniello et al., "Molecular Cloning Of Poliovirus cDNA And Determination Of The Complete Nucleotide Sequence Of The Viral Genome", *Proc. Natl. Acad. Sci. USA,* 78, pp. 4887–91 (1981). For ease of detection, the first strands of cDNA may optionally be radiolabeled by employing a radioactive nucleotide during cDNA synthesis. Once synthesized, the single-stranded cDNA are preferably size-fractionated either by agarose gel electrophoresis or, more preferably, by gel chromatography. The larger cDNAs are isolated and used as templates for second-strand synthesis. Double-stranded cDNA is then size-fractionated as described above and the largest molecules are used for the creation of a source virus cDNA library. The cDNA are then tailed, either by the olio dG/dC method or by the addition of restriction enzyme linkers, and cloned into an appropriate vector. The choice of vector will be based upon the technique that will be employed to screen the library. For example, the use of an immunoscreening technique requires that the cDNA be inserted into an expression vector, such as lambda gt11 (ATCC accession number 37194). If a hybridization screening method is employed, vectors such as bacterial plasmids are most convenient. Preferably, the cDNA are tailed by the olio dG/dC method and cloned into the PstI site of pBR322.

Once the RNA virus cDNA library is created, it is screened for a full-length cDNA clone. This may be achieved by well-known screening methods, such as antibody screening or hybridization to a labeled probe. Most preferably, the library is screened by colony hybridization using virus-specific cDNA probes [M. Grunstein et al., "Colony Hybridization: A Method for the Isolation of Cloned DNAs That Contain A Specific Gene", *Proc. Natl. Acad. Sci. USA,* 72, pp. 3961–65 (1975)], based on known nucleotide sequences or amino acid sequences of the virus. Once a clone containing an RNA virus cDNA has been identified and isolated, it may be removed from the vector and analyzed to determine whether it represents a full-length RNA virus cDNA. In a preferred embodiment of the invention, the dC-tailed cDNA is removed from a PstI cut, dG-tailed vector by digestion with PstI. Partial cDNAs may be used to reprobe the library and to locate longer, or full-length cDNAs. If no full-length cDNAs can be detected, several overlapping partial cDNAs representing the entire source virus genome may be ligated together at common restriction sites to produce a full-length cDNA [V. R. Racaniello et al., "Cloned Poliovirus cDNA Is Infections In Mammalian Cells", *Science,* 214, pp. 916–19 (1981)]. Any portion of the viral genome which is not represented by an isolated cDNA may be synthesized using standard oligonucleotide synthesizing techniques and subsequently ligated into its proper position to form a full-length cDNA.

D. Sequencing and Alteration of cDNA to Correspond to Source Virus RNA

Portions of the full-length cDNA corresponding to the sequenced portion of the source virus RNA are then sequenced by standard DNA sequencing methods. The sequenced regions of the viral RNA and the RNA virus cDNA are then compared. Theoretically, the cDNA should correspond exactly to the RNA which served as its template. However, it is known that reverse transcriptase can produce errors when transcribing cDNA from RNA [I. M. Verma, "Reverse Transcriptase", In *The Enzymes, Vol.* 14, P. D. Boyer, ed., Academic Press, New York, pp. 87–104 (1981)]. Therefore, according to the method of this invention, it is necessary to alter the nucleotide sequence of the cDNA so that it corresponds to the sequenced RNA.

The present invention contemplates altering the cDNA sequence at those sites which are responsible for phenotypic changes. Accordingly, portions of the cDNA which encode polypeptides having equivalent amino acid sequences as those encoded by the source virus RNA need not be altered.

Preferably, any cDNA nucleotide mutation which may potentially affect virus production or viral polypeptide synthesis should be altered to correspond to the source virus RNA.

Methods for altering the nucleotide sequence of a cDNA molecule are known in the art and include site-directed mutagenesis [C. A. Hutchinson, III et al., "Mutagenesis At A Specific Position In A DNA Sequence", *J. Bio. Chem.,* 253, pp 6551–60 (1978); A. Razin et al., "Efficient Correction Of A Mutation By Use Of A Chemically Synthesized DNA", *Proc. Natl. Acad. Sci., USA,* 75, p. 4268 (1978)]. Alternatively, a partial cDNA clone containing the desired sequence may be isolated from the cDNA library and its DNA, or a portion thereof, substituted in the full-length clone for the sequences which are to be altered. Once the cDNA sequence has been altered, it is utilized in other embodiments of this invention.

According to another embodiment of the present invention, the true RNA virus cDNA may be inserted into an appropriate vector and used to transform an appropriate host. The choice of vector will depend upon the ultimate intended use of the cDNA. Similarly, the choice of host will depend upon both the vector selected and the ultimate goal of transformation.

For example, if it is desirable to simply store the cDNA and create and unlimited supply thereof, the cDNA will be inserted into a vector which is capable of transforming a unicellular organism, such as a bacteria, yeast or other fungi, an animal cell or an insect cell. According to one embodiment of this invention, the cDNA is inserted into the PstI site of pBR322 and the host to be transformed is E. coli.

According to another embodiment of the invention, the true RNA virus cDNA may be operatively linked to a promoter of transcription. As used herein, the term "operatively linked" means positioned in such a manner that the promoter will direct the transcription of RNA off of the true virus cDNA. Examples of such promoters are SP6, T4 and T7. The most preferred promoter is the T7 promoter [J. J. Dunn et al., "Complete Nucleotide Sequence of Bacteriophage T7 DNA and the Locations of T7 Genetic Elements", *J. Mol. Biol.*, 166, pp. 477–535 (1983)]. Vectors which contain both a promoter and a cloning site into which an inserted piece of DNA is operatively linked to that promoter are well known in the art. Preferably, these vectors are capable of transcribing RNA in vitro. Examples of such vectors are the pGEM series [Promega Biotec, Madison, Wis.].

According to a further embodiment, the present invention relates to methods for producing viable positive stranded RNA virus. This may be achieved by transfecting an appropriate host with a true RNA virus cDNA. Any standard method of transfecting animal cells with DNA may be employed [F. M. Ausubel et al., "Current Protocols in Molecular Biology", Greene Publishing Associates & Wiley Intersciences (1987)]. The host is then cultured under conditions conductive to the production of RNA virus. Such conditions are well known in the art and will vary depending upon the virus to be produced. Similarly, the choice of host cell should be one which is compatible with the virus, preferably primate cells in culture. In a preferred embodiment of the invention, wherein the true RNA virus cDNA encodes an attenuated strain 3 poliovirus, the host is selected from the group consisting of Vero cells, HeLa cells, COS cells, CV-1 cells, human diploid cell lines, such as WI-38 and MRC5, and primary monkey kidney cells. The most preferred hosts are monkey kidney cells. Once the cells have produced a desirable level of virus, the virus is harvested from the cell culture according to standard protocols.

According to an alternative embodiment of this invention, viral RNA, which is produced by in vitro transcription of a true RNA virus cDNA according to the invention, may be employed in methods for producing viable RNA virus. The in vitro transcribed RNA is isolated by standard methods and used to transfect an appropriate host. The use of RNA to transfect cells is known in the art [S. van der Werf et al., "Synthesis of Infectious Poliovirus RNA by Purified T7 RNA Polymerase", *Proc. Natl. Acad. Sci. USA*, 83, pp. 2330–34 (1986)]. Once the cells are transfected, they are grown and the virus harvested according to standard protocols.

According to another embodiment, this invention relates to a method of screening for variants of a strain 3 poliovirus. Through RNA sequencing, it was discovered that the presence of a C at nucleotide position 2493 of this virus is linked to the attenuated strain 3 genotype. Previous analyses of this strain failed to recognize the importance of this position in attenuation due to a combination of two factors: the sequences of wild-type and attenuated strain 3 poliovirus were compared on the cDNA level, rather than the genomic RNA level; and some of these cDNAs were made from plaque isolates of the original viral samples [Stanway et al., "Comparison of the Complete Nucleotide Sequences of the Genomes of the Neurovirulent Poliovirus P3/Leon/37 and its Attenuated Sabin Vaccine Derivative P3/Leon 12a1b", *Proc. Natl. Acad. Sci. USA*, 81, pp. 1539–43 (1984); H. Toyoda et al., "Complete Nucleotide Sequences of All Three Poliovirus Serotype Genomes", *J. Mol. Biol.*, 174, pp. 561–85 (1984)]. As a result of either errors in reverse transcription or mutations resulting from virus passaging, the cDNAs previously produced contained a T at position 2493. Therefore, the RNA of type 3 vaccine strain of poliovirus was mistakenly believed to contain U at this position, the same nucleotide present in the wild-type strain [Stanway et al., supra; H. Toyoda et al., Supra]. Accordingly, position 2493 was never thought to contribute to the attenuation of the poliovirus strain 3 genome.

Therefore, the method of screening for variants of a strain 3 poliovirus according to this invention comprises the steps of sequencing the RNA of the virus and determining the nucleotide at position 2493. Most preferably, the portion of RNA to be sequenced consists of about 100–200 nucleotides flanking nucleotide 2493. This method may be used during amplification of the source virus (e.g., in vaccine production) to ensure maintenance of C at position 2493 in the viral genome.

This invention also relates to a method for increasing the attenuation of a strain 3 poliovirus produced from a true RNA virus cDNA, wherein the cDNA comprises the sequence ATT at positions 2492–2494. The method comprises mutagenizing the nucleotide at position 2493 from a T to a C and subsequently using the mutagenized cDNA to produce viable virus. The presence of a C instead of a U at position 2493 of strain 3 poliovirus RNA would be expected to alter the sixth amino acid of the viral capsid protein, VP1, from isoleucine to threonine, based on the genetic code. The condon encoding this amino acid spans nucleotides 2492–2494. Therefore, the method for increasing the attenuation of strain 3 poliovirus according to this invention may also include mutagenizing nucleotide 2494 from a T to either A, C or G.

In order that the invention described herein may be more fully understood, the following examples are set forth. It should be understood that these examples are for illustrative purposes only and are not to be construed as limiting this invention in any manner.

EXAMPLE 1

Purification Of A Strain 3 Poliovirus

All glassware utilized in the methods described below is either sterilized or treated with diethyl pyrocarbonate (DEP) to destroy RNases. All reagents are made up with water that had been treated with DEP prior to use.

Primary monkey kidney cells are infected with an attenuated strain 3 poliovirus, isolated by plaque purification from the "ORIMUNE" vaccine (Lederle Laboratories, Pearl River, N.Y.), at a low multiplicity of infection ("MOI"). The infected cultures are maintained at 34° C. in modified Earle's lacteal maintenance medium, pH 7.3, until the cell monolayer is destroyed (+4 cytopathic effect ("CPE")). The culture media (120 ml) is collected and centrifuged at 2,500 rpm for 20 minutes to remove any cellular debris. The supernatant is then filtered through a 0.22 µM Millex GV disc filter. The filtrate is then placed in quick seal high speed centrifuge tubes and spun in a 70.1 Ti rotor at 70,000 rpm for one hour at 4° C.

The virus pellet is resuspended in 4 ml of RNase-free TNE (10 mM Tris-HCl, 100 mM NaCl, 1 mM EDTA, pH 7.4) and the suspension transferred to a 15 ml polypropylene tube. The viral capsid are then dissociated by the addition of RNase-free SDS to a final concentration of 0.5%.

EXAMPLE 2

Isolation And Sequencing of Viral RNA

Viral RNA is then isolated by extracting the dissolved capsid as prepared in Example 1, with an equal volume of phenol:chloroform:isoamyl alcohol (25:24:1). The aqueous layer is removed and re-extracted with the same organic solution. One-half volume of 7.5M ammonium acetate and 2.5 volumes of 100% ethanol is added to the aqueous extract and the RNA is precipitated at −20° C. for at least 30 minutes. The RNA is then pelleted by centrifugation at 12,000 rpm for 30 minutes. The RNA pellet is washed twice with ice-cold 70% ethanol, dried under vacuum and resuspended in 20 µM of water. The integrity and concentration of the RNA is estimated by using agarose gel electrophoresis.

The viral RNA is then sequenced essentially by the method of DeBorde [D. C. Deborde et al., *Anal. Biochem.*, 157, pp. 275–82 (1986)], the disclosure of which is incorporated herein by reference. The specific details of sequencing are described below.

Approximately 500 mg of purified viral RNA is heat denatured at 100° C. for 3 minutes in 200 mM Tris-HCl, pH 8.3, 200 mM KCl, 20 mM $MgCl_2$, 10 mM DTT and then quick-chilled by immersion into an ice bath. Primer, dATP and enzymes are then mixed in with the RNA, as described by DeBorde et al. Two and one-half µl of primer-RNA mix is then combined with an equal volume of various reaction mixes, in separate tubes, to give the following component concentrations:

Tube A: 50 mM Tris-HCl, pH 8.3, 50 mM KCl, 5 mM MgCl, 10 mM DTT, 100 µM each of dCTP, dGTP and dTTP, 5 µCi [$^{35}$S]-dATP, 1.25 µM ddATP, 100 ng RNA, 15 ng primer and 2.8 units reverse transcriptase;

Tube C: same as tube A, except 20 µM dCTP, 2.5 µM ddCTP and no ddATP;

Tube G: same as tube A, except 20 µM dGTP, 3.0 µM ddGTP and no ddATP;

Tube T: same as tube A, except 20 µM dTTP, 7.5 µM ddTTP and no ddATP;

Tube N: same as tube A, except no ddATP.

Each tube is incubated at 42° C. for 20 minutes. Following this incubation, 1 µl of chase solution (1 mM each of dATP, dCTP, dGTP and dTTP and 2 units of terminal deoxynucleotidyl transferase) is added to each tube and the tubes incubated for another 30 minutes at 37° C. The reactions are stopped by freezing at −20° C. Prior to electrophoresis, 5 µl of formamide dye mixture is added to each tube. The samples are then heated to 100° C. for 3 minutes and 5 µl of each sample is loaded per gel lane.

The sequencing gels (35 cm×13 cm×0.1 mm) are 6% polyacrylamide (38:2; acrylamide:bis-acrylamide) containing 7M urea in TBE (89 mM Tris, 89 mM boric acid, 2 mM EDTA).

When the complete sequence of the attenuated strain 3 poliovirus RNA genome is compared to the published P3/Sabin cDNA sequence [Stanway et al., *Proc. Natl. Acad. Sci. USA*, 81, pp. 1539–43 (1984)], two nucleotide differences are observed, one of which causes an amino acid change. These are shown in the following table:

| Nucleotide Position | P3/Sabin Stanway | P3/Sabin RNA | Amino Acid Change |
|---|---|---|---|
| 2493 | T | C | Ile to Thr (VPI) |
| 6061 | C | U(T) | silent |

The difference observed at position 2493 is important for several reasons. First, it encodes a significant amino acid change in the viral capsid protein VP1. Moreover, because wild-type strain 3 poliovirus has a U at this position (T in the cDNA), the purported presence of a T at 2493 of the attenuated strain 3 poliovirus cDNA may have obscured a significant difference between the wild-type and attenuated genomes.

EXAMPLE 3

Synthesis Of A Full-Length Poliovirus cDNA

The vital RNA obtained in the previous Example is used as a template for the synthesis of a double-stranded cDNA using the method of V. R. Racaniello et al., "Molecular Cloning Of Poliovirus cDNA And Determination Of The Complete Nucleotide Sequence Of The Viral Genome", *Proc. Natl. Acad. Sci. USA*, 78, pp. 4887–91 (1981). Specifically, 2.5 μg of vital RNA is used to produce first strand cDNA in a 100 μl reaction containing 50 mM Tris-HCl, pH 8.3, 10 mM $MgCl_2$, 50 mM KCl, 0.5 mM each of dATP, dTTP, dGTP and dCTP, 0.4 mM DTE, 30 μg/ml olio dT (12–18 nucleotides in length), 4 mM sodium pyrophosphate, 10 μCi/μl [α-$^{32}$P]-dATP, 1 unit/μl RNasin and 2 units/μl reverse transcriptase [Boehringer-Mannheim, Indianapolis, Ind.]. The reaction is incubated at 42° C. for 60 minutes. The reaction is stopped by the addition of EDTA to a final concentration of 50 μM. The solution is then phenol extracted and the aqueous layer applied to a 5×0.7 cm Sepharose CL-4B column. The column is developed with 0.3M NaCl, 10 mM Tris-HCl, pH 8.0, 1 mM EDTA. The profile thus obtained is depicted in FIG. 1.

Fractions 5–13 are pooled from the column and 20 μg of glycogen is added thereto. The cDNA is then precipitated at −20° C. by the addition of 2.5 volumes of ethanol, pelleted by centrifugation and resuspended in 25 μl of 10 mM Tris-HCl, pH 8.0, 1 mM EDTA (TE) for use in second strand synthesis.

Second strand synthesis is performed in a 100 μl reaction containing the single-stranded cDNA, 20 mM Tris-HCl, pH 7.4, 7 mM $MgCl_2$, 0.1M KCl, 50 μg/ml bovine serum albumin (BSA), 0.1 mM of each dNTP, 150 μM β-NAD, 5 μg/ml *E. coli* DNA ligase, 250 units/ml *E. coli* DNA polymerase I and 90 units/ml RNase H. The mixture is incubated at 15° C. for 60 minutes followed by 90 minutes at room temperature. The cDNA is then phenol extracted and chromatographed over Sepharose CL-4B as described above. The void volume fractions are pooled, precipitated with ethanol and resuspended in 25 μl TE, as described previously.

The resulting double-stranded cDNA is tailed with deoxycytidine (dC) in a 100 μl reaction containing 140 mM K-cacodylate, pH 7.2, 30mM Tris-HCl, 1mM $CoCl_2$, 1 mM DTT, 50 μg/ml BSA, 150 μM dCTP and 800 units/ml terminal deoxynucleotidyl transferase. The reaction is incubated at 37° C. for 60 minutes and the solution is then phenol extracted. The aqueous layer is removed, ether extracted and the tailed cDNA is precipitated therefrom with ethanol containing 20 µg glycogen. The resulting pellet is suspended in 50 µl of 10 mM Tris-HCl, pH 7.5, 100 mM NaCl, 1 mM EDTA (NTE).

EXAMPLE 4

Production Of A Poliovirus cDNA Library

Increasing amounts (1, 2, 5, 10 µl) of dC-tailed, double-stranded cDNA, produced as in Example 3, are annealed to 10 ng of PstI-cleaved, dG-tailed pUC9 (Pharmacia, Piscataway, N.J.) in NTE by heating the mixture to 68° C. in a water bath for 5 minutes, cooling the mixture in a 42° C. water bath and then slowly decreasing the temperature to room temperature overnight by shutting off the water bath. This allows for optimal hybridization between the dC tails on the cDNA and the dG tails on pUC9. The annealed mixtures are then used to transform E. coli DH5α cells (Bethesda Research Labs, Gaithersburg, Md.) using standard procedures. Ampicillin-resistant colonies are selected for screening.

EXAMPLE 5

Isolation Of Poliovirus Clones

Bacterial colonies are picked onto gridded plates and screened by colony hybridization, using linearized plasmid pOLIO (Sabin) as a probe [J. W. Almond et al., "Attenuation and Reversion to Neurovirulence of the Sabin Poliovirus Type-3 Vaccine", In *Vaccines*, 85, Cold Spring Harbor Laboratory, Cold Spring Harbor, N.Y., pp. 271–77 (1985)]. Plasmid pOLIO (Sabin) is a plasmid containing a full-length cDNA derived from P3/Leon 12a$_1$b [G. Stanway et al., *Proc. Natl. Acad. Sci., USA*, 81, pp. 1539–43 (1984)]. Of the 600 colonies screened by hybridization, 140 give positive hybridization signals. Small cultures (5 ml; LB media+ ampicillin) of each of these positive clones are prepared and the plasmid DNA is isolated by the rapid boiling method [T. Maniatis et al., *Molecular Cloning: A Laboratory Manual*, Cold Spring Harbor Laboratory (1982)]. The isolated plasmids are cleaved with PstI, which is predicted to excise the cloned insert. Of the 140 clones which are analyzed in this way, the vast majority contain either small inserts (<1 kb) or do not release inserts upon cleavage with PstI. We are, however, able to identify and map three cDNA clones to the P3/Sabin genome (pLL3-51, 69 and 82; see FIG. 2). Eight hundred colonies are screened by colony hybridization using anEcoRI fragment of pOLIO(Sabin) cDNA, which contains the 5'-most 747 nucleotides, as a probe. Of the thirty-three colonies that hybridize to the probe, five of the cDNAs represent nucleotides 85–779 of P2/Sabin. The origin of these cDNA clones is not known.

Subsequently, additional cDNA is annealed to pUC9 and transformed into DH5α cells. Eight hundred colonies are screened by colony hybridization using full-length pOLIO (Sabin) cDNA as a probe. Twenty-nine positive clones are analyzed by restriction enzyme cleavage. Eight of the positive clones that contain cDNA inserts are subjected to nucleotide sequencing from either end of the inserted DNA. Five of these clones (pLL3-239, 251, 253, 254 and 255) contains a cDNA that maps to the 3'-end of the P3/Sabin genome (FIG. 2).

Figure 1:
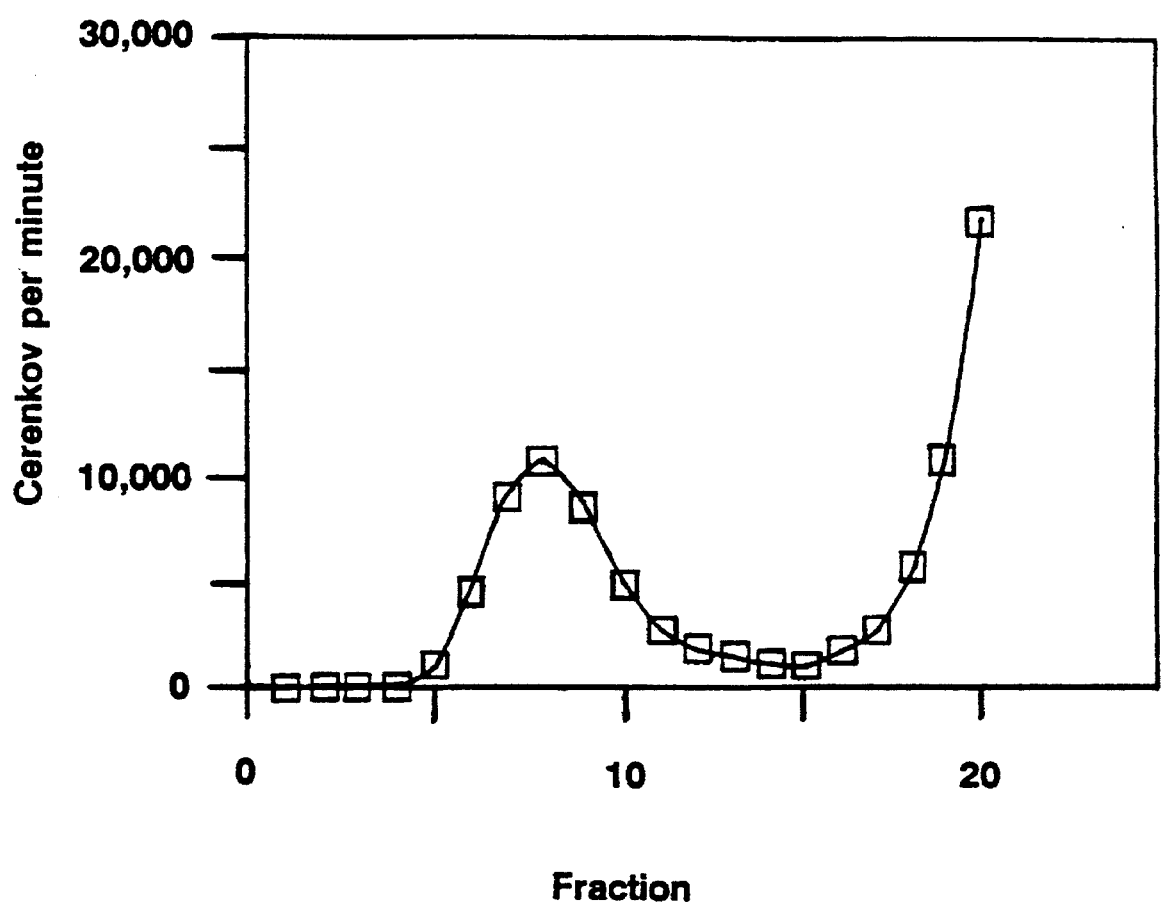
FIG. 1 depicts a chromatographic profile of first-strand cDNA synthesized from poliovirus strain 3 RNA off a Sepharose CL-4B column.
Figure 2:
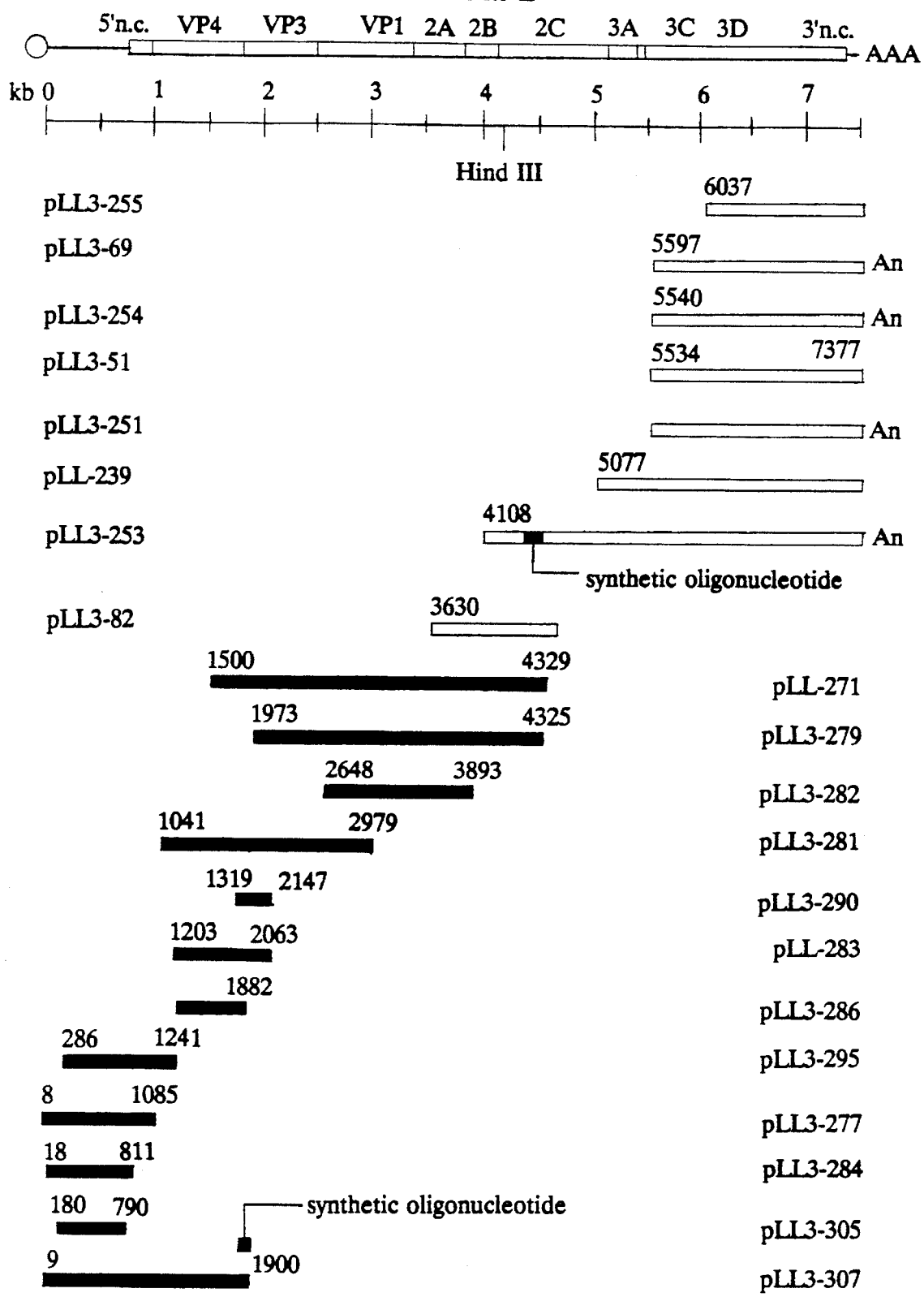
FIG. 2 depicts the cDNA clones which mapped to the P3/Sabin genome.

As depicted in FIG. 2 (open bars), the 8 isolated and analyzed cDNA clones represent nucleotidase 3630 through the 3'-end of the P3/Sabin viral RNA genome.

To obtain additional 5'-cDNA clones, an oligonucleotide complementary to a stretch of bases from nucleotide 4317–4334 (see black shading in FIG. 2, pLL3-253) is synthesized. This oligonucleotide is used to prime cDNA synthesis on P3/Sabin viral RNA isolated according to Example 2 using cDNA synthesis methods described in Example 3. The resulting cDNAs are dc-tailed and cloned into PstI-cut, dG-tailed pUC9. The resulting plasmids are then used to transform DH5α cells. Transformants are screened by hybridization to pOLIO (Sabin 3). Eleven positive cDNA clones are isolated, analyzed by restriction enzyme digestion and sequenced (FIG. 2, black boxes). The eleven clones correspond to nucleotides 6 through 4329 of the P3/Sabin viral RNA.

Although cDNA clones representing all but the first 5 nucleotides of the P3/Sabin genome are identified, attempts to ligate together several of the 5'-cDNAs into a single cDNA proved difficult, due to the lack of convenient restriction sites. Therefore, one final round of cDNA cloning is undertaken in an attempt to obtain a single cDNA clone that represented approximately nucleotides 1 through 1900.

An oligonucleotide complementary to bases 1904–1922 is synthesized and used to prime cDNA synthesis on P3/Sabin RNA. The cDNA is then dC-tailed, inserted into dG-tailed, PstI-cut pUC9 and the resulting plasmid is used to transform DH5α cells. The transformants are again screened with pOLIO (Sabin 3). One of the resulting cDNA clones is identified as containing nucleotides 9–1900 of the viral RNA (FIG. 2, pLL3-307). This completes the cDNA cloning of the P3/Sabin genome.

EXAMPLE 6

Construction Of A Full-Length Poliovirus cDNA

The strategy for assembling the P3/Sabin cDNAs into a single full length cDNA is depicted in FIG. 3. First, clones pLL3-253 and pLL3-271 are assembled into a single clone by using a common HindIII site at nucleotide 4241. The resulting cDNA clone, which represents nucleotides 1500 through the 3' poly(A) of the genome, is called pLL3-I.

Next, the first 5 nucleotides of the P3/Sabin viral genome, which are missing from cDNA pLL3-277, are synthesized. This is achieved by synthesizing two complementary oligonucleotides using an automated oligonucleotide synthesizer and then annealing the oligonucleotides to one another. The resulting double-stranded oligonucleotide comprising from 5' to 3', a PstI site, nucleotides 1 through 34 of P3/Sabin cDNA and a BgeI sticky end, is then used to replace the 5'-most PstI/BglI fragment of pLL3-277. This results in a cDNA clone that represents nucleotides 1–1085. This clone is called pLL3-II.

The final step is the ligation of three SacI fragments representing nucleotides 1–747, 747–1895 and 1895 through the 3'-end, to form a full length P3/Sabin cDNA (termed pLL3-FL). This construction is performed in several separate steps using appropriate cDNA inserts from pLL3-II, pLL3-307 and pLL3-I.

EXAMPLE 7

Sequence Analysis Of The P3/Sabin cDNA

Sequence analysis of P3/Sabin cDNAs used to construct the full length cDNA is performed using three approaches. In the first approach, cDNAs are subcloned into M13 vectors. Nested deletions of the subcloned cDNA, using exonuclease III and mung bean nuclease [E. Ozkaynak et al., "A Unidirectional Deletion Technique for the Generation of Clones for Sequencing, *Biotechniques,* 5, pp. 770–73 (1987)], are then isolated and their nucleotide sequences determined.

In the second approach, cDNAs are isolated and digested with the RsaI. The resulting fragments are then "shotgunned" into M13 for sequence analysis. The last approach utilizes cDNA fragments that are isolated from clones and subcloned into M13 for sequence analysis.

Upon nucleotide sequencing of the entire P3/Sabin cDNA clone, 3 differences are found when the cDNA sequence is compared to the RNA sequence. These differences are summarized in the following table:

| Nucleotide Position | P3/Sabin cDNA | P3/Sabin RNA | Amino Acid Change |
|---|---|---|---|
| 198 | G | A | 5' untranslated |
| 4466 | T | C | His to Tyr (2C) |
| 6334 | T | C | silent |

The nucleotide error at position 198 in the cDNA is situated in the 5' untranslated region of the genome. The function of that region remains unknown. The presence of a T, not a C, in the cDNA at position 4466 would create a change in residue 118 of the 2C protein from histidine to tyrosine. Although the function of the 2C protein remains undefined, the predicted amino acid change appears to be significant. The nucleotide change at position 6334 is in the polymerase gene, but is silent with respect to amino acid change.

In order to obtain a full-length cDNA clone which corresponds exactly to the poliovirus RNA sequence, the protocol depicted in FIG. 4, panels A and B is followed. Specifically, the P3/Sabin cDNA insert pLL3-II is subcloned into the PstI site of bacteriophage M13 for oligonucleotide-directed mutagenesis of nucleotide 198 from G to A as described below. An oligonucleotide spanning nucleotides 190–206 and containing an A at position 198 is synthesized for this purpose. The oligonucleotide has the sequence: 3'-GGCGTATCTGACAAGGG-5' (SEQ ID NO:4).

Mutagenesis is performed using a "T7-GEN In Vitro Mutagenesis Kit" (United States Biochemical, Cleveland, Ohio) and following the manufacturer's directions. The mutagenized insert is called pLL3-II(A). Following mutagenesis, pLL3-II(A) is sequenced to confirm the presence of an A at position 198. pLL3-II(A) is then removed from M13 with PstI and subsequently digested with SacI, which cuts at nucleotide 747. The fragment spanning nucleotides 1–747 is used to replace the corresponding fragment in pLL3-FL. The resulting full-length cDNA containing the mutagenized nucleotide at position 198 is referred to as pLL3-FL(A).

Next, pLL3-FL(A) is digested with PstI and the fragment spanning nucleotide 1 to 2604 is isolated. A portion of the isolated PstI fragment of pLL3-FL(A)—nucleotides 1 to 1922—is then subjected to polymerase chain reaction (PCR) using the following two oligonucleotides as primers:

1) 5'-CTGCAGTAATACGACTCACTATAGGT-TAAAACAGCTCTGGGGTTG-3' (SEQ ID NO:5); and 2) 5'-GAATCATGGTGTCTATCTC-3' (SEQ ID NO:6).

Oligonucleotide 1 represents, in a 5'-to-3' orientation, a PstI site, the T7 promoter and nucleotides 1–20 of the positive strand of P3/Sabin cDNA. Oligonucleotide 2 represents nucleotides 1904–1922 of the negative strand of P3/Sabin cDNA. PCR is performed using the GeneAMp kit from Perkin-Elmer Cetus.

The double-stranded DNA produced by PCR is then cleaved with EcoRI, which cuts at nucleotide 784 of P3/Sabin cDNA. The resulting 0.8 kb fragment representing the T7 promoter and the 5' end of P3/Sabin cDNA is isolated and subcloned into the SspI/EcoRI-cut pBR322. The resulting plasmid, termed pVR309, is confirmed to contain the T7 promoter and nucleotides 1–784 of P3/Sabin cDNA.

Next, pLL3-FL is cut with EcoRI, which cuts at nucleotides 784 and 2867. The fragment spanning these nucleotides is isolated and ligated to EcoRI cut PVR309. The resulting plasmid, pVR312, contains the first 2867 nucleotides of P3/Sabin cDNA.

In order to change the nucleotides at 4466 and 6334 to correspond to the viral RNA sequence, oligonucleotide-directed mutagenesis is performed as described above. The insert pLL3-253 is subcloned into the PstI site of M13. Oligonucleotide 3'-CTCGTTTGTGGCATAAC-5' (SEQ ID NO:7) is used to change nucleotide 4466 from a T to a C. Oligonucleotide 3'-CCCATGGGGATGCACCG- 5' (SEQ ID NO:8) is used to change nucleotide 6334 from a T to a C. The mutagenized nucleotides are confirmed by nucleotide sequencing. The resulting corrected cDNA fragment termed pLL3-253(C).

Next, pLL3-253(C) and pLL3-271 are assembled into a single clone by cleaving each with HindIII and subsequently ligating the resulting large fragments together. The resulting DNA, referred to as pLL3-I(C), represents nucleotides 1500 through the 3-poly(A) end of P3/Sabin. The complete cDNA insert of pLL3-I(C) is then isolated by partial PstI digestion. A partial digest is necessitated because of the presence of a PstI site at nucleotide 2604. pLL3-I(C) is then ligated to PstI cut pBR322. A portion of that insert is then removed from pBR322 by a SmaI/NruI digest. The excised piece spans nucleotide 2766 through the 3'-end of the cDNA and into pBR322. A SmaI/NruI fragment is also excised from pVR312. This DNA represents sequences from the NruI site in pBR322 through the T7 promoter and the 5'-end of P3/Sabin cDNA and up to the SmaI site at nucleotide 2766. These two SmaI/NruI fragments are then ligated together to form a true P3/Sabin cDNA. The resulting plasmid is called pVR318. The presence of a full-length insert in pVR318 is confirmed by restriction enzyme analysis. However, upon sequencing of pVR318 it was determined that position 2493 was found to have a T, rather than a C.

In order to convert nucleotide 2493 to a C, a SacI/HindIII restriction fragment spanning nucleotides 1895 through 4241 from PVR318 is removed and replaced with a corresponding fragment from subclone pLL3-271. This scheme is depicted in FIG. 5. Specifically, pLL3-271 is digested with SacI and Hind III and the 2.346 kb fragment spanning nucleotides 1895 through 4241 is isolated by agarose gel electrophoresis. Plasmid PVR318 is partially digested with SacI and HindIII to remove the 2.346 kb fragment between nucleotides 1895 and 4241. The remaining 10.007 kb fragment is isolated by agarose gel electrophoresis and then ligated to the SacI/HindIII fragment from pLL3-271. The resulting ligation product, pLED3, represents a true full-length type 3 poliovirus vaccine strain cDNA. The sequence of pLED3 is depicted in FIGS. 6A–6K.

EXAMPLE 8

Transfection of Cells With Poliovirus P3/Sabin cDNA

Primary monkey kidney cells are grown to 80% confluency in duplicate 25 cm² flasks in Eagle's basal medium (BME) containing Hank's balanced salt solution, 0.35% bicarbonate and 10% calf serum. The cultures are maintained at 37° C. The medium is then removed and the cells transfected with pLED3 (prepared as in Example 7), added as a calcium phosphate precipitate in HEPES-buffered saline. After 20 minutes at room temperature, the cells are covered with Earle's lacteal maintenance medium and incubated for 4 hours at 37° C. The medium is then removed and the cells are washed once with fresh, warm medium. Two milliliters of 15% glycerol in HEPES-buffered saline are then added to the cells and incubation is continued for 3.5 minutes at 37° C. The glycerol is then removed and the cells are washed once again with fresh medium. One of the duplicate cultures is then covered with warm medium containing 1% Noble agar (Difco, Detroit, Mich.), while the other is covered with agar-free medium. The cultures are incubated at 34° C. for 1–5 days. Plaques are visualized by staining cells with 0.01% neutral red. Medium from the liquid culture is assayed for infectious poliovirus by plaque titration on Vero cells.

EXAMPLE 9

In Vitro Transcription of P3/Sabin cDNA

In vitro transcription is performed by the method of van der Werf et al., *Proc. Natl. Acad. Sci. USA*, 83, pp. 2330–34 (1986). pLED3, containing the T7 promoter-P3/Sabin construct, is linearized at an appropriate restriction site outside of the poliovirus sequences and purified by phenol extraction and ethanol precipitation. This template DNA is then added to a mixture containing 20 mM sodium phosphate, pH 7.7, 8 mM $MgCl_2$, 10 mM DTT, 1 mM spermidine-HCl, 50 mM NaCl and 1 mM each of dATP, dCTP, dGTP and dUTP. RNA synthesis is initiated by the addition of 10–15 units of T7 RNA polymerase/µg linearized template and allowed to continue for 30 minutes at 37° C.

Following RNA synthesis, the DNA template is digested away with Dnase I. The remaining RNA is purified by phenol extraction and ethanol precipitation in the presence of 2.5 M ammonium acetate. The purified RNA is quantified by UV spectrophotometry.

EXAMPLE 10

Transfection Of Cells With In Vitro Transcribed P31/Sabin RNA

Semi-confluent monolayers of primary monkey kidney cell are prepared as described in Example 8. The cells are transfected with the RNA prepared in Example 9 using the method of A. Vaheri et al., "Infectious Poliovirus RNA: A Sensitive Method of Assay", *Virology*, 27, pp. 434–36 (1965). Specifically, the cell monolayers are washed with isotonic phosphate-buffered saline (PBS). After 15 minutes, the PBS is completely removed by aspiration. The monolayer is then coated with 0.25 ml of inoculum containing RNA and 500 µg/ml DEAE-dextran (Sigma, St. Louis, Mo.; 500,000 MW) in PBS. The infected monolayers are kept undisturbed at room temperature for 15 minutes, washed once with Earle's lacteal maintenance medium and then overlaid with either fresh medium or medium containing 1% agar, as described in Example 8. After 4–5 days at 34° C., virus is detected by plaque formation (in cultures containing agar) or by cytopathic effect.

Virus is then isolated and purified. Viral RNA is isolated by the techniques described previously. The isolated RNA is sequenced and the nucleotide at position 2493 is confirmed as cytosine, the same as the original source virus.

EXAMPLE 11

Evaluation Of The Effect Of Nucleotide 2493 On The Attenuation Of A Strain 3 Poliovirus A derivative of an attenuated strain 3 poliovirus cDNA which contains a T instead of a C at nucleotide 2493 is constructed, such as pVR318. Viruses are produced from cDNAs with either T or C at 2493 as in Examples 8 and 10. The resulting viruses are then tested for neurovirulence in monkeys according to standard protocols.

EXAMPLE 12

Increasing The Attenuation Of A Strain 3 Poliovirus

A strain 3 poliovirus cDNA which contains a T at position 2493 is subjected to site-directed mutagenesis to convert the T to a C, For example, pLED3 is digested with PstI to remove the poliovirus coding sequence. The poliovirus cDNA contains a single, internal PstI site at nucleotide 2604. Therefore, a PstI digestion yields a 5', 2.6 kilobase viral cDNA fragment and a 3', 4.8 kb viral cDNA fragment The 2.6 kb fragment is isolated by standard techniques and subcloned into the unique PstI site of vector M13mp18. Nucleotide 2493 is then converted from a T to a C by site-directed mutagenesis using a "T7-GEN In Vitro Mutagenesis Kit" (United States Biochemical, Cleveland, Ohio) and following the manufacturer's directions. Following mutagenesis, the 2.6 kb piece of cDNA is removed from the vector, relegated to the 3' piece of viral cDNA and the intact cDNA is cloned into pBR322. Both the mutagenized cDNA and the original cDNA are used to produce viable poliovirus as in Example 8. The resulting viruses are assayed for attenuation according to standard protocols. The mutagenized virus produced by the cDNA containing a C at nucleotide 2493 is expected to be more attenuated than the original virus.

Confirmatory sequencing of the entire cDNA sequence in plasmid pLED3 revealed an additional A (adenosine) in a region where a run of six A's is normally found in the viral genome (positions 4133–4138). The following steps describe a method to derive pLED3.2 from pLED3:

Isolation and mutagenesis of erroneous pLED3 sequence

Starting with purified pLED3 plasmid DNA, digest the DNA to completion with restriction enzymes SacI and HindIII. By a method of choice (i.e., gel electrophoresis, HPLC) purify the 2,346 base pair SacI/HindIII fragment representing cDNA nucleotides 1895–4241.

Subclone the purified restriction fragment into bacteriophage M13 to enable oligo-directed deletion mutagenesis. An DNA oligonucleotide spanning nucleotides 4121–4150 is synthesized for this purpose. The sequence of this oligomer is: 5'-CGCCTCAGTAAATTTTTTCAACCAACTATC-3' (SEQ ID NO:9).

Mutagenesis is performed using a "T7-GEN In Vitro Mutagenesis Kit" (United States Biochemical, Cleveland, Ohio) and following the manufacture's directions. The mutagenized insert is confirmed to possess 6 instead of 7 A's at positions 4133–4138 by sequence analysis. As above, the altered SacI/HindIII fragment is gel purified in preparation for ligation into the plasmid body lacking this restriction fragment.

Preparation of pLED3.2 from pLED3 Plasmid

Starting with purified pLED3 plasmid DNA, partially digest the DNA with restriction enzymes SacI and HindIII. Purify the 10,007 base pair SacI/HindIII fragment corresponding the plasmid minus the 2,346 base pair SacI/HindIII fragment discussed above.

Construction of pLED3.2

The purified plasmid body and mutagenized 2,346 base pair fragment are ligated together. Competent E. coli DH5α cells are transformed with the ligation products and tetracycline resistant colonies are selected. Identity of pLED3.2 is based on the confirmation of 6 A's at 4133–4138.

LED3 and VR318 viruses used in monkey NV test

The full-length cDNA in pLED3 (uncorrected) was infectious even though the additional A discussed above predicts a shift in the reading frame for viral proteins 2C, 3A, 3B, 3C and 3D. In vitro transcription of pLED3 cDNA using T7 RNA polymerase produced RNAs which possessed the erroneous seven A's as determined by direct sequence analysis. When these transcripts were used to transfect monkey kidney cells, virus was recovered which possessed the correct number of A's at this site.

Although the cDNAs in pLED3 and pVR318 differ by nucleotide composition at 2493 and by the number of A's between 4130–4136, the 2493 mutation was the only difference found to distinguish the viruses generated using these cDNAs. These cDNA-derived viruses were used to carry out the studies to assess the significance of 2493 mutation (described in the manuscript currently under review).

Polymerases are known to have problems copying from regions in which a single nucleotide is repeated several times. We proposed that T7 RNA polymerase may have generated by error some RNAs which contained six instead of seven A's while transcribing the run of seven A's from pLED3. Only those transcripts possessing six A's could produce virus upon transfection of cells. This proposed explanation seemed highly probable to a scientist who works on T-phage polymerase.

Recombinant DNA prepared by the processes of this invention is exemplified by a sample deposited with the American Type Culture Collection located at 12301 Parklawn Drive, Rockville Md. 20852 under the provisions of the Budapest Treaty on the International Recognition of the Deposit of Microorganisms for the Purposes of Patent Procedures. This sample was deposited on Apr. 17, 1990, identified as a plasmid containing the infectious full length copy of vaccine strain Sabin 3, and designated pLED3. This deposit was assigned ATCC accession number 40789.

EXAMPLE 13

Experimental Methods

Sabin 3-Specific Mutation Within the N-Terminal Region of VP1 is Attenuating

Preparation of cDNA clones

Viral RNA was extracted from Sabin 3 vaccine virus (Lederle-Praxis Biologicals, N.Y.) after pelleting and SDS disruption as described before (20). A cDNA library was made from the viral RNA template using reverse transcriptase and a procedure described elsewhere (12). Oligonucleotide-directed mutagenesis was performed on DNAs subcloned in M13 grown in E. coli CJ236, to change the cDNA sequence at single base positions (16). For this purpose, antisense oligonucleotides (17-mers) were synthesized with the target nucleotide positioned in the center of the sequence. Common restriction enzyme cleavage sites EcoRI, HindIII, SacI, SmaI) were used to construct full-length cDNA clones. The full-length cDNAs (7,459 bp) were constructed in vector pBR322, selected and amplified using E. coli DH5α (Bethesda Research Laboratories).

Cells

Vero cells were propagated as monolayers in Eagle's MEM with Earle's salts supplemented with 0.11% bicarbonate and 10% fetal bovine serum. Primary African green monkey kidney cells (PCMK) were initiated in BME with Hank's salts containing 0.035% bicarbonate and 10% serum. At 70% confluence, the cells were refed with BME (Earle's salts) containing 5% serum. During poliovirus infection, all cultures were maintained in modified Earle's lactalbumin hydrolyzate maintenance medium (LMM; pH 7.34 without serum.

viruses

The Sabin 3 vaccine virus (RSO+2; Lederle-Praxis Biologicals, Pearl River, N.Y.) was prepared by a single passage of the rederived (RSO+1) manufacturing seed in PCMK cells. For experimental purposes, the same seed was used to produce RSO+2 vaccine virus in Vero cells. Virus NC1 represents vaccine (SO+2) produced in PCMK cells from the original (SO+1) manufacturing seed. The cDNA-derived viruses recovered from Vero cells transfected with T7 RNA polymerase transcripts of pLED3 or pVR318 were designated LED3+1 and VR318+1. These "seed" viruses were amplified once more in Vero cells at a multiplicity of infection (MOI) of 0.1 at 33.5°±0.5° to create virus stocks LED3+2 and VR318+2. Particular attention was paid to preparing the LED3+2 and VR318+2 virus samples in a manner as similar as possible to actual vaccine (ie. passage level and culture conditions). The characterization studies were carried out using these final virus stocks.

Determination of Virus Titer

The titer of infectious virus in samples was determined most often by microtitration on HEp-2 cells and expressed as tissue culture infectious dose $(TCID)_{50}$ per ml (1). In some cases, infectious titer was measured by plaque titration on Vero cell monolayers and therefore expressed as plaque-forming units (pfu) per ml. Serial ten-fold dilutions of virus prepared in LMM were used to inoculate 25 cm² confluent monolayers and allowed to absorb at 22° C. The cells were overlaid with 1.0% Noble agar (Difco Laboratories) in MEM (Hank's) plus 2% fetal calf serum then incubated at 33.5°±0.5° C. After 3 days, plaques were visualized and counted after staining the cells with neutral red (0.01% solution). For a given sample, there is routinely a 0.6 log difference in absolute numbers determined using the two methods described above; the $TCID_{50}$ value is always greater.

Nucleotide Sequence Determination

RNA sequence was determined using synthetic oligonucleotides and the dideoxynucleotide chain termination method as described before (20). Sequencing of cloned cDNAs was performed using Sequenase DNA Sequencing Kit (U.S. Biochemical).

In vitro RNA Synthesis and Transfection

DNA templates were prepared by digesting the plasmid DNA completely with PvuI restriction enzyme followed by extraction with phenol and ethanol precipitation, Transcription reaction mixtures containing 1 μg of DNA template were prepared as described by Moss et al. (12). RNA synthesis was initiated by addition of 30 units purified T7 RNA polymerase (Pharmacia) and the reactions were incubated at 37° C. for 90 mins. The DNA template and full-length transcription product were quantitated by comparing the intensity of appropriately-sized bands to known amounts of a standard after electrophoresis in agarose gels stained with ethidium bromide. The 9.0 kb HindIII fragment of bacteriophage lambda DNA was used as the standard for template; a 7.5 kb single-stranded RNA marker (Bethesda Research Laboratories) was used for transcript. Numerical values were obtained by performing densitometry on a photographic negative taken of the gel. Aliquots of the transcription reaction mixture containing 25 μg of full-length transcript were used to transfect Vero cell monolayers (25 cm2) according to the procedure described by van der Werf et al, (23), The cDNA-derived viruses were harvested when the cell monolayer was completely destroyed (+4 CPE).

Isotopic Labeling of Virus and PAGE

Vero cells ($6.5 \times 10^6$) were infected at an MOI of 16 pfu/cell. The virus was allowed to absorb for 1 hour, the cells were then washed twice and covered with LMM before incubation at 33.5° C. Four and a half hours later, the medium was changed to methionine-free MEM (Select Amine Kit, GIBCO). After one hour, the cells were replenished with fresh medium supplemented with [$^{35}$S]methionine (specific activity, >1000 Ci/mmol; Amersham) to a final concentration of 60 μCi/ml and incubation continued. At +4 CPE (within 24 hr), the medium containing virus was clarified, first by low-speed centrifugation (2500 rpm, 20 mins, 4° C.) and then by microfiltration (0.22 μm Millex-GV; Millipore). Virus was pelleted by ultracentrifugation using a Beckman 70.1Ti rotor (70K, 1 h, 4° C.), and then resuspended and boiled in Laemmli sample buffer (10). The samples were subjected to SDS-polyacrylamide gel electrophoresis and the proteins visualized by autoradiography.

Virus Thermostabiltiy Curves

Multiple 3.0 ml samples of virus (approx. $10^{7.3}$ pfu/ml in LMM) were incubated at room temperature (22° C.) or in water baths at 37° C. or 42° C. At 24 hour intervals over the course of 5 days, one sample from each incubation set was removed and frozen at −20° C. Once all the sample incubations were completed, the virus titer in each sample was measured by plaque titration on Vero monolayers.

Virus Growth Curves

Vero cell monolayers ($10^7$ cells/25cm$^2$ flask) were infected with 4 pfu/cell and maintained as described above. At the indicated times post-infection, the medium from individual cultures was harvested then stored at 70° C.

Neurovirulence Test

Virus samples were tested for neurovirulence in *Macca mulatto* monkeys using two accepted procedures. As described in the United States Code of Federal Regulations (22), 0.2 ml or 0.5 ml of virus sample containing at least $10^{7.6}$ TCID$_{50}$/ml is injected into the spinal cord (IS) or the thalamic region of each brain hemisphere (IT) of a monkey, for each test respectively. The WHO test (26) involves intraspinal injection of monkeys with 0.1 ml of virus (titer of $10^{6.5}$–$10^{7.5}$ TCID$_{50}$/ml). After injection, the test animals are observed for 17–21 days for clinical signs of poliomyelitis. The animals are then sacrificed to allow histological examination of the brain and spinal cord for poliovirus lesions. The nervous tissue from each monkey is evaluated using a scoring method from 1 (low) to 4 (high) to reflect the severity of neuronal damage observed. The mean lesion score is an average of the scores recorded for monkeys within a group.

Statistical Analysis

Differences in mean lesion scores were analyzed by Analysis of Variance (ANOVA) model with Least Squares determinations employed for mean range testing. Frequencies of reactivity in the monkeys injected intrathalamically were tested for significance using Chi-square test.

Results

Construction of an authentic LED3 cDNA

Screening of the cDNA library through restriction analysis and nucleotide sequencing, identified four cDNA clones which represented all but the 5' six nucleotides of the Sabin 3 genome. The 5'-most cDNA clone was modified so that first six nucleotides of Sabin 3 cDNA were reconstructed and positioned under the control of bacteriophage T7 promoter by incorporation of a synthetic DNA oligonucleotide [5'-CTGCAGTAATACGACTCACTATAGGT-TAAAACAGCTCGGGTTTG- 3'] using the polymerase chain reaction. The orientation of the promoter ensures the synthesis of positive-sense RNA transcripts of the cloned cDNA. When the complete nucleotide sequence of the four cDNA subclones was compared to the LED3 RNA sequence (24) four nucleotide differences were identified. It is unclear whether the nucleotide differences represent errors made during reverse transcription or sequence divergence of a minor population within the vaccine virus sample. However, the full-length uncorrected cDNA was not infectious since virus nor CPE resulted from transfection of cells with T7-derived transcripts made of the cDNA. The sequence was corrected using oligonucleotide-directed mutagenesis (see Materials and Methods, Example 13) at three of these positions: 198 (G to A), 4466 (T to C) and 6334 (T to C). The last error, U instead of C at position 2493, fortuitously represented the Leon-like nucleotide at this position and was left untouched in the full-length cDNA in pVR318. This clone differs from LED3 RNA sequence only at n2493. The final step in the production of an authentic LED3 cDNA (pLED3.2) was accomplished by cDNA fragment exchange (SacI at n1895 to HindIII at n4241) between pVR318 and a vaccine cDNA subclone found to possess C at position 2493.

The full-length LED3 cDNA construct in cloning vector pBR322 is diagrammed in FIG. 7A. Nucleotide sequence analysis across the junction between the 3' terminus of the Sabin 3 cDNA and plasmid pBR322 indicated a poly-A tail consisting of 27 A's. A string of 15 C's derived from cDNA cloning steps immediately follows the poly-A tail.

In vitro transcription of the cDNAs in pLED3 and pVR318

The plasmid DNAs were digested with PvuI to 1) generate a linear DNA template containing the entire poliovirus cDNA for transcription by T7 RNA polymerase and to 2) create a template with the shortest span of extraneous vector sequence after the 3' end of the cDNA. PvuI corresponds to the first restriction site after the 3' end of the cDNA (exactly 126 bp) which is not present within the cDNA. Two PvuI fragments (4.4 kb and 8.1 kb) are produced from pLED3 and pVR318, but only the 8.1 kb fragment contains the T7 promoter based on sequence analysis. (refer to FIG. 7, A).

FIG. 7B demonstrates that RNAs are efficiently synthesized by T7 RNA polymerase from the PvuI-restricted pLED3 and pVR318 and their size matches that predicted for runoff transcripts from the 8.1 kb fragment. In lanes 5 and 6, the two upper bands (low intensity) correspond to the 8.1 kb and 4.4 fragments produced by digestion of the plasmid DNAs with PvuI. Lane 4 contains HindIII/lambda DNA for a ds DNA size reference, The transcription product (most intense band in lanes 5 & 6) comigrates neatly with the 7.5 kb ssRNA marker (lanes 1–3) which is consistent for full-length (7585 nucleotides) RNAs. In comparison to virion RNA (lane 7), the in vitro transcripts of the poliovirus cDNA migrate slightly faster, perhaps due to the absence of covalently attached VPg protein. A transcription reaction containing 1 µl of template reproducibly produced 20–25 µg of full-length transcript. As shown here, the band corresponding to in 1 µg of a 50 µl reaction mixture (lane 5 or 6) is approximately the same intensity as the band representing 500 ng of 7.5 kb ssRNA (lane 2). Direct sequence analysis of these transcripts determined that there are two extra guanines at the 5' end immediately before the first poliovirus nucleotide and confirmed the presence of 126bp of extraneous pBR322 sequence at the 3'end after the poly-A, poly-C tail.

When Vero cells were transfected with the RNAs described above, cytopathic effects consistent with poliovirus infection were observed in 24 hours and virus were harvested (+4 CPE) within 48–72 hours. The specific infectivity of the transcripts was found to be $1-2\times10^2$ pfu/µg, about 3% that of vaccine RNA. As determined by sequencing, the RNA from the recovered viruses lacks the extraneous pBR322 sequence at the 3' end. In addition, the genomes of these viruses were verified to possess the attenuated nucleotides at positions 472(U), 2034(U), and 6061(U); nucleotide 2493 was the only known difference between LED3 (2493-C) and VR318 (2493-U).

Mutation at n2493 correlates with altered VP1 mobility

The mutation identified at position 2493 in the consensus genome of Sabin 3 vaccine virus predicts a Ile-6→Thr substitution in VP1 (24). To determine if the biochemical properties of VP1 would be altered by this amino acid substitution, the UPI proteins of LED3 altered by this amino acid substitution, the VP1 proteins of LED3 and VR318 were compared. The VP1 from LED3 contains threonine at residue 6, whereas VR318 has isoleucine at this site. The difference in molecular weights between these amino acids is minimal and yet the VP1 proteins from these viruses are distinguishable by SDS-PAGE (FIG. 8). A possible explanation for this observed difference in VP1 migration derives from the fact that the Thr side chain has a hydroxyl group that can form a hydrogen bond, whereas the Ile side chain is hydrophobic. As a result, the VP1 of VR318 virus with Ile-6 may bind more SDS and therefore migrate faster than the VP1 of LED3. These data associate at least one biophysical change with the 2493 mutation. Whether this alteration in VP1 impacts the 3D structure of the virion is under evaluation.

Thermostability of LED3 and VR318 viruses

In the three-dimensional structure of poliovirus, the N-terminal region of VP1 is buried on the inside of native virions in close association with terminal regions of the other capsid proteins (6). In attempt to assess whether the 2493 mutation alters virion stability, LED3 and VR318 viruses were compared for susceptibility to thermal inactivation at several temperatures. As illustrated in FIGS. 9A–9C there was no loss in titer observed for either virus sample over a five day period at room temperature (22° C.). At 37° and 42° C., the titers of both virus samples decreased similarly. Despite heat treatment, the difference in plaque morphology between LED3 and VR318 viruses were preserved (see below).

Effect of n2493 on phenotypic markers

Small plaque size is often used to differentiate attenuated vaccine strains from virulent strains (13). In conducting a simple plaque titration of the cDNA-derived virus samples on Vero cells monolayers, it became apparent that the VR318 virus produces plaques that are obviously larger than those of LED3 virus. When the comparison included the pathogenic parent Leon strain, it was clear that VR318 plaques are of intermediate size (see FIG. 10). These data suggest that the single nucleotide difference at position 2493 between LED3 (C) and VR318 (U) is responsible for the increase in plaque size displayed by VR318 compared to LED3.

The traditional temperature-sensitivity (rct/40° C.) and "d" marker phenotypes of LED3 and VR318 viruses were also evaluated. Although these viruses were not distinguishable by either of these tests, both exhibited the attenuated phenotype compared to Leon virus (data not shown).

Growth curves of LED3 and VR318

To compare LED3 and VR318 replication, the growth kinetics of these viruses were compared in Vero cells under conditions known to be permissive for attenuated poliovirus (i.e, low temperature, high pH). FIG. 11 demonstrates there is no dramatic difference between the kinetics of virus release from Vero cells infected with LED3 and VR318. The titers achieved at 24 hours post-infection ($10^8$ pfu/ml) indicated that neither of these viruses is severely debilitated under these conditions. A consistent, although subtle, difference was observed in the fold increase in titer between 8 and 12 hours post-infection suggesting that VR318 may have the ability to replicate faster than LED3. During this time period, the titer of VR318 increased 200-fold compared to only a 30-fold increase for LED3. Whether modification of culture conditions (i.e., lower pH) exaggerates the observed difference between LED3 and VR318 growth kinetics is under evaluation.

Neurovirulence of LED3 and VR318 in monkeys

Through the construction and neurovirulence testing of recombinant viruses derived from full-length Sabin 3 and Leon cDNAs, Westrop eta. (25) have correlated the attenuated phenotype of Sabin 3 with the point mutations at positions 472 and 2034. Applicants' identification of the Sabin 3-specific point mutation at 2493 (24), raised the question of whether this mutation might also be a determinant of attenuation.

The cDNA-derived viruses, LED3 and VR318, were compared to appropriate controls for neurovirulence as tested in monkeys by procedures contained in either the WHO or United States CFR requirements for the acceptance of vaccine lots (see Materials and Methods, Example 13). Differences between these procedures include the route of inoculation (intrathalamic & intraspinal versus only intraspinal) as well as amount (volume and titer) of the sample injected.

Table 1A lists the neurovirulence data from the CFR intraspinal (IS) test in which LED3 and VR318 were tested concurrently and compared to test results of actual vaccine (RSO+2) produced on primary monkey kidney cells (PCMK). Testing of RSO+2 (Vero) vaccine demonstrated that the use of Vero cells to produce vaccine virus as described had no effect on attenuation. The mean lesion scores produced by RSO+2 (PCMK), RSO+2 (Vero) and LED3+2 (Vero) were 0.52, 0.36 and 0.34, respectively. These data demonstrate that LED3 is no more neurovirulent than current vaccine virus. Interestingly, the mean lesion score of monkeys receiving VR318 was 1.31 which was significantly higher (p<0.01) than the scores produced by the other viruses. These data indicate that VR318 virus is not equivalent to current RSO+2 vaccine and that presence of C (LEd3 and RSO+2) instead of U (VR318) at nucleotide position 2493 is attenuating.

As above, the neurovirulence of LED3 and VR318 after intrathalamic route of injection into monkeys was compared to data obtained from four complete tests of current RSO+2 vaccine (Table 1B). Since brain tissue is less susceptible than spinal tissue to poliovirus infection, neurovirulence using this procedure is based essentially on whether any lesions are visible and in what percentage of the monkeys rather than a lesion score. As demonstrated by actual RSO+2 vaccine, a low level of reactivity in a group of monkeys (4.0%) is typical and desirable. Of the 10 monkeys receiving LED3, none exhibited lesions. VR318, however, produced lesions in 2 of 10 (20%) test animals. Although a group of 30 monkeys are required for a complete IT test, the increased percentage of positive monkeys in the VR318 group is highly unusual and predicts that VR318 would fail CFR IT data indicate that when compared to current RSO+2 vaccine, LED3 virus is equivalent and VR318 is more neurovirulent.

Using the WHO test procedure, LED3 and VR318 were evaluated concurrently with virus NC1, which is equivalent to the attenuated type 3 WHO test reference. As listed in Table 2, the mean lesion scores for LED3 and VR318 were 0.21 and 1.51, respectively. Confirmed by three different methods, the demonstration that LED3 is more attenuated than VR318 is unequivocal. The interpretation of the WHO test data is made somewhat difficult however by the performance of the attenuated reference, NC1. In this test, NC1 produced a mean lesion score of 1.08, which falls between the values calculated for LED3 and VR318. Although a mean score of 1.08 is high for this test reference, the comparison of reactivity between NC1, LED3 and VR318 is valid since they were tested concurrently. A statistical comparison of the resultant scores points to the fact that by this test procedure, VR318 cannot be distinguished from the attenuated reference. Based on this preliminary data, it is unclear whether VR318 would fail in a full WHO test involving 24 monkeys per group. On the other hand, the lesion score associated with LED3 was shown to be significantly lower than either VR318 or the NC1 reference (p<0.01).

Interestingly, the NC1 reference virus represents vaccine material manufactured using Sabin original (SO), not the rederived Sabin original (RSO) seed. Nucleotide sequence determination at position 2493 of SO+2 vaccine (Lederle; same as NC1) revealed a 1:1 mixture of C and the variant U. Similar evaluation of current RSO+2 vaccine (Lederle) demonstrated only C at this position supporting the fact that the RSO seed is a purified derivative of the SO strain (24). Since test samples LED3, VR318 and NC1 did not differ in nucleotide composition at position 472 based on RNA sequence determination, the increased level of neurovirulence exhibited by NC1 compared to LED3 using the WHO procedure likely derives from the subpopulation of 2493-U variants in the NC1 pool of virus.

The identification of a new Sabin 3-specific mutation at position 2493 which encodes an isoleucine to threonine change at the sixth amino acid of VP1 (24) is shown here to be a determinant of attenuation. The attenuation of Sabin 3 poliovirus has been correlated to point mutations at positions 472 and 2034 by others previously (25). To assess the contribution of the 2493 mutation, a virus was produced using a completely verified vaccine cDNA (LED3) and compared to a derivative, VR318, which was the same except that it possessed the Leon-like nucleotide (U) instead of C at this position. The additional mutation in LED3 correlated to smaller plaque size as well as decreased neurovirulence in monkeys.

The data presented herein demonstrate that the biological properties associated with attenuation of the Sabin 3 vaccine strain were preserved in LED3. There are many benefits associated with the use of a Sabin 3 cDNA-derived seed strain. The stock volumes of both the original and rederived Sabin seeds, SO and RSO respectively, are limited due to the fact that they are virus plaque isolates. When seeds are stored in the form of a cloned, genetically defined cDNA, the limitations on seed supply are removed; in addition, such seeds can be preserved indefinitely. Without restriction on seed supply there is increased flexibility in the multiplicity of infection (MOI) that can be used to produce vaccine. Weeks-Levy et al. (24) showed that virus samples produced using accepted manufacturing seeds at higher MOI's are genetically more homogeneous. Since RNA viruses by their nature generate variants at height frequency than DNA viruses, an RNA virus seed established in the form of a cloned, genetically defined DNA should be the most homogeneous. By this approach, the amount of undesirable variants that could be selectively amplified during passage have been minimized which translates to increased genetic stability. Passage studies to assess whether LED3 constitutes a more genetically stable see as compared to other manufacturing seeds for Sabin 3 vaccine is currently under evaluation.

Based on nucleotide sequence determination, Sabin 3 variants possessing U at 2493 during passage in vitro were shown to accumulate more rapidly than variants possessing C at 472 (24). In the same study, the Sabin 3 component of different OPVs was found to vary greatly in the proportion of C and U at 2493. Although the data presented here do not address how the proportion of 2493-U variant affects the acceptability of vaccine lots, data comparing viruses LED3 (2493-C) and VR318 (2493-U) suggest that the result will depend on neurovirulence test method used for the evaluation. Of particular interest was the ability of the CFR intrathalamic test method to distinguish LED3 and VR318. The unusually high reactivity of VR318 in the brain compared to LED3 or RSO+2 vaccine suggests that the interaction between virus and brain tissue is enhanced when virus possesses U at 2493. Since the WhO test method does not evaluate vaccine by intrathalamic route of injection, our data suggest that this test would be less likely to detect 2493-U virus subpopulation in vaccine lots.

A detection method incorporating the polymerase chain reaction was used recently by Chumakov et al. (2) to determine that vaccine lots containing 472-C variants comprising greater than 1.17% of total virus failed the WHO neurovirulence test. The determination of equivalence at position 472 for LED3 and VR318 was based on sequence analysis of the viral RNA. It was determined that a 10% variant subpopulation is the limit of detection using this method (20). It is possible that the more sensitive PCR method would detect 472-C subpopulation in both LED3 and VR318 virus preparations. It is however unlikely that these virus samples would differ in proportion of 472-C variant because LED3 and VR318 are equivalent passage levels from the cloned cDNA and were generated under identical conditions. A preliminary evaluation of LED3 and VR318 using a PCR method to detect 472-C variants shows that these samples cannot be distinguished.

There are several lines of data supporting the selective advantage for Sabin 3 variants possessing U at 2493 in vivo, as well as in vitro. Stool isolate KW4, recovered 5 days post-vaccination, was shown previously to differ from the administered vaccine strain at three positions: 472=C, 2493=U, and 6061=U/C (20). Based on the data presented here, the intermediate level of neurovirulence observed for KW4 in that study can now be attributed to the mutation at 2493 as well as 472. Weeks-Levy et al. (24) found that two of three virus isolates recovered from nervous tissue (brain or spinal cord) of monkeys that had been injected intraspinally with NC1, the attenuated reference virus, possessed U at 2493. That isolate NC1-679B had U at 2493 without loss of the attenuated U at 472 may specifically relate to how this virus spread and replicated in the brain. The data are consistent with observations of increased neurovirulence for VR318 compared to LED3 as tested by CFR intrathalamic method.

The mechanism by which the change from U to C at 2493 attenuates LED3 compared VR318 is unclear. This mutation alters the sixth amino acid capsid protein VP1. In the three-dimensional structure of poliovirus, Hogle et al. (6) show that this region of VP1 is buried on the inside of the native virion. More recently, Fricks and Hogle (5) demonstrated that upon attachment to susceptible cells, the virion undergoes conformational changes resulting in release of capsid protein VP4 and externalization of the amino terminus of VP1. These authors demonstrated further that exposure of the amino terminus of VP1 was required for attachment to liposomes and proposed that these events play a role in the mechanism of cell entry. Consistent with these observations, Kirkegaard (8) described two poliovirus mutants with different small deletions in the amino terminal region of VP1 which flank either side of residue six as defective in the physical release of viral RNA from the capsid during normal infection. Both of these deletion mutants exhibited small plaque phenotype. From these data, it is easy to speculate that the mutation is Sabin 3 at position 2493 also affects viral uncoating.

In addition to the mutation in VP3 (2034) of Sabin 3, attenuation determinants have been mapped to the capsid proteins in Sabin 1 (14) and a type 2 strain (P2/712) which is closely related to Sabin 2 (16). Although these other mutations occur within capsid protein VP1, the structural mutation described in this study is the first one to be mapped to the amino terminal region of VP1.

While a number of embodiments of this invention have been described hereinabove, it is apparent that the basic constructions can be altered to provide other embodiments which utilize the processes, recombinant DNA molecules, cDNA molecules and transformed hosts of this invention. Therefore, it will be appreciated that the scope of this invention is to be defined by the claims appended hereto rather than by specific embodiments which have been presented hereinbefore by way of example.

TABLE 1

NEUROVIRULENCE OF LED3 AND VR318 STRAINS USING CFR NV TEST PROCEDURE

A) INTRASPINAL[a]

| GROUP | VIRUS | CELL SUB-STRATE | NUCLEOTIDE AT 472 | NUCLEOTIDE AT 2493 | NO. OF MONKEYS | MEAN LESION SCORE |
|---|---|---|---|---|---|---|
| 1 | RSO + 2 | PCMK | U | C | 24 | 0.52 |
| 2 | RSO + 2 | VERO | U | C | 12 | 0.36 |
| 3 | LED3 + 2 | VERO | U | C | 16 | 0.34 |
| 4 | VR318 + 2 | VERO | U | U | 16 | 1.31[b] |

B) INTRATHALAMIC[c]

| GROUP | VIRUS | CELL SUB-STRATE | NUCLEOTIDE AT 472 | NUCLEOTIDE AT 2493 | NO. OF MONKEYS | PERCENT POSITIVE |
|---|---|---|---|---|---|---|
| 5 | RSO + 2 | PCMK | U | C | 120 | 4 |
| 6 | LED3 + 2 | VERO | U | C | 10 | 0 |
| 7 | VR318 + 2 | VERO | U | U | 10 | 20[d] |

[a]0.2 ml of virus (titer $\geq$ 7.6 log $TCID_{50}$/ml) administered intraspinally.
[b]Group 4 > 1, 2, 3 ($p < 0.01$) by ANOVA and mean range testing.
[c]0.5 ml of virus (titer $\geq$ 7.6 log $TCID_{50}$/ml) administered intracerebrally into the thalamic region of each hemisphere.
[d]Group 7 > 5, 6 ($p < 0.05$) by Chi-square test.

TABLE 2

NEUROVIRULENCE OF LED3 AND VR318 STRAINS USING WHO NV TEST PROCEDURE[a]

| GROUP | VIRUS | CELL SUB-STRATE | NUCLEOTIDE AT 472 | NUCLEOTIDE AT 2493 | NO. OF MONKEYS | MEAN LESION SCORE |
|---|---|---|---|---|---|---|
| 1 | LED3 + 2 | VERO | U | C | 6 | 0.21[b] |
| 2 | NC1[c] | PCMK | U | U/C | 6 | 1.08 |
| 3 | VR318 + 2 | VERO | U | U | 6 | 1.51 |

[a]0.1 ml of virus (titer 6.5 to 7.5 log $TCID_{50}$/ml) administered intraspinally.
[b]Group 2 < 1, 3 ($p < 0.1$) by ANOVA and mean range testing.
[c]NC1 (SO + 2) is an attenuated type 3 reference for the WHO NV test.

REFERENCES

1. Albrecht, P., J. C. Enterline, E. J. Boone, and M. J. Klutch. 1983. Poliovirurs and polio anitbody assay in HEp-2 and Vero cell cultures. J. Biol. Stand. 11:91–97.

2. Chumakov, K. M., L. B. Powers, K. E. Noonan, I. B. Ronison and I. S. Levenbook. 1991. Correlation between amount of virus with altered nucleotide sequence and the monkey test for acceptability of oral poliovirus vaccine. Proc. Natl. Acad. Sci. USA 88:199–203.

3. Domingo, E. 1989. RNA virus evolution and the control of viral disease. Prog. Drug Res. 33;93–133.

4. Dunn, G., N. T. Begg, N. Cammack, and P. D. Minor. 1990. Virus exretion and mutation by infants following primary vaccination with live oral poliovaccine from two sources. J. Med. Virol. 32:92–95.

5. Fricks, C. E. and J. M. Hogle. 1990 Cell-induced conformational change in poliovirus: Externalization of the amino terminus of VP1 is responsible for liposome binding. J. Virol. 64:1934–1945.

6. Hogle, J. M., M. Chow, and D. J. Filman. 1985. Three-dimensional structure of poliovirus at 2.9A resolution. Science 229:1358–1365.

7. Kew, O. M., B. K. Nottay, M. H. Hatch, J. H. Nakano and J. F. Obijeski. 1981. Multiple changes can occur in the oral polio vaccines upon relication in humans. J. Gen. Virol. 56:337–347.

8. Kirkegaard, K. 1990. Mutations in VP1 of poliovirus specifically affect both encapsidation and release of viral RNA. J. Virol. 64:195–206.

9. Kohara, M., A. Shinobu, S. Kuge, B. L. Semler, T. Komatsu, M. Arita, H. Itoh and A. Nomoto. 1985. An infectious cDNA clone of the poliovirus Sabin strain could be used as a stable repository and inoculum for the oral polio live vaccine. Virology 151:21–30.

10. Laemmli, U. K. 1970. Cleavage of structural proteins during the assembly of the head of bacteriophage T4. Nature (London) 227:680–685.

11. Melnick, J. L., M. Benyesh-Melnick, and J. C. Brennan. 1959. Studies on live poliovirus vaccine. JAMA. 171:63–70.

12. Moss, E. G., R. E. O'Neill, and V. R. Racaniello. 1989. Mapping of attenuating sequences of an avirulent poliovirus type 2 strain. J. Virol. 63:1884–1890.

13. Nakano, J. H., M. H. Hatch, M. L. Thieme and B. Nottay. 1978. Parameters for differentiating vaccine-derived and wild poliovirus strains. Prog. Med. Virol. 24:178–206.

14. Nomoto, A. and E. Wimmer. 1987. Genetic studies of the antigenicity and the attenuation phenotype of poliovirus, p. 107–134. In W. C. Russell and J. W. Almond (ed.), Molecular basis of virus disease. Cambridge University Press, Cambridge.

15. Racaniello, V. R. 1988. Poliovirus neurovirulence. Adv. Virus Res. 34:217–246.

16. Ren, R., E. G. Moss, and V. R. Racaniello. 1991. Indentification of two determinants that attenuate vaccine-related type 2 poliovirus. J. Virol. 65:1377–1382.

17. Stanway, G., A. J. Cann, R. Hauptmann, P. Hughes, L. D. Clarke, R. C. Mountford, P. D. Minor, G. C. Schild, and J. W. Almond. 1983. The nucleotide sequence of poliovirus type 3 leon 12 $a_1$b: comparison with poliovirus type 1. Nucleic Acids Res. 11:5629–5643.

18. Stanway, G., P. J. Hughes, R. C. Mountford, P. Reeve, P. D. Minor, G. C. Schild, and J. W. Almond. 1984. Comparison of complete nucleotide sequences of the genomes of the neurovirulent poliovirus P3/Leon/37 and its attenuated Sabin vaccine derivative P3/Leon12$a_1$b. Proc. Natl. Acad. Sci. USA 81:1539–1543.

19. Stones, P. B., C. R. Macdonald, J. K. McDougall and P. F. Ramsbottom. 1964. Preparation and properties of a derivative of Sabin's type 3 poliovirus strain Leon 12$a_1$b. 10th Symposium of the European Association against Poliomyelitis, Warsaw, pp. 390–397.

20. Tatem, J. M., C. Weeks-Levy, S. J. Mento, S. J. MiMichele, A. Georgiu, W. F. Waterfiled, B. Sheip, C. Costalas, T. Davies, M. B. Ritchey and F. R. Cano. J. Med. Virol., in press.

21. Toyoda, H., Kohara, M., Kataoka, Y., Suganuma, T., Omata, T., Imura, N., and Nomoto, A. 1984. Complete nucleotide sequences of all three poliovirus serotype genomes: Implication for gentic relationship, gene function and antigenic determinants. J. Mol. Biol. 174:561:585.

22. United States Code of Federal Regulations. 1990. Poliouvirus vaccine live oral. Title 21, Sec. 630.10–17.

23. van der Werf, S., J. Bradley, E. Wimmer, F. W. Studier and J. J. Dunn. 1986. Sythesis of infectious poliovirus RNA by purified T7 RNA polymerase. Proc. Natl. Acad. Sci. USA 83:2330–2334.

24. Weeks-Levy, C., J. M. Tatem, S. J. DiMichele, W. Waterfield, A. F. Georigu and S. J. Mento. Submitted for publication.

25. Westrop, G. D., K. A. Wareham, D. M. A. Evans, G. Dunn, P. D. Minor, D. I. Magrath, F. Taffs, S. Marsden, M. A. Skinner, G. C. Schild and J. W. Almond. 1989. Genetic basis of attenuation of the Sabin type 3 oral poliovirus vaccine. J. Virol. 63:1338–1344.

26. World Health Organization. 1990. Requirements for poliomyelitis vaccine (oral). W.H.O. Tech. Rep. Ser. 800:30–36.

What is claimed is:

1. An RNA virus cDNA having the sequence shown in FIG. 6 (SEQ ID NO: 1).

2. An RNA virus cDNA which codes for a polypeptide having the sequence shown in FIG. 6 (SEQ ID NO: 2).

* * * * *